United States Patent
Webb et al.

(10) Patent No.: US 8,454,603 B2
(45) Date of Patent: Jun. 4, 2013

(54) EXTERNAL FIXATION ASSEMBLY AND METHOD OF USE

(75) Inventors: Lawrence X. Webb, Winston-Salem, NC (US); Louis C. Argenta, Winston-Salem, NC (US); Michael J. Morykwas, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 77 days.

(21) Appl. No.: 13/094,233

(22) Filed: Apr. 26, 2011

(65) Prior Publication Data

US 2011/0202059 A1    Aug. 18, 2011

Related U.S. Application Data

(62) Division of application No. 11/694,395, filed on Mar. 30, 2007, now Pat. No. 7,931,651.

(60) Provisional application No. 60/866,327, filed on Nov. 17, 2006.

(51) Int. Cl.
    *A61F 5/04*    (2006.01)

(52) U.S. Cl.
    USPC .............................. 606/59; 604/543; 606/304

(58) Field of Classification Search
    USPC . 606/53–59, 92, 300–329; 600/571; 604/176, 604/541, 543
    See application file for complete search history.

(56) References Cited

U.S. PATENT DOCUMENTS

| 94,029 A | * | 8/1869 | Puffer | 604/257 |
| 765,746 A | | 7/1904 | Miner | |

(Continued)

FOREIGN PATENT DOCUMENTS

| AU | 2003231870 | 4/2009 |
| DE | 372727 | 3/1923 |

(Continued)

OTHER PUBLICATIONS

Fleischmann, W., et al., "Combination osteosynthesis in treating pilon fractures involving soft tissue injuries," in "Translation of an excerpt from the brochure regarding the Sixth German-Austrian-Swiss Accident Congress" allegedly dated 1991, in German with English translation.

(Continued)

*Primary Examiner* — Pedro Philogene
*Assistant Examiner* — Lynnsy Schneider
(74) *Attorney, Agent, or Firm* — Niels Haun; Dann Dorfman Herrell & Skillman, PC

(57) ABSTRACT

An external fixation assembly includes a plurality of hollow pins that are inserted into a patient's bone. Each pin has an interior bore and a plurality of apertures extending through the pin wall from the bore. The pin may be coupled to a source of vacuum pressure operable to create reduced pressure in the tissue surrounding the pin. A cover is placed around the pin and sealed to provide a fluid-tight enclosure that maintains reduced pressure around the pin. A method for applying external fixation using the fixator pins described above includes the steps of inserting each pin through a skin opening, positioning the pin apertures near selected tissue, covering the skin opening with a sealed enclosure, connecting the pins to a source of vacuum pressure, and activating the source of vacuum pressure to create reduced pressure in the patient's tissue at or near the bone.

25 Claims, 9 Drawing Sheets

U.S. PATENT DOCUMENTS

| | | |
|---|---|---|
| 774,529 A | 11/1904 | Nieschang |
| 843,674 A | 2/1907 | Funk |
| 1,000,001 A | 8/1911 | Holz |
| 1,355,679 A | 10/1920 | McDonnell |
| 1,355,846 A | 10/1920 | Rannells |
| 1,385,346 A | 7/1921 | Taylor |
| 1,936,129 A | 11/1933 | Fisk |
| 2,025,492 A | 12/1935 | Aird |
| 2,122,121 A | 6/1938 | Tillotson |
| 2,195,771 A | 4/1940 | Estler |
| 2,221,758 A | 11/1940 | Elmquist |
| 2,232,254 A | 2/1941 | Morgan |
| 2,280,915 A | 4/1942 | Johnson |
| 2,338,339 A | 1/1944 | LaMere |
| 2,443,481 A | 6/1948 | Sene |
| 2,547,758 A | 4/1951 | Keeling |
| 2,573,791 A | 11/1951 | Howells |
| 2,577,945 A | 12/1951 | Atherton |
| 2,632,443 A | 3/1953 | Lesher |
| 2,682,873 A | 7/1954 | Evans |
| 2,910,763 A | 11/1959 | Lauterbach |
| 2,969,057 A | 1/1961 | Simmons |
| 3,026,526 A | 3/1962 | Montrose |
| 3,026,874 A | 3/1962 | Stevens |
| 3,042,041 A * | 7/1962 | Jascalevich .................. 604/277 |
| 3,115,138 A | 12/1963 | McElvenny |
| 3,115,318 A | 12/1963 | Caillette |
| 3,315,665 A | 4/1967 | MacLeod |
| 3,324,855 A | 6/1967 | Heimlich |
| 3,367,332 A | 2/1968 | Groves |
| 3,382,867 A | 5/1968 | Reaves |
| 3,429,313 A | 2/1969 | Romanelli |
| 3,478,736 A | 11/1969 | Roberts et al. |
| 3,481,326 A | 12/1969 | Schamblin |
| 3,486,504 A | 12/1969 | Austin, Jr. |
| 3,520,300 A | 7/1970 | Flower et al. |
| 3,528,416 A | 9/1970 | Chamberlain |
| 3,568,675 A | 3/1971 | Harvey |
| 3,572,340 A | 3/1971 | Lloyd et al. |
| 3,610,238 A | 10/1971 | Rich, Jr. |
| 3,648,692 A | 3/1972 | Wheeler |
| 3,682,180 A | 8/1972 | McFarlane |
| 3,683,911 A * | 8/1972 | McCormick .................. 604/180 |
| 3,713,622 A | 1/1973 | Dinger |
| 3,753,439 A | 8/1973 | Brugarolas et al. |
| 3,782,377 A | 1/1974 | Rychlik |
| 3,782,387 A | 1/1974 | Falabella |
| 3,812,972 A | 5/1974 | Rosenblum |
| 3,814,095 A | 6/1974 | Lubens |
| 3,826,254 A | 7/1974 | Mellor |
| 3,874,387 A | 4/1975 | Barbieri |
| 3,877,424 A * | 4/1975 | Murray ........................... 606/54 |
| 3,896,810 A * | 7/1975 | Akiyama ....................... 604/117 |
| 3,903,882 A | 9/1975 | Augurt |
| 3,908,664 A | 9/1975 | Loseff |
| 3,935,863 A | 2/1976 | Kliger |
| 3,938,540 A | 2/1976 | Holbrook et al. |
| 3,954,105 A | 5/1976 | Nordby |
| 3,976,060 A | 8/1976 | Hildebrandt et al. |
| 3,978,855 A | 9/1976 | McRae et al. |
| 3,993,080 A | 11/1976 | Loseff |
| 3,998,227 A | 12/1976 | Holbrook et al. |
| RE29,319 E | 7/1977 | Nordby |
| 4,040,427 A * | 8/1977 | Winnie .......................... 604/180 |
| 4,065,817 A * | 1/1978 | Branemark et al. ....... 623/23.46 |
| 4,080,970 A | 3/1978 | Miller |
| 4,112,947 A | 9/1978 | Nehring |
| 4,139,004 A | 2/1979 | Gonzalez, Jr. |
| 4,149,541 A | 4/1979 | Gammons et al. |
| 4,156,066 A | 5/1979 | Gould |
| 4,157,715 A | 6/1979 | Westerhoff |
| 4,169,563 A | 10/1979 | Leu |
| 4,172,455 A | 10/1979 | Beaussant |
| 4,184,510 A | 1/1980 | Murry et al. |
| 4,191,204 A | 3/1980 | Nehring |
| 4,221,215 A | 9/1980 | Mandelbaum |
| 4,224,941 A | 9/1980 | Stivala |
| 4,224,945 A | 9/1980 | Cohen |
| 4,250,882 A | 2/1981 | Adair |
| 4,256,109 A | 3/1981 | Nichols |
| 4,261,363 A | 4/1981 | Russo |
| 4,275,721 A | 6/1981 | Olson |
| 4,297,995 A | 11/1981 | Golub |
| 4,341,209 A | 7/1982 | Schaar |
| 4,373,519 A | 2/1983 | Errede |
| 4,382,441 A | 5/1983 | Svedman |
| 4,392,853 A | 7/1983 | Muto |
| 4,399,816 A | 8/1983 | Spangler |
| 4,419,097 A | 12/1983 | Rowland |
| 4,452,845 A | 6/1984 | Lloyd et al. |
| 4,457,755 A | 7/1984 | Wilson |
| 4,459,139 A | 7/1984 | vonReis et al. |
| 4,465,062 A | 8/1984 | Versaggi et al. |
| 4,465,485 A | 8/1984 | Kashmer et al. |
| 4,469,092 A | 9/1984 | Marshall et al. |
| 4,475,909 A | 10/1984 | Eisenberg |
| 4,480,638 A | 11/1984 | Schmid |
| 4,499,896 A | 2/1985 | Heinecke |
| RE31,887 E | 5/1985 | Hodgson |
| 4,516,968 A * | 5/1985 | Marshall et al. .............. 604/174 |
| 4,519,793 A * | 5/1985 | Galindo ........................ 604/180 |
| 4,525,166 A | 6/1985 | Leclerc |
| 4,527,064 A | 7/1985 | Anderson |
| 4,533,352 A | 8/1985 | Van Beek |
| 4,540,412 A | 9/1985 | Van Overloop |
| 4,543,100 A | 9/1985 | Brodsky |
| 4,553,967 A | 11/1985 | Ferguson |
| 4,569,674 A | 2/1986 | Phillips et al. |
| 4,573,965 A | 3/1986 | Russo |
| 4,576,158 A | 3/1986 | Boland |
| 4,579,555 A | 4/1986 | Russo |
| 4,605,399 A * | 8/1986 | Weston et al. ................ 604/305 |
| 4,608,041 A | 8/1986 | Nielsen |
| 4,612,921 A * | 9/1986 | Lazo de Zbikowski ........ 606/57 |
| 4,615,338 A | 10/1986 | Ilizarov et al. |
| 4,624,656 A | 11/1986 | Clark et al. |
| 4,627,427 A | 12/1986 | Arco |
| 4,633,863 A | 1/1987 | Filips |
| 4,637,819 A | 1/1987 | Ouellette |
| 4,640,688 A | 2/1987 | Hauser |
| 4,641,643 A | 2/1987 | Greer |
| 4,653,489 A * | 3/1987 | Tronzo ............................ 606/65 |
| 4,655,754 A | 4/1987 | Richmond et al. |
| 4,661,093 A | 4/1987 | Beck et al. |
| 4,664,652 A | 5/1987 | Weilbacher |
| 4,664,662 A | 5/1987 | Webster |
| 4,667,666 A | 5/1987 | Fryslie |
| 4,675,006 A * | 6/1987 | Hrushesky .................... 604/180 |
| 4,679,590 A | 7/1987 | Hergenroeder |
| 4,710,165 A | 12/1987 | McNeil et al. |
| 4,713,052 A | 12/1987 | Beck |
| 4,717,382 A | 1/1988 | Clemens et al. |
| 4,733,659 A | 3/1988 | Edenbaum |
| 4,743,232 A | 5/1988 | Kruger |
| 4,747,166 A | 5/1988 | Kuntz |
| 4,753,231 A | 6/1988 | Lang et al. |
| 4,753,232 A | 6/1988 | Ward |
| 4,759,354 A | 7/1988 | Quarfoot |
| 4,764,167 A | 8/1988 | Tu |
| 4,765,316 A | 8/1988 | Marshall |
| 4,773,409 A | 9/1988 | Cilento et al. |
| 4,778,446 A | 10/1988 | Jensen |
| 4,778,456 A | 10/1988 | Lokken |
| 4,820,265 A | 4/1989 | DeSatnick |
| 4,820,284 A | 4/1989 | Hauri |
| 4,822,278 A | 4/1989 | Oliva |
| 4,834,110 A | 5/1989 | Richard |
| 4,836,192 A | 6/1989 | Abbate |
| 4,838,883 A | 6/1989 | Matsuura |
| 4,840,187 A | 6/1989 | Brazier |
| 4,841,962 A | 6/1989 | Berg et al. |
| 4,846,162 A | 7/1989 | Moehring |
| 4,851,545 A | 7/1989 | Song |
| 4,856,504 A * | 8/1989 | Yamamoto et al. ............. 606/59 |
| 4,860,737 A | 8/1989 | Lang et al. |
| 4,863,449 A | 9/1989 | Therriault |
| 4,872,450 A | 10/1989 | Austad |

| | | | |
|---|---|---|---|
| 4,875,473 A | 10/1989 | Alvarez | |
| 4,877,019 A | 10/1989 | Vives | |
| 4,878,901 A | 11/1989 | Sachse | |
| 4,890,608 A | 1/1990 | Steer | |
| 4,897,081 A * | 1/1990 | Poirier et al. | 604/175 |
| 4,906,233 A | 3/1990 | Moriuchi et al. | |
| 4,906,240 A * | 3/1990 | Reed et al. | 604/307 |
| 4,915,694 A * | 4/1990 | Yamamoto et al. | 604/180 |
| 4,917,112 A | 4/1990 | Kalt | |
| 4,921,492 A | 5/1990 | Schultz | |
| 4,925,447 A | 5/1990 | Rosenblatt | |
| 4,931,519 A | 6/1990 | Song | |
| 4,941,882 A | 7/1990 | Ward et al. | |
| 4,953,565 A | 9/1990 | Tachibana et al. | |
| 4,969,880 A * | 11/1990 | Zamierowski | 604/305 |
| 4,969,881 A | 11/1990 | Viesturs | |
| 4,973,331 A | 11/1990 | Pursley et al. | |
| 4,988,336 A | 1/1991 | Kohn | |
| 4,990,144 A | 2/1991 | Blott | |
| 4,991,574 A | 2/1991 | Pocknell | |
| 4,997,425 A | 3/1991 | Shioya | |
| 5,002,528 A * | 3/1991 | Palestrant | 604/28 |
| 5,002,529 A | 3/1991 | Cunningham | |
| 5,002,543 A | 3/1991 | Bradshaw | |
| 5,003,971 A | 4/1991 | Buckley | |
| 5,014,389 A | 5/1991 | Ogilvie | |
| 5,019,086 A | 5/1991 | Neward | |
| 5,034,003 A | 7/1991 | Denance | |
| 5,034,006 A | 7/1991 | Hosoda | |
| 5,034,012 A | 7/1991 | Frigg | |
| 5,035,884 A | 7/1991 | Song | |
| 5,042,978 A | 8/1991 | Quenin | |
| 5,047,030 A * | 9/1991 | Draenert | 606/65 |
| 5,060,662 A | 10/1991 | Farnsworth, III | |
| 5,071,403 A | 12/1991 | Larsson | |
| 5,073,172 A | 12/1991 | Fell | |
| 5,080,661 A * | 1/1992 | Lavender et al. | 606/54 |
| 5,086,763 A | 2/1992 | Hathman | |
| 5,086,764 A * | 2/1992 | Gilman | 602/42 |
| 5,098,435 A * | 3/1992 | Stednitz et al. | 606/916 |
| 5,100,396 A * | 3/1992 | Zamierowski | 604/305 |
| 5,100,404 A | 3/1992 | Hayes | |
| 5,101,808 A | 4/1992 | Kobayashi | |
| 5,102,413 A * | 4/1992 | Poddar | 606/62 |
| 5,103,806 A | 4/1992 | McLeod et al. | |
| 5,106,362 A | 4/1992 | Gilman | |
| 5,106,629 A | 4/1992 | Cartmell | |
| 5,113,871 A | 5/1992 | Viljanto | |
| 5,120,312 A * | 6/1992 | Wigness et al. | 604/175 |
| 5,122,114 A * | 6/1992 | Miller et al. | 604/506 |
| 5,129,904 A * | 7/1992 | Illi | 606/304 |
| 5,135,518 A | 8/1992 | Vera | |
| 5,147,338 A | 9/1992 | Lang | |
| 5,149,331 A | 9/1992 | Ferdman | |
| 5,152,757 A | 10/1992 | Eriksson | |
| 5,152,794 A | 10/1992 | Davidson | |
| 5,160,322 A | 11/1992 | Scheremet | |
| 5,167,613 A | 12/1992 | Karami | |
| 5,170,781 A | 12/1992 | Loomis | |
| 5,171,245 A * | 12/1992 | Cezana | 606/86 R |
| 5,176,663 A | 1/1993 | Svedman | |
| 5,176,667 A | 1/1993 | DeBring | |
| 5,178,137 A | 1/1993 | Goor | |
| 5,191,880 A | 3/1993 | McLeod et al. | |
| 5,192,282 A * | 3/1993 | Draenert | 606/65 |
| 5,215,539 A | 6/1993 | Schoolman | |
| 5,217,009 A | 6/1993 | Kronberg | |
| 5,224,947 A | 7/1993 | Cooper | |
| 5,228,431 A | 7/1993 | Giarretto | |
| 5,230,350 A | 7/1993 | Fentress | |
| 5,241,972 A * | 9/1993 | Bonati | 128/898 |
| 5,242,448 A | 9/1993 | Pettine | |
| 5,249,899 A * | 10/1993 | Wilson | 411/82 |
| 5,261,893 A | 11/1993 | Zamierowski | |
| 5,263,922 A | 11/1993 | Sova | |
| 5,263,955 A | 11/1993 | Baumgart et al. | |
| 5,281,221 A * | 1/1994 | Tadych | 606/53 |
| 5,298,015 A | 3/1994 | Komatsuzaki | |
| 5,304,181 A * | 4/1994 | Caspari et al. | 606/80 |
| 5,330,452 A | 7/1994 | Zook | |
| 5,334,204 A * | 8/1994 | Clewett et al. | 606/312 |
| 5,344,415 A | 9/1994 | DeBusk | |
| 5,349,965 A | 9/1994 | McCarver | |
| 5,356,411 A | 10/1994 | Spievack | |
| 5,358,494 A * | 10/1994 | Svedman | 604/313 |
| 5,372,583 A * | 12/1994 | Roberts et al. | 604/506 |
| 5,376,065 A | 12/1994 | McLeod et al. | |
| 5,376,252 A | 12/1994 | Ekstrom | |
| 5,395,315 A | 3/1995 | Griep | |
| 5,415,660 A | 5/1995 | Capmbell et al. | |
| 5,419,768 A | 5/1995 | Kayser | |
| 5,423,848 A * | 6/1995 | Washizuka et al. | 606/185 |
| 5,429,638 A | 7/1995 | Muschler | |
| 5,431,662 A | 7/1995 | Nicholas | |
| 5,437,651 A | 8/1995 | Todd | |
| 5,445,604 A | 8/1995 | Lang | |
| 5,447,492 A * | 9/1995 | Cartmell et al. | 602/58 |
| 5,451,215 A | 9/1995 | Wolter | |
| 5,456,267 A * | 10/1995 | Stark | 128/898 |
| 5,478,333 A | 12/1995 | Asherman, Jr. | |
| 5,484,399 A * | 1/1996 | DiResta et al. | 604/21 |
| 5,484,427 A | 1/1996 | Gibbons | |
| 5,487,889 A | 1/1996 | Eckert | |
| 5,496,262 A | 3/1996 | Johnson, Jr. | |
| 5,520,652 A | 5/1996 | Peterson | |
| 5,522,901 A | 6/1996 | Thomas et al. | |
| 5,527,293 A | 6/1996 | Zamierowski | |
| 5,531,670 A | 7/1996 | Westby | |
| 5,542,918 A | 8/1996 | Atkinson | |
| 5,549,584 A * | 8/1996 | Gross | 604/313 |
| 5,556,375 A | 9/1996 | Ewall | |
| 5,556,379 A * | 9/1996 | Wolfinbarger | 128/898 |
| 5,578,022 A | 11/1996 | Scherson | |
| 5,580,353 A | 12/1996 | Mendes et al. | |
| 5,588,955 A | 12/1996 | Johnson, Jr. | |
| 5,605,546 A * | 2/1997 | Wolzinger et al. | 604/174 |
| 5,607,388 A | 3/1997 | Ewall | |
| 5,626,579 A | 5/1997 | Muschler et al. | |
| 5,628,735 A | 5/1997 | Skow | |
| 5,636,643 A * | 6/1997 | Argenta et al. | 128/897 |
| 5,643,258 A * | 7/1997 | Robioneck et al. | 606/54 |
| 5,645,081 A * | 7/1997 | Argenta et al. | 128/897 |
| 5,655,258 A | 8/1997 | Heintz | |
| 5,656,027 A | 8/1997 | Ellingboe | |
| 5,662,598 A | 9/1997 | Tobin | |
| 5,662,624 A | 9/1997 | Sundstrom | |
| 5,662,625 A | 9/1997 | Westwood | |
| 5,678,564 A | 10/1997 | Lawrence | |
| 5,685,859 A * | 11/1997 | Kornerup | 604/180 |
| 5,697,920 A | 12/1997 | Gibbons | |
| 5,702,388 A * | 12/1997 | Jackson et al. | 606/54 |
| 5,716,360 A | 2/1998 | Baldwin et al. | |
| 5,717,005 A | 2/1998 | Richardson | |
| 5,717,030 A | 2/1998 | Dunn | |
| 5,720,720 A | 2/1998 | Laske et al. | |
| 5,728,160 A * | 3/1998 | Draenert | 623/16.11 |
| 5,733,884 A | 3/1998 | Barbul et al. | |
| 5,735,833 A | 4/1998 | Olson | |
| 5,738,686 A | 4/1998 | Kubein-Meesenburg et al. | |
| 5,743,912 A * | 4/1998 | Lahille et al. | 606/65 |
| 5,746,741 A * | 5/1998 | Kraus et al. | 606/54 |
| 5,759,205 A | 6/1998 | Valentini | |
| 5,762,640 A | 6/1998 | Kajiwara | |
| 5,782,871 A | 7/1998 | Fujiwara | |
| 5,797,871 A * | 8/1998 | Wolfinbarger, Jr. | 604/500 |
| 5,807,341 A | 9/1998 | Heim | 604/174 |
| 5,810,840 A | 9/1998 | Lindsay | |
| 5,817,145 A | 10/1998 | Augustine | |
| 5,820,581 A * | 10/1998 | Wolfinbarger, Jr. | 604/500 |
| 5,827,246 A | 10/1998 | Bowen | |
| 5,833,666 A * | 11/1998 | Davis et al. | 604/180 |
| 5,863,292 A * | 1/1999 | Tosic | 606/56 |
| 5,868,749 A * | 2/1999 | Reed | 606/76 |
| 5,871,484 A * | 2/1999 | Spievack et al. | 606/60 |
| 5,876,359 A | 3/1999 | Bock et al. | |
| 5,891,101 A * | 4/1999 | Wilcox et al. | 604/175 |
| 5,895,375 A * | 4/1999 | Wilcox et al. | 604/175 |
| 5,906,600 A * | 5/1999 | Bahr | 604/265 |

| | | | |
|---|---|---|---|
| 5,911,222 A | 6/1999 | Lawrence | |
| 5,919,476 A | 7/1999 | Fischer | |
| 5,921,972 A | 7/1999 | Skow | |
| 5,921,985 A * | 7/1999 | Ross et al. | 606/59 |
| 5,928,174 A | 7/1999 | Gibbins | |
| 5,928,468 A * | 7/1999 | Tolson | 156/578 |
| 5,935,136 A | 8/1999 | Hulse et al. | |
| 5,941,859 A * | 8/1999 | Lerman | 604/289 |
| 5,947,914 A | 9/1999 | Augustine | |
| 5,951,295 A | 9/1999 | Lyles et al. | |
| 5,954,680 A | 9/1999 | Augustine | |
| 5,958,314 A | 9/1999 | Draenert | |
| 5,961,480 A | 10/1999 | Augustine | |
| 5,964,721 A | 10/1999 | Augustine | |
| 5,964,723 A | 10/1999 | Augustine | |
| 5,964,733 A | 10/1999 | Laabs et al. | |
| 5,968,047 A * | 10/1999 | Reed | 606/76 |
| 5,976,104 A * | 11/1999 | Wolfinbarger, Jr. | 604/500 |
| 5,979,658 A * | 11/1999 | Allen et al. | 206/572 |
| 5,986,163 A | 11/1999 | Augustine | |
| 6,010,527 A | 1/2000 | Augustine | |
| 6,045,518 A | 4/2000 | Augustine | |
| 6,045,541 A | 4/2000 | Matsumoto | |
| 6,048,343 A * | 4/2000 | Mathis et al. | 606/916 |
| 6,051,016 A | 4/2000 | Mesaros et al. | |
| 6,053,416 A | 4/2000 | Specht | |
| 6,071,254 A | 6/2000 | Augustine | |
| 6,071,267 A | 6/2000 | Zamierowski | |
| 6,071,304 A | 6/2000 | Augustine | |
| 6,080,189 A | 6/2000 | Augustine | |
| 6,080,243 A | 6/2000 | Insley | |
| 6,086,587 A | 7/2000 | Hawk | |
| 6,087,553 A | 7/2000 | Cohen et al. | |
| 6,093,160 A | 7/2000 | Augustine | |
| 6,095,148 A | 8/2000 | Shastri et al. | |
| 6,095,992 A | 8/2000 | Augustine | |
| 6,106,525 A * | 8/2000 | Sachse | 606/59 |
| 6,110,197 A | 8/2000 | Augustine | |
| 6,113,561 A | 9/2000 | Augustine | |
| 6,117,111 A | 9/2000 | Fleischmann | |
| 6,124,521 A * | 9/2000 | Roberts | 602/54 |
| 6,135,116 A | 10/2000 | Vogel | |
| 6,142,982 A | 11/2000 | Hunt | |
| 6,143,035 A | 11/2000 | McDowell | |
| 6,143,945 A | 11/2000 | Augustine | |
| 6,146,423 A | 11/2000 | Cohen et al. | |
| 6,159,246 A | 12/2000 | Mendes et al. | |
| 6,174,306 B1 | 1/2001 | Fleischmann | |
| 6,183,470 B1 * | 2/2001 | Booth et al. | 606/53 |
| 6,187,047 B1 | 2/2001 | Kwan et al. | |
| 6,190,391 B1 | 2/2001 | Stubbs | |
| 6,203,563 B1 * | 3/2001 | Fernandez | 606/215 |
| 6,207,875 B1 | 3/2001 | Lindqvist | |
| 6,210,376 B1 * | 4/2001 | Grayson | 604/264 |
| 6,213,965 B1 | 4/2001 | Augustine | |
| 6,213,966 B1 | 4/2001 | Augustine | |
| 6,214,012 B1 * | 4/2001 | Karpman et al. | 606/93 |
| 6,217,535 B1 | 4/2001 | Augustine | |
| 6,217,581 B1 * | 4/2001 | Tolson | 606/86 R |
| 6,235,009 B1 | 5/2001 | Skow | |
| 6,235,047 B1 | 5/2001 | Augustine | |
| 6,241,697 B1 | 6/2001 | Augustine | |
| 6,241,698 B1 | 6/2001 | Augustine | |
| 6,248,084 B1 | 6/2001 | Augustine | |
| 6,254,557 B1 | 7/2001 | Augustine | |
| 6,254,580 B1 | 7/2001 | Svedman | |
| 6,264,622 B1 | 7/2001 | Augustine | |
| 6,264,979 B1 | 7/2001 | Svedman | |
| 6,267,740 B1 | 7/2001 | Augustine | |
| 6,283,931 B1 | 9/2001 | Augustine | |
| 6,284,941 B1 | 9/2001 | Cox | |
| 6,290,685 B1 | 9/2001 | Insley | |
| 6,293,917 B1 | 9/2001 | Augustine | |
| 6,323,146 B1 | 11/2001 | Pugh | |
| 6,325,788 B1 * | 12/2001 | McKay | 604/506 |
| 6,344,061 B1 | 2/2002 | Leitao et al. | |
| 6,345,623 B1 | 2/2002 | Heaton et al. | |
| 6,355,215 B1 | 3/2002 | Poggie et al. | |
| 6,359,189 B1 | 3/2002 | Fleischmann | |
| 6,377,653 B1 | 4/2002 | Lee et al. | |
| 6,394,948 B1 | 5/2002 | Borst et al. | |
| 6,398,767 B1 | 6/2002 | Fleischmann | |
| 6,402,758 B1 * | 6/2002 | Tolson | 606/94 |
| 6,423,062 B2 * | 7/2002 | Enayati | 606/59 |
| 6,430,427 B1 | 8/2002 | Lee et al. | |
| 6,458,109 B1 | 10/2002 | Henley | |
| 6,484,716 B1 | 11/2002 | Leininger | |
| 6,485,503 B2 | 11/2002 | Jacobs et al. | |
| 6,488,643 B1 | 12/2002 | Tumey | |
| 6,491,693 B1 * | 12/2002 | Lytinas | 606/53 |
| 6,517,542 B1 * | 2/2003 | Papay et al. | 606/232 |
| 6,520,982 B1 | 2/2003 | Boynton | |
| 6,537,274 B1 * | 3/2003 | Katz | 606/56 |
| 6,551,317 B2 | 4/2003 | Berish et al. | |
| 6,553,998 B2 | 4/2003 | Heaton et al. | |
| 6,555,729 B1 | 4/2003 | Fleischmann | |
| 6,565,572 B2 * | 5/2003 | Chappius | 600/300 |
| 6,648,862 B2 | 11/2003 | Watson | |
| 6,663,349 B1 | 12/2003 | Discenzo | |
| 6,673,028 B1 | 1/2004 | Argenta et al. | |
| 6,682,491 B2 | 1/2004 | Johnson | |
| 6,682,506 B1 * | 1/2004 | Navarro | 604/174 |
| 6,685,681 B2 | 2/2004 | Lockwood | |
| 6,695,823 B1 | 2/2004 | Lina | |
| 6,712,851 B1 | 3/2004 | Lemperle et al. | |
| 6,749,592 B2 | 6/2004 | Lord | |
| 6,752,794 B2 | 6/2004 | Lockwood | |
| 6,755,807 B2 | 6/2004 | Risk, Jr. | |
| 6,755,835 B2 * | 6/2004 | Schultheiss et al. | 606/304 |
| 6,764,462 B2 | 7/2004 | Risk, Jr. | |
| 6,767,334 B1 | 7/2004 | Randolph | |
| 6,770,794 B2 | 8/2004 | Fleischmann | |
| 6,793,633 B2 | 9/2004 | Douglas et al. | |
| 6,800,074 B2 | 10/2004 | Henley | |
| 6,814,079 B2 | 11/2004 | Heaton et al. | |
| 6,824,533 B2 | 11/2004 | Risk, Jr. | |
| 6,832,611 B2 * | 12/2004 | Altman | 128/846 |
| 6,840,960 B2 | 1/2005 | Bubb | |
| 6,855,135 B2 * | 2/2005 | Lockwood et al. | 604/313 |
| 6,856,821 B2 | 2/2005 | Johnson | |
| 6,863,674 B2 * | 3/2005 | Kasahara et al. | 606/108 |
| 6,878,119 B2 | 4/2005 | Johnson | |
| 6,884,920 B2 * | 4/2005 | Worthley | 602/55 |
| 6,887,246 B2 * | 5/2005 | Bhatnagar et al. | 606/94 |
| 6,936,037 B2 | 8/2005 | Bubb | |
| 6,951,553 B2 | 10/2005 | Bubb | |
| 6,981,974 B2 * | 1/2006 | Berger | 606/304 |
| 6,988,423 B2 | 1/2006 | Bolam | |
| 6,994,702 B1 | 2/2006 | Johnson | |
| 7,004,915 B2 | 2/2006 | Boynton | |
| 7,022,113 B2 | 4/2006 | Lockwood | |
| 7,070,584 B2 | 7/2006 | Johnson | |
| 7,077,832 B2 | 7/2006 | Fleischmann | |
| 7,108,683 B2 | 9/2006 | Zamierowski | |
| 7,117,869 B2 | 10/2006 | Heaton | |
| 7,128,735 B2 | 10/2006 | Weston | |
| 7,144,390 B1 | 12/2006 | Hannigan | |
| 7,169,151 B1 | 1/2007 | Lytinas | |
| 7,175,625 B2 | 2/2007 | Culbert | |
| 7,198,046 B1 * | 4/2007 | Argenta et al. | 128/897 |
| 7,216,651 B2 | 5/2007 | Argenta et al. | 128/897 |
| 7,250,055 B1 * | 7/2007 | Vanderwalle | 606/92 |
| 7,276,051 B1 | 10/2007 | Henley et al. | |
| 7,279,612 B1 | 10/2007 | Heaton et al. | |
| RE39,995 E * | 1/2008 | Pepper et al. | 606/80 |
| 7,338,482 B2 * | 3/2008 | Lockwood et al. | 604/543 |
| 7,338,493 B1 * | 3/2008 | Vandewalle | 606/86 A |
| 7,344,512 B2 * | 3/2008 | Yamazaki et al. | 604/6.11 |
| 7,354,442 B2 * | 4/2008 | Sasso et al. | 606/280 |
| 7,361,184 B2 * | 4/2008 | Joshi | 606/213 |
| 7,520,872 B2 * | 4/2009 | Biggie et al. | 604/319 |
| 7,576,256 B2 * | 8/2009 | Bjornberg et al. | 602/48 |
| 7,658,749 B2 * | 2/2010 | Wittmann | 606/215 |
| 7,666,212 B2 * | 2/2010 | Pathak | 606/304 |
| 7,699,830 B2 * | 4/2010 | Martin | 604/540 |
| 7,717,945 B2 * | 5/2010 | Jensen et al. | 606/284 |
| 7,753,894 B2 * | 7/2010 | Blott et al. | 604/305 |
| 7,794,450 B2 * | 9/2010 | Blott et al. | 604/543 |

| | | | |
|---|---|---|---|
| 7,914,537 B2* | 3/2011 | Boyd et al. | 606/92 |
| 7,927,339 B2* | 4/2011 | Ralph et al. | 606/92 |
| 7,999,145 B2* | 8/2011 | Kairinos | 602/42 |
| 8,053,624 B2* | 11/2011 | Propp | 602/41 |
| 8,066,712 B2* | 11/2011 | Truckai et al. | 606/93 |
| 8,109,932 B2* | 2/2012 | Lytinas | 606/86 R |
| 8,123,699 B2* | 2/2012 | Lyon | 600/567 |
| 2001/0021852 A1* | 9/2001 | Chappius | 606/73 |
| 2001/0023349 A1* | 9/2001 | VanTassel et al. | 606/53 |
| 2001/0029956 A1* | 10/2001 | Argenta et al. | 128/897 |
| 2001/0043943 A1 | 11/2001 | Coffey | |
| 2002/0065494 A1 | 5/2002 | Lockwood et al. | |
| 2002/0082567 A1 | 6/2002 | Lockwood et al. | |
| 2002/0115952 A1 | 8/2002 | Johnson et al. | |
| 2002/0120185 A1 | 8/2002 | Johnson | |
| 2002/0143286 A1 | 10/2002 | Tumey | |
| 2002/0143344 A1 | 10/2002 | Taylor | |
| 2002/0143403 A1 | 10/2002 | Vaidyanathan et al. | |
| 2002/0161317 A1 | 10/2002 | Risk et al. | |
| 2002/0161346 A1 | 10/2002 | Lockwood et al. | |
| 2002/0169453 A1* | 11/2002 | Berger | 606/73 |
| 2002/0198503 A1 | 12/2002 | Risk, Jr. et al. | |
| 2002/0198504 A1 | 12/2002 | Risk, Jr. et al. | |
| 2003/0040687 A1 | 2/2003 | Boynton | |
| 2003/0050594 A1 | 3/2003 | Zamierowski | |
| 2003/0083662 A1* | 5/2003 | Middleton | 606/72 |
| 2003/0093075 A1* | 5/2003 | Levinson | 606/54 |
| 2003/0108587 A1 | 6/2003 | Orgill et al. | |
| 2003/0130599 A1 | 7/2003 | Restle et al. | |
| 2003/0187367 A1 | 10/2003 | Odland | |
| 2003/0208149 A1 | 11/2003 | Coffey | |
| 2003/0219469 A1 | 11/2003 | Johnson | |
| 2003/0225347 A1* | 12/2003 | Argenta et al. | 601/6 |
| 2003/0225441 A1 | 12/2003 | Boynton | |
| 2004/0006319 A1 | 1/2004 | Lina | |
| 2004/0024351 A1 | 2/2004 | Greter | |
| 2004/0030304 A1 | 2/2004 | Hunt | |
| 2004/0039391 A1* | 2/2004 | Argenta et al. | 606/86 |
| 2004/0039415 A1 | 2/2004 | Zamierowski | |
| 2004/0064111 A1 | 4/2004 | Lockwood et al. | |
| 2004/0064132 A1 | 4/2004 | Boehringer | |
| 2004/0073151 A1 | 4/2004 | Weston | |
| 2004/0122434 A1* | 6/2004 | Argenta et al. | 606/86 |
| 2004/0138522 A1* | 7/2004 | Haarstad et al. | 600/37 |
| 2004/0167482 A1 | 8/2004 | Watson | |
| 2004/0225178 A1 | 11/2004 | Kriewall | |
| 2004/0225208 A1 | 11/2004 | Johnson | |
| 2004/0249353 A1 | 12/2004 | Risks, Jr. et al. | |
| 2004/0260230 A1 | 12/2004 | Randolph | |
| 2004/0267265 A1* | 12/2004 | Kyle | 606/73 |
| 2005/0015059 A1* | 1/2005 | Sweeney | 604/264 |
| 2005/0020955 A1 | 1/2005 | Sanders | |
| 2005/0028828 A1 | 2/2005 | Heaton et al. | |
| 2005/0043659 A1 | 2/2005 | Challis et al. | |
| 2005/0055030 A1* | 3/2005 | Falahee | 606/92 |
| 2005/0065484 A1 | 3/2005 | Watson, Jr. | |
| 2005/0080423 A1* | 4/2005 | Hagan et al. | 606/86 |
| 2005/0090787 A1 | 4/2005 | Risk, Jr. et al. | |
| 2005/0101940 A1 | 5/2005 | Radl | |
| 2005/0107800 A1* | 5/2005 | Frankel et al. | 606/92 |
| 2005/0124966 A1 | 6/2005 | Karpowicz | |
| 2005/0124988 A1* | 6/2005 | Terrill-Grisoni et al. | 606/53 |
| 2005/0131327 A1 | 6/2005 | Lockwood et al. | |
| 2005/0148913 A1 | 7/2005 | Weston | |
| 2005/0165350 A1 | 7/2005 | Greter | |
| 2005/0177190 A1 | 8/2005 | Zamierowski | |
| 2005/0182445 A1 | 8/2005 | Zamierowski | |
| 2005/0197645 A1 | 9/2005 | Karpowicz | |
| 2005/0203452 A1 | 9/2005 | Weston | |
| 2005/0209574 A1 | 9/2005 | Boehringer | |
| 2005/0222527 A1 | 10/2005 | Miller | |
| 2005/0222528 A1 | 10/2005 | Weston | |
| 2005/0222544 A1 | 10/2005 | Weston | |
| 2005/0228329 A1 | 10/2005 | Boehringer | |
| 2005/0234510 A1 | 10/2005 | Zamierowski | |
| 2005/0240220 A1 | 10/2005 | Zamierowski | |
| 2005/0261615 A1 | 11/2005 | Weston | |
| 2005/0261642 A1* | 11/2005 | Weston | 604/313 |
| 2005/0283105 A1 | 12/2005 | Heaton et al. | |
| 2006/0025727 A1 | 2/2006 | Boehringer | |
| 2006/0029650 A1 | 2/2006 | Coffey | |
| 2006/0029675 A1 | 2/2006 | Ginther | |
| 2006/0079852 A1 | 4/2006 | Bubb | |
| 2006/0100586 A1 | 5/2006 | Karpowicz | |
| 2006/0149170 A1 | 7/2006 | Boynton | |
| 2006/0149171 A1 | 7/2006 | Vogel | |
| 2006/0149176 A1 | 7/2006 | Bolam | |
| 2006/0173253 A1 | 8/2006 | Ganapathy | |
| 2006/0189910 A1* | 8/2006 | Johnson et al. | 602/42 |
| 2006/0213527 A1* | 9/2006 | Argenta et al. | 128/898 |
| 2006/0241593 A1* | 10/2006 | Sherman et al. | 606/61 |
| 2006/0286076 A1 | 12/2006 | Fleischmann | |
| 2007/0005028 A1 | 1/2007 | Risk, Jr. et al. | |
| 2007/0014837 A1 | 1/2007 | Johnson | |
| 2007/0021697 A1 | 1/2007 | Ginter | |
| 2007/0021698 A1 | 1/2007 | Fleischmann | |
| 2007/0032754 A1 | 2/2007 | Walsh | |
| 2007/0071790 A1 | 3/2007 | Ameer et al. | |
| 2007/0135795 A1* | 6/2007 | De Paulis | 604/541 |
| 2007/0219585 A1* | 9/2007 | Cornet et al. | 606/221 |
| 2007/0233022 A1 | 10/2007 | Henley et al. | |
| 2007/0260226 A1* | 11/2007 | Jaeb et al. | 604/543 |
| 2007/0265561 A1* | 11/2007 | Yeung | 604/27 |
| 2008/0051828 A1* | 2/2008 | Sample et al. | 606/213 |
| 2008/0103489 A1* | 5/2008 | Dahners | 604/543 |
| 2008/0147048 A1* | 6/2008 | Deutsch | 604/541 |
| 2008/0312700 A1* | 12/2008 | James | 606/304 |
| 2009/0163893 A1* | 6/2009 | Opie et al. | 604/541 |
| 2009/0275922 A1* | 11/2009 | Coulthard et al. | 604/543 |
| 2009/0299341 A1* | 12/2009 | Kazala et al. | 604/543 |
| 2009/0318842 A1* | 12/2009 | Kairinos | 602/52 |
| 2010/0049151 A1* | 2/2010 | Aicher | 604/319 |
| 2010/0069886 A1* | 3/2010 | Wilkes | 604/543 |
| 2010/0305617 A1* | 12/2010 | Cragg | 606/279 |
| 2011/0060373 A1* | 3/2011 | Russell et al. | 606/304 |
| 2011/0245881 A1* | 10/2011 | Mitchell | 606/304 |
| 2012/0029432 A1* | 2/2012 | Sweeney | 604/151 |

FOREIGN PATENT DOCUMENTS

| | | |
|---|---|---|
| DE | 561757 | 10/1932 |
| DE | 847475 | 8/1952 |
| DE | 1963258 | 6/1971 |
| DE | 2809828 | 9/1978 |
| DE | 3102674 | 9/1982 |
| DE | 3539533 | 5/1987 |
| DE | 4111122 | 4/1993 |
| DE | 29504378 | 9/1995 |
| DE | 19722075 | 10/1998 |
| DK | 64055 | 10/1945 |
| EP | 0117632 | 9/1984 |
| EP | 0424165 | 4/1991 |
| EP | 0485657 | 5/1992 |
| EP | 0620720 A1 | 5/1993 |
| EP | 0547496 | 6/1993 |
| EP | 0620720 B1 | 10/1994 |
| EP | 0620720 B2 | 10/1994 |
| EP | 0688189 | 12/1995 |
| EP | 0777504 | 6/1997 |
| EP | 0821929 | 2/1998 |
| EP | 0853950 | 7/1998 |
| EP | 0880953 | 12/1998 |
| EP | 1023872 A2 | 8/2000 |
| EP | 1064958 | 1/2001 |
| EP | 1088569 | 4/2001 |
| EP | 1023872 A3 | 8/2002 |
| EP | 1452191 | 9/2004 |
| FR | 500253 | 3/1920 |
| FR | 1303238 | 9/1962 |
| GB | 190203090 | 6/1902 |
| GB | 114754 | 4/1918 |
| GB | 641061 | 8/1950 |
| GB | 1273342 | 5/1972 |
| GB | 1315796 | 5/1973 |
| GB | 1457164 | 12/1976 |
| GB | 1549756 | 8/1979 |
| GB | 2195255 | 4/1988 |
| GB | 2329127 | 3/1999 |
| GB | 2333965 | 8/1999 |

| | | |
|---|---|---|
| GB | 2336546 | 10/1999 |
| GB | 2342584 | 4/2000 |
| GB | 2344531 | 6/2000 |
| GB | 2351025 | 12/2000 |
| JP | 2000237219 | 9/2000 |
| SE | 84485 | 10/1935 |
| SU | 587941 | 1/1978 |
| SU | 1416108 | 7/1985 |
| SU | 1251912 | 8/1986 |
| SU | 1268175 | 11/1986 |
| WO | 80/01139 | 6/1980 |
| WO | 87/00439 | 1/1987 |
| WO | 87/04626 | 8/1987 |
| WO | WO 89/04158 | 5/1989 |
| WO | 90/10424 | 9/1990 |
| WO | 9011795 | 10/1990 |
| WO | 9100718 | 1/1991 |
| WO | 9116030 | 10/1991 |
| WO | 9219313 | 11/1992 |
| WO | 9220299 | 11/1992 |
| WO | 93/09727 | 5/1993 |
| WO | 94/00090 | 1/1994 |
| WO | 94/20041 | 9/1994 |
| WO | 96/05873 | 2/1996 |
| WO | 96/15745 | 5/1996 |
| WO | 99/13793 | 3/1999 |
| WO | 99/51164 | 10/1999 |
| WO | 00/07653 | 2/2000 |
| WO | 00/15277 | 3/2000 |
| WO | 00/21586 | 4/2000 |
| WO | 00/26100 | 5/2000 |
| WO | 00/30567 | 6/2000 |
| WO | 00/32247 | 6/2000 |
| WO | 00/38552 | 7/2000 |
| WO | 00/38755 | 7/2000 |
| WO | 00/42958 | 7/2000 |
| WO | 00/59418 | 10/2000 |
| WO | 00/59424 | 10/2000 |
| WO | 00/61206 | 10/2000 |
| WO | 00/64394 | 11/2000 |
| WO | 01/34223 | 5/2001 |
| WO | 01/37922 | 5/2001 |
| WO | 01/49233 | 7/2001 |
| WO | 01/85248 | 11/2001 |
| WO | WO 01/89431 | 11/2001 |
| WO | WO 02/43634 | 6/2002 |
| WO | 03/005943 | 1/2003 |
| WO | 03/101385 | 12/2003 |
| WO | WO 03/101508 | 12/2003 |
| WO | 2005/102234 | 11/2005 |
| WO | 2008063281 | 5/2008 |

OTHER PUBLICATIONS

Fleischmann, W., et al., "Combination osteosynthesis in the treatment of pylon fractures with soft tissue damage," labeled "Anlage NK10," pp. 178-181 and showing "6. German-Austrian-Swiss Trauma Conference in Vienna May 21-25, 1991," published in "Der Unfallchirurg" [The Traumatologist] in 1993, in German with English translation.

Juchli, L., "Krankenpflege [Nursing] Practice and Theory of Promoting Health and Patient Care," Georg Thieme Verlag Stuttgart, labeled as "Anlage 6.1" 1991 (allegedly dated Feb. 1991), and email dated May 30, 2007 labeled as "Anlage 6.2," both in German with English translations.

Turner, T.D., et al., eds., Excerpts from "Advances in wound management," including "Recent advances in wound management products" by T.D. Turner and "The role of foam dressings in wound management" by S. Thomas, Proceedings of a symposium held at the Welsh School of Pharmacy, University of Wales Institute of Science and Technology, Cardiff, Mar. 20-21, 1985, labeled as "Anlage NK13," 1986.

ISO 10079-1, "International Standard," "Medical suction equipment—Part 1: electrically powered suction equipment—Safety requirements," dated May 15, 1991.

"Coldex," labeled as "Anlage NK12" in German with English translation.

Svedman, "Irrigation Treatment of Leg Ulcers", The Lancet, Sep. 3, 1983, pp. 532-534.

Svedman, P., et al., "Staphylococcal wound infection in the pig: Part I. Course," Ann. Plast. Surg., 23(3):212-218, (Sep. 1989).

Addition to the "Users Manual Concerning Overflow Protection—Concerns all Egnell Pumps", dated Feb. 3, 1983, 1 page Swedish, [1 page English].

Addition to the "Users Manual Concerning Overflow Protection—Concerns all Egnell Pumps", dated Feb. 3, 1983, 2 pages of English translation.

Egnell Minor, Instruction Book, First Addition [Edition], allegedly dated Feb. 1987, 21 pages Swedish, 3 pages English.

Egnell Minor, Instruction Book, First Edition allegedly dated Feb. 1987, 34 pages of English translation.

Sanden, G., et al., "Staphylococcal wound infection in the pig: Part II. Inoculation, quanitifcation of bacteria, and reproducibility," Ann. Plast. Surg., 23(3):219-223, (Sep. 1989).

Inter Partes Reexam of US 7,216,651, Reexam No. 95/001,048, Order granting request for reexamination, mailed Aug. 4, 2008.

Ex Parte Reexam of US 5645081, Reexam No. 90/010,186, Order granting request for reexamination, mailed Aug. 28, 2008.

Ex Parte Reexam of US 5636643, Reexam No. 90/010,187, Order granting request for reexamination, mailed Aug. 28, 2008.

Reexam of US 7,198,046, Reexam No. 90/008,711, Notice of Intent to Issue Ex Parte Reexamination Certificate, mailed Aug. 20, 2008.

Reexam of US 5,636,643, Reexam No. 90/008,697, Final office action, mailed Jul. 24, 2008.

Bagautdinov, N. A., "Alternative method of external vacuum aspiration in the treatment of purulent soft tissue disease," Curr. Problems Contemporary Clin. Surg.: Interscholastic Collection, pp. 94-96, (6 sheets of English translation and certification dated May 30, 2008; four sheets of English translation, 6 sheets in Russian, and certification dated May 9, 2008; 1 sheet of English translation of alleged library index card, 1 sheet in Russian, and certification dated May, 7, 2008); I.N. Ulianov Chuvash State University, Cheboksary, (1986).

Zivadinovic, G., et al., "Vacuum therapy in the treatment of peripheral blood vessels," Conference Papers of the 5th Timok Medical Days, Majdanpek, No. 3-4, pp. 161-164, (5 sheets English translation; 5 sheets in Serbian, certification dated May 9, 2008) (1986).

Johnson, F.E., "An improved technique for skin graft placement using a suction drain", Surg. Gynecol. Obstet., 159 (6):584-585 (Dec. 1984).

Safronov, A.A., Dissertation Abstract, "Vacuum therapy of trophic ulcers of the lower leg with simultaneous autoplasty of the skin," (Central Scientific Research Institute of Traumatology and Orthopedics, Moscow, U.S.S.R.) (23 sheets English translation; 23 sheets in Russian; certification dated May 8, 2008; alleged index card(English translation; 1 sheet Russian; certification dated May 14, 2008), (1967).

Tribble, D.E., "An improved sump drain-irrigation device of simple construction," Arch. Surg., 105:511-513, (Sep. 1972).

Tennant, C.E., "The use of hyperemia in the postoperative treatment of lesions of the extremities and thorax," Jour. A.M.A., 64(19):1548-1549, (May 8, 1915).

Orgill, D.P., et al., "Microdeformational wound therapy—a new era in wound healing," Business Briefing: Global Surgery—Future Directions, pp. 22, 24-25 (2005).

"V.A.C.® Therapy Clinical Guidelines: A reference source for clinicians," KCI, The Clinical Advantage ® (Jul. 2007).

Bagautdinov, N. A., "Variant of external vacuum aspiration in the treatment of purulent diseases of soft tissues," Current Problems in Modern Clinical Surgery, Interdepartmental Collection, Cheboksary, (4 pages of English translation, 6 sheets in Russian, certification dated May 22, 2008, English translation of index card, 1 sheet Russian, certification dated May 7, 2008) (1986).

Chardak, W.M., et al., "Experimental studies on synthetic substitutes for skin and their use in the treatment of burns," Ann. Surg., 155(1):127-139, (Jan. 1962).

Fujimori, R., et al., "Sponge fixation method for treatment of early scars," Plast. & Reconst. Surg., 42(4):322-326, (Oct. 1968).

Kirk-Othmer, Encyclopedia of Chemical Technology, 2nd completely revised edition, vol. 14, pp. 227, John Wiley & Sons, Inc., (1967).

Meyer, W., et al., excerpts from "Bier's Hyperemic Treatment", W.B. Saunders and Co., (47 sheets) (1908).

Zivadinovic, G., et al., "Vacuum therapy in the treatment of peripheral blood vessels," Timok Medical Journal, Abstract book of the 5th Timok Medical Days, Majdanpek, 6 sheets of English translation, (1986).

Safronov, A.A., "Vacuum therapy for trophic ulcers of the tibia with concurrent skin autoplasty," Dissertation abstract, additional abstract, Moscow, 20 sheets of English translation, (1967).

Safronov, A.A., Abstract of Invention No. 240188, "Device for wound or ulcer treatment," (2 sheets English translation and 2 sheets in Russian) (1969).

Westaby, S., et al., "A wound irrigation device," Lancet, pp. 503-504, (Sep. 2, 1978).

Thomas, S., "Wound management and dressings," cover sheet, preface, sheet labeled "Chapter 5" and pp. 36-39 (1990).

Svedman, P., et al., "A dressing system providing fluid supply and suction drainage used for continuous or intermittent irrigation", Ann. Plast. Surg., 17(2):125-33 (Aug. 1986).

"Pressure equivalents," McGraw-Hill Encyclopedia of Science & Technology, 6th ed., New York, pp. 249, (1987).

Stone, P., et al., "Bolster versus negative pressure wound therapy for securing split-thickness skin grafts in trauma patients", Wounds, 16(7):219-23 (5 sheets) (2004) (Posted Aug. 4, 2004).

Wolvos, T., "Wound instillation with negative pressure wound therapy", Ostomy Wound Manage., 51(2A suppl):21S-26S (Feb. 2005)

Jeter, K., "Closed suction wound drainage system", JWOCN, 31(2):51 (1 sheet) (Mar.-Apr. 2004).

Agarwal, J.P., et al., "Vacuum-assisted closure for sternal wounds: a first-line therapeutic management approach", Plast. Reconstr. Surg., 116(4):1035-1040 (Sep. 15, 2005).

Sjogren, J., et al., "The impact of vacuum-assisted closure on long-term survival after post-sternotomy mediastinitis", Ann. Thorac. Surg., 80(4):1270-5, (Oct. 2005).

Mendez-Eastman, S., "New advances in wound therapy", printout from Wounds1.com; 7 sheets (Apr. 15, 2005).

"Promoting wound healing", Nurses-Digest, 2(3), 6 sheets, Mar. 2005.

Roylance, L., "Nancy Sujeta, Amanda Clark,"DOME, vol. 55, Mar. 2004, 2 sheets of website printout www.hopkinsmedicine.org/dome/0405/feature4.cfm.

Agarwal, J.P., et al., "Vacuum assisted closure™ for sternal wounds: a first line therapeutic management", ASPS, Plastic Surgery 2004, Philadelphia, PA, abstract (2 sheets) (Wednesday Oct. 13, 2004).

Gomoll, A.H., et al., "Incisional vacuum-assisted closure therapy", J. Orthop. Trauma, 20(10):705-709, (Nov.-Dec. 2006).

Leininger, B.E., et al., "Experience with wound VAC and delayed primary closure of contaminated soft tissue injuries in Iraq", J. Trauma, 61(5):1207-1211 (Nov. 2006).

Gupta, S., ed., "Differentiating negative pressure wound therapy devices: an illustrative case series", Wounds, 19(1 suppl):1-9, (Jan. 2007).

Korasiewicz, L.M., "Abdominal Wound With a Fistula and Large Amount of Drainage Status After Incarcerated Hernia Repair", Journal of Wound, Ostomy & Continence Nursing. 31(3):150-153, (May-Jun. 2004).

Guntinas-Lichius, O., et al., "The role of growth factors for disease and therapy in diseases of the head and neck", DNA and Cell Biol., 22(9):593-606, (Sep. 2003).

Goldman, R., "Growth factors and chronic wound healing: past, present, and future", Adv. Skin Wound Care, 17(1):24-35, (Jan.-Feb. 2004).

Malli, S., "Keep a close eye on vacuum-assisted wound closure", Nursing, 35(7):25 (Jul. 2005).

Lynch, J.B., et al., "Vacuum-assisted closure therapy: a new treatment option for recurrent pilonidal sinus disease. Report of three cases", Dis. Colon Rectum, 47(6):929-32 (Jun. 2004) (Published online May 4, 2004).

MX: Business Strategies for Medical Technology Executives, (Mar./Apr. 2005).

Niezgoda, J.A., "Incorporating negative pressure therapy into the management strategy for pressure ulcers", Ostomy Wound Manage., 50(11A suppl.):5S-8S, (Nov. 2004).

Banwell, P.E., "Topical negative pressure therapy: advances in burn wound management", Ostomy Wound Manage., 50(11A suppl.):9S-14S, (Nov. 2004).

Kaplan, M., "Negative pressure wound therapy in the management of abdominal compartment syndrome", Ostomy Wound Manage., 50(11A suppl):20S-25S, (Nov. 2004).

Gupta, S., et al., "The perioperative use of negative pressure wound therapy in skin grafting", Ostomy Wound Manage., 50(11A suppl.):26S-28S, (Nov. 2004).

Schoemann, M.B., et al., "Treating surgical wound dehiscence with negative pressure dressings", Ostomy Wound Manage., 51(2A suppl.):15S-20S, (Feb. 2005).

Bookout, K., et al., "Case studies of an infant, a toddler, and an adolescent treated with a negative pressure wound treatment system", J. Wound Ostomy Continence Nurs., 31(4):184-192, (8 pp.) (Jul./Aug. 2004).

Borkowski, S., "G tube care: managing hypergranulation tissue", Nursing, 35(8):24 (Aug. 2005).

Machen, M. S., "Management of traumatic war wounds using vacuum-assisted closure dressings in an austere environment," Army Medical Department J., pp. 17-23, (Jan.-Mar. 2007).

Peck, M.A., et al., "The complete management of extremity vascular injury in a local population: a wartime report from the 332nd Expeditionary Medical Group/Air Force Theater Hospital, Balad Air Base, Iraq," J. Vasc. Surg., pp. 1-9, (2007), (Presented at the Plenary Session of the Eastern Vascular Society's Twentieth Annual Meeting, Washington D.C., Sep. 30, 2006).

Giovannini, U.M., et al., "Topical negative therapy and vacuum assisted closure. New strategies and devices in surgical reconstruction", Minerva Chir., 60(3):191-4 (Jun. 2005).

Moues, C.M., et al., "An economic evaluation of the use of TNP on full-thickness wounds", J. Wound Care, 14(5):224-7 (May 2005).

Lee, S.S., et al., "Management of intractable sternal wound infections with topical negative pressure dressing", J. Card. Surg., 20(3):218-22 (May-Jun. 2005).

Jethwa, P., et al., "Using topical negative pressure therapy to resolve wound failure following perineal resection", J. Wound Care, 14(4):166-7 (Apr. 2005).

Banwell, P.E., et al., "Topical negative pressure therapy: mechanisms and indications", Int. Wound J., 1(2):95 (15 pages) (Jun. 2004).

Melano, E., et al., "The effects of Panafil when using topical negative pressure to heal an infected sternal wound,"J. Wound Care, 13(10):425-6 (Nov. 2004).

Morton, N., "Use of topical negative pressure therapy in postoperative dehisced or infected wounds", J. Wound Care, 13(8):346-8 (Sep. 2004).

Moisidis, E., et al., "A prospective, blinded, randomized, controlled clinical trial of topical negative pressure use in skin grafting", Plast. Reconstr. Surg., 114(4):917-919, 921-22 (6 sheets) (Sep. 15, 2004).

Tachi, M., et al., "Topical negative pressure using a drainage pouch without foam dressing for the treatment of undetermined pressure ulcers", Ann. Plast. Surg., 53(4):338-42 (7 sheets) (Oct. 2004).

Jones, S.M., et al., "Complications of topical negative pressure therapy in small-diameter wounds", Plast. Reconstr. Surg., 114(3):815-817 (5 sheets) (Sep. 1, 2004).

Loree, S., et al., "Is vacuum assisted closure a valid technique for debriding chronic leg ulcers?"J. Wound Care, 13 (6):249-52 (Jun. 2004).

Vogt, P.M., et al., "Several aspects of foam materials and their possible interactions with the wound surface in the vacuum therapy", Zentralbl. Chir., (English abstract on first page, 1 sheet printout from PubMed); 129 Suppl 1:S92-S94 (May 2004).

Haslik, W., et al., "The use of subatmospheric pressure to prevent burn wound progression: first experiences in burn wound treatment", Zentralbl. Chir., (English abstract on first page, and 1 sheet printout from PubMed); 129 Suppl. 1: S62-63 (May 2004).

Steenvoorde, P., et al., "Combining topical negative pressure and a Bogota bag for managing a difficult laparostomy", J. Wound Care, 13(4):142-3 (Apr. 2004).

Pullen, R., "Treatment of pressure sores in elderly patients", Z. Genrontol. Geriatr., (English abstract on first page, 1 sheet printout from PubMed); 37(2):92-9 (Apr. 2004).

Gottrup, F., "Optimizing wound treatment through health care structuring and professional education", Wound Repair Regen., 12(2):129-33 (Mar.-Apr. 2004).

(Anon.) "New best practice guidelines for managing pressure ulcers with negative pressure wound therapy published", Home Healthcare Nurse, 23(7):469 (one sheet) (Jul. 2005).

Stechmiller, J.K., et al., "Effect of negative pressure wound therapy on the expression of TNF-alpha, IL-1beta, MMP-2, MMP-3, and TIMP-1 in wound fluids of adults with pressure ulcers", Wound Repair Regen., 13(2):A16 (Mar.-Apr. 2005).

Snyder, R.J., "Negative pressure wound therapy (NPWT)/ vacuum-assisted closure® (VAC®) as an adjunct in the treatment of pyoderma gangrenosum", Wound repair and regeneration, 13:A29 (Mar. 2005).

Armstrong, D.G., et al., "Negative pressure wound therapy in treatment of diabetic foot wounds: a marriage of modalities", Ostomy Wound Manage., 50(4A suppl):9-12 (Apr. 2004).

Armstrong, D.G., et al., "Plantar pressure changes using novel negative pressure wound therapy technique", J. Am. Podiatr. Med. Assoc., 94(5):456-60 (Sep.-Oct. 2004).

Baharestani, M.M., "Negative pressure wound therapy: an examination of cost-effectiveness", Ostomy Wound Manage., 50(11A suppl):29S-33S (Nov. 2004).

Bernstein, B.H., et al., "Combination of subatmospheric pressure dressing and gravity feed antibiotic instillation in the treatment of post-surgical diabetic foot wounds: a case series," parts 1 and 2, Wounds, 17(2):37-48 (23 sheets) (Feb. 2005).

Datiashvili, R.O., et al., "Negative pressure dressings: An alternative to free tissue transfers?" Wounds, 17 (8):206-212 (Aug. 2005).

De Leon, J., "Negative pressure wound therapy in pressure ulcer management", Ostomy Wound Manage., 51(2A suppl):3S-8S (Feb. 2005).

Dobke, M.K., et al., "A novel approach to acute infection of the glenohumeral joint following rotator cuff repair—a case series", Wounds, 17(6):137-40 (6 sheets) (Jun. 2005).

Dunbar, A., et al., "Addressing the pain: Silicone net dressings as an adjunct with negative pressure wound therapy", Ostomy Wound Manage., 51(4):18-20 (4 sheets) (Apr. 2005).

Etoz, A., et al., "The use of negative pressure wound therapy on diabetic foot ulcers: A preliminary controlled trial", Wounds, 16(8):264-9 (Aug. 2004).

Fife, C.E., et al., "Healing dehisced surgical wounds with negative pressure wound therapy", Ostomy Wound Manage., 50(4A suppl):28-31 (Apr. 2004).

Geller, S.M., et al., "Ulceration of pyoderma gangrenosum treated with negative pressure wound therapy", J. Am. Podiatr. Med. Assoc., 95(2):171-4 (Mar.-Apr. 2005).

Gray, M., et al., "Is negative pressure wound therapy effective for the management of chronic wounds?"J. Wound Ostomy Continence Nurs., 31(3):101-5 (May-Jun. 2004).

Gupta, S., et al., "A literature review of negative pressure wound therapy", Ostomy Wound Manage., 50(11A suppl):2S-4S (Nov. 2004).

Gupta, S., et al., "The perioperative use of negative pressure wound therapy in skin grafting", Ostomy Wound Mangage., 50(4A suppl):32-4 (Apr. 2004).

Gupta, S., et al., "Guidelines for managing pressure ulcers with negative pressure wound therapy", Adv. Skin Wound Care, 17(Suppl 2):1-16 (Nov.-Dec. 2004).

Huljev, D., et al., "Necrotizing fasciitis of the abdominal wall as a post-surgical complication: a case report", Wounds, 17(7):169-77 (10 sheets) (2005) (Posted Aug. 11, 2005).

Kaplan, M., "Negative pressure wound therapy in the management of abdominal compartment syndrome", Ostomy Wound Manage., 51(2A suppl):29S-35S (Feb. 2005).

Mendez-Eastman, S., "Determining the appropriateness of negative pressure wound therapy for pressure ulcers", Ostomy Wound Manage., 50(4A suppl):13-16 (Apr. 2004).

Mendez-Eastman, S., "Using negative-pressure for positive results", Nursing, 35(5):48-50 (May 2005).

Miller, M.S., et al., "Negative pressure wound therapy: 'a rose by any other name'", Ostomy Wound Manage., 51 (3):44-9 (11 sheets) (Mar. 2005).

Niezgoda, J.A., et al., "The economic value of negative pressure wound therapy", Ostomy Wound Manage., 51 (2A suppl):44S-47S (Feb. 2005).

Niezgoda, J.A., "Combining negative pressure wound therapy with other wound management modalities", Ostomy Wound Manage., 51(2A suppl):S36-8 (Feb. 2005).

Orgill, D.P., et al., "Guidelines for treatment of complex chest wounds with negative pressure wound therapy", Supplement B to Wounds: A Compendium of Clinical Research and Practice, (24 sheets) (Dec. 2004).

Orgill, D.P., "Utilizing negative pressure wound therapy on open chest/sternotomy wounds", Ostomy Wound Manage., 50(11A suppl):15S-17S (Nov. 2004).

Orgill, D.P., "Advancing the treatment options of chest wounds with negative pressure wound therapy", Ostomy Wound Manage., 51(2A suppl):39S-43S (Feb. 2005).

Page, J.C., et al., "Retrospective analysis of negative pressure wound therapy in open foot wounds with significant soft tissue defects", Adv. Skin Wound Care, 17(7):354, 356, 358-60, 362-64 (Sep. 2004).

Page, J.C., et al., "Negative pressure wound therapy in open foot wounds with significant soft tissue defects", Ostomy Wound Manage., 51(2A suppl):9S-14S (Feb. 2005); excerpted from Page, J.C., et al., "Retrospective analysis of negative pressure wound therapy in open foot wounds with significant soft tissue defects", Adv. Skin & Wound Care, 17(7):354-364, (2004).

Pattison, P.S., et al., "Case report: Using dual therapies—Negative pressure wound therapy and modified silicone gel liner—to treat a limb postamputation and dehiscence", Wounds, 17(8):233-40 (11 sheets) (Aug. 2005).

Ratliff, C.R., "Negative-pressure wound therapy. Adjunct relief for chronic wounds", Adv. Nurs. Pract., 12(7):47-9 (3 sheets) (Jul. 2004) (Issue date: Jul. 1, 2004).

Sarsam, S.E., et al., "Management of wound complications from cesarean delivery," Obstet. Gynecol. Surv., 60 (7):462-73 (Jul. 2005).

Schaum, K.D., "Payment perspective: Negative pressure wound therapy pumps and ostomy supplies", Ostomy Wound Manage., 51(3):20-22 (2 sheets) (Mar. 2005).

Simman, R., et al., "A comparative histological study of skin graft take with tie-over bolster dressing versus negative pressure wound therapy in a pig model: a preliminary study [brief communication]", Wounds, 16(2):76-80 (7 sheets) (Feb. 2004).

Avery, C., et al., "Negative pressure wound dressing of the radial forearm donor site", International Journal of Oral Maxillofacial Surgery, 2000; 29, pp. 198-200.

Armstrong, David G., et al., "Outcomes of Subatmospheric Pressure Dressing Therapy on Wounds of the Diabetic Foot", Ostomy/Wound Management 2002; 48(4): 64-68.

Brown, Karen M., et al., "Vacuum-Assisted Closure in the Treatment of a 9-Year-Old Child with Severe and Multiple Dog Bite Injuries of the Thorax", Society of Thoracic Surgeons, 2001; 72:1409-1410.

Catarino, Pedro A., et al., "High-Pressure Suction Drainage via a Polyurethane Foam in the Management of Poststernotomy Mediastinitis", Ann Thorac Surg 2000; 70:1891-5.

Mendez-Eastman, Susan, RN, CPSN, CWCN, Clinical Management Extra, Guidelines for Using Negative Pressure Wound Therapy, Advances in Skin & Wound Care, Nov./Dec. 2001, vol. 14, No. 6, p. 314-322.

Cooper, Susan Mary, "Topical negative pressure in the treatment of pressure ulcers", Letters posted in the Journal of the American Acad of Dermatology, August, Part 1, 1999, p. 280.

de la Torre, Jorge I., MD, et al., "Healing a Wound with an Exposed Herrington Road: A Case Study", Ostomy Wound Management, pp. 18-19, May 2002, vol. 48, Issue 5.

de Lange, M.Y., et al., "Vacuum-assisted closure: indications and clinical experience", Eur J Plast Surg (2000) 23:178-182.

Deva, Anand, K., et al., "Topical negative pressure in wound management", MJA, Vo. 173, pp. 128-131, Aug. 7, 2000.

Elwood, Eric T., et al., "Negative-Pressure Dressings in the Treatment of Hidradenitis Suppurativa", Ann Plast Surgery Jan. 2001; 46:49-51.

Evans, D. and Land, L., "Topical negative pressure for treating chronic wounds: a systematic review", British Journal of Plastic Surgery (2001), 54, 238-242.

Fabian, Thaddeus S., MD, "The Evaluation of Subatmospheric Pressure and Hyperbaric Oxygen in Ischemic Full-Thickness Wound Healing", The American Surgeon, Dec. 2000, vol. 66, 1136-1143.

Fenn, C.H. and Butler, P.E.M., "Abdominoplasty wound-healing complications: assisted closure using foam suction dressing", British Journal of Plastic Surgery (2001), 54, 348-351.

Giovannini, Uberto M., MD, "Negative Pressure for the Management of an Exposed Vascular Dacron Polyester Patch", Annals of Plastic Surgery, 47(5): 577-578, 2001.

Gustafsson, Ronny, MD, "Vacuum-assisted closure therapy guided by C-reactive protein level in patients with deep sternal wound infection", The Journal of Thoracic and Cardiovascular Surgery, vol. 123, No. 5, pp. 895-900, May 2002.

Gwan-Nulla, Daniel N., MD and Casal, Rolando S., MD, "Toxic Shock Syndrome Associated with the Use of the Vacuum-Assisted Closure Device", Ann Plastic Surgery 2001;47:552-554.

Hersh, Robert E., MD, et al., "The Vacuum-Assisted Closure Device as a Bridge to Sternal Wound Closure", Ann Plast Surg. 2001; 46: 250-254.

Heugel, Judson R., et al., "Treatment of the Exposed Achilles Tendon Using Negative Pressure Wound Therapy: A Case Report", Journal of Burn Care and Rehabilitation, May/Jun. 2002, vol. 23, No. 3, pp. 167-171.

Joseph, Emmanuella, MD, et al., "A Prospective Randomized Trial of Vacuum-Assisted Closure Versus Standard Therapy of Chronic Nonhealing Wounds", Wounds 2000: 12(3): 60-67.

Josty, I.C., et al., "Vacuum-assisted closure: an alternative strategy in the management of degloving injuries of the foot", British Journal of Plastic Surgery (2001), 54, pp. 363-365.

Kovacs, Laszlo H., MD, "Necrotizing Fasciitis", Annals of Plastic Surgery, vol. 47, No. 6, Dec. 2001, pp. 680-682.

Scheufler, O., et al., "Problem-adapted application of vacuum occlusion dressings: case report and clinical experience", Eur J. Plast Surg (2000) 23: 386-390.

Sposato, G., et al., "Ambulant vacuum-assisted closure of skin-graft dressing in the lower limbs using a portable mini-VAC device", British Journal of Plastic Surgery (2001), 54, 235-237.

Tang, Augustine T.M., et al., "Novel application of vacuum assisted closure technique to the treatment of sternotomy wound infection", European Journal of Cardio-Thoracic Surgery 17 (2000) 482-484.

Wu, S.H., et al., "Vacuum therapy as an intermediate phase in wound closure: a clinical experience", Eur J Surg (2000) 23:174-177.

Zhivotaev VM. Vacuum therapy of postoperative infected wounds of the urinary bladder, Klinicheskaia Khiurgiia. 1970;5:36-39. (in Russian) (and 1 sheet printout from PubMed).

EP 0 620 720 (DE 692 24 847), English translation of the Decision of the Federal Patent Court dated Mar. 17, 2009, full translation by Vossius & Partner.

Excerpts from Bier's Hyperemic Treatment, pp. 17-25, 44-46, 90-96, 167-170, 210-211 (1909).

EP 03756228.7 Supplemental European Search Report (May 26, 2009).

WFU & KCI v. S&N, VID 143, (Regarding AU 674837) Federal Court of Australia, Order by Judge Ryan, including reasons for judgment, dated Jun. 15, 2009.

Solovev, V.A., "Treatment and prevention of suture failures after gastric resection," Dissertation abstract, with alleged index card, S.M. Kirov Gorky State Medical Institute, Gorky, U.S.S.R., (Exhibit I of Third party comments) (1988).

Solovev, V.A., "The method of treatment of immature external fistulas in the upper gastrointestinal tract," S.M. Kirov Gorky State Medical Institute, Gorky, U.S.S.R., (Exhibit J of Third party comments) (1987).

EP 0 620 720 (DE 692 24 847), Decision of Federal Patent Court, in German with English translation, dated Mar. 17, 2009.

Conquest, A.M., et al., "Hemodynamic effects of the vacuum-assisted closure device on open mediastinal wounds," J. Surg. Res., 115(2):209-13 (Dec. 2003).

Copson, D., "Topical negative pressure and necrotising fasciitis", Nurs. Stand., 18(6):71-2, 74, 76, 78, 80 (Oct. 22, 2003).

Demaria, R.G., et al., "Topical negative pressure therapy. A very useful new method to treat severe infected vascular approaches in the groin,"J. Cardiovascular Surg., 44(6):757-61 (Dec. 2003).

DeVooght, A., et al., "Vacuum-assisted closure for abdominal wound dehiscence with prosthesis exposure in hernia surgery," Plast. Recontr. Surg., 112(4):1188-9 (Sep. 15, 2003).

Duxbury, M.S., et al., "Use of a vacuum assisted closure device in pilonidal disease,"J. Wound Care, 12(9):355 (Oct. 2003).

Eldad, A., et al., "Vacuum—A novel method for treating chronic wounds", Harefuah, (English abstract on last 2 pp. and 1 sheet printout from PubMed); 142(12):834-6, 878, 877 (Dec. 2003).

Evans, D., et al., "Topical negative pressure for treating chronic wounds", Cochrane Database Syst. Rev., vol. (3), accession No. 00075320-100000000-01309 (2005).

Fuchs, U., et al., "Clinical outcome of patients with deep sternal wound infection managed by vacuum-assisted closure compared to conventional therapy with open packaging: a retrospective analysis", Ann. Thorac. Surg., 79:526-31 (2005).

Gustafsson, R.I., et al., "Deep sternal wound infection: a sternal-sparing technique with vacuum-assisted closure therapy" Ann. Thorac. Surg., 76(6):2048-53 (Dec. 2003).

Herscovici Jr., D., et al., "Vacuum-assisted wound closure (VAC therapy) for the management of patients with high-energy soft tissue injuries", J. Orthop. Trauma, 17(10):683-8 (Nov.-Dec. 2003).

Huang, J., et al., "Treatment of open fracture by vacuum sealing technique and internal fixation", Zhongguo Xiu Fu Chong Jian Wai Ke Za Zhi, (English abstract on first page and 2 sheets printout from PubMed); 17(6):456-8 (Nov. 2003).

Jones, E.G., et al., "Management of an ileostomy and mucous fistula located in a dehisced wound in a patient with morbid obesity", J. Wound Ostomy Continence Nurs., 30(6):351-356 (Nov. 2003).

Langley-Hawthorne, C., "Economics of negative pressure wound therapy", Ostomy Wound Manage., 50(4A suppl):35, 36, C3 (Apr. 2004).

Neubauer, G., et al., "The cost-effectiveness of topical negative pressure versus other wound-healing therapies", J. Wound Care, 12(10):392-3 (Nov. 2003).

Orgill, D.P., et al., "Functional reconstruction following electrical injury", Ann. N.Y. Acad. Sci., 888:96-104 (Oct. 30, 1999).

Salameh, J.R., et al., "Laparoscopic harvest of omental flaps for reconstruction of complex mediastinal wounds", JSLS, 7(4):317-22 (Oct.-Dec. 2003).

Shoufani, A., et al., "Vacuum assisted closure—a new method for wound control and treatment", Harefuah, (English abstract on last page; 1 sheet printout from PubMed); 142(12):837-40, 877 (Dec. 2003).

Shvartsman, H.S., et al., "Use of vacuum-assisted closure device in the treatment of recurrent Paget's disease of the vulva", Obstet. Gynecol., Supplement, 102(5, part 2):1163-6 (Nov. 2003).

Sibbald, R.G., et al., "A consensus report on the use of vacuum-assisted closure in chronic, difficult-to-heal wounds", Ostomy Wound Manage., 49(11):52-66 (Nov. 2003).

Wagner, S., et al., "Comparison of inflammatory and systemic sources of growth factors in acute and chronic human wounds", Wound Rep. Reg., 11:253-260 (Jul.-Aug. 2003).

Wild, T., "Consensus of the German and Austrian Societies for wound healing and wound management on vacuum closure and the VAC treatment unit", MMW Fortschr. Med., (English abstract on p. 100; 1 sheet printout from PubMed); 145 Suppl. 3:97-101 (Oct. 9, 2003).

Chen, S.Z., et al., "Effect of vacuum-assisted closure on the expression of proto-oncogenes and its significance during wound healing", Zhonghua Zheng Xing Wai Ke Za Zhi, (English abstract on first page, 2 sheets printout from PubMed); 21:197-200 (May 2005).

Immer, F.F., et al., "Deep sternal wound infection after cardiac surgery: modality of treatment and outcome", Ann. Thorac. Surg., 80(3):957-61 (Sep. 2005; available online Aug. 23, 2005).

Saltzman, C.L., "Salvage of diffuse ankle osteomyelitis by single-stage resection and circumferential frame compression arthrodesis", Iowa Orthop. J., 25:47-52 (2005).

Bogart, L., "A summary of posters presented at the symposium on Advanced Wound Care: 2003 and 2004", Ostomy Wound Manage., 51(4):88-91 (Apr. 2005).

Chen, S.Z., et al., "Effects of vacuum-assisted closure on wound microcirculation: an experimental study", Asian J. Surg., 28(3):211-7 (Jul. 2005).

Paul, J.C., "Vacuum assisted closure therapy: A must in plastic surgery", Plastic Surg. Nurs., 25(2):61-5 (Apr.-Jun. 2005).

Winter, D., "Perspectives on vacuum-assisted closure therapy in pilonidal sinus surgery", Dis. Colon Rectum, 48 (9):1829-30, (Sep. 2005).

Arca, M.J., et al., "Use of vacuum-assisted closure system in the management of complex wounds in the neonate", Pediatr. Surg. Int., 21(7):532-5, 8 sheets, (published online Jun. 17, 2005).

Adamkova, M., et al., "First experience with the use of vacuum assisted closure in the treatment of skin defects at the burn center", Acta. Chir. Plast., 47(1):24-7 (2005).

Venturi, M.L., et al., "Mechanisms and clinical applications of the vacuum-assisted closure (VAC) device: a review", Am. J. Clin. Dermatol., 6(3):185-94 (2005).

Noel, B., "Management of venous leg ulcers", Rev. Med. Suisse, (English abstract on first page, 1 sheet printout from PubMed); 1(16):1062-6, 1068 (Apr. 20, 2005).

Riccio M. et al., "Delayed microsurgical reconstruction of the extremities for complex soft-tissue injuries", Microsurgery, 25:272-83 (2005).

Sjogren, J., et al., "Clinical outcome after poststernotomy mediastinitis: vacuum-assisted closure versus conventional treatment", Ann. Thorac. Surg., 79(6):2049-55 (Jun. 2005).

Dainty, L.A., et al., "Novel techniques to improve split-thickness skin graft viability during vulvo-vaginal reconstruction", Gynecol. Oncol., 97(3):949-52 (Jun. 2005).

Clubley, L., et al., "Using negative pressure therapy for healing of a sternal wound", Nurs. Times, 101(16):44-6 (Apr. 19, 2005).

Caniano, D.A., et al., "Wound management with vacuum-assisted closure: experience in 51 pediatric patients", J. Pediatr. Surg., 40(1):128-32 (Jan. 2005).

Steenvoorde, P., et al., "Deep infection after ilioinguinal node dissection: vacuum-assisted closure therapy?" Low. Extrem. Wounds, 3(4):223-226 (Dec. 2004).

Ryan, T.J., "Evans (1966) exchange and the skin in the light of vacuum-assisted closure, yoga, and maggots", Low. Extrem. Wounds, 3(3):121-2 (Sep. 2004).

Armstrong, D.G., et al., "Decreasing foot pressures while implementing topical negative pressure (vacuum-assisted closure) therapy", Low. Extrem. Wounds, 3(1):12-15 (Mar. 2004).

Wackenfors, A., et al., "Blood flow responses in the peristernal thoracic wall during vacuum-assisted closure therapy", Ann. Thorac. Surg., 79(5):1724-31 (May 2005).

Whelan, C., et al., "Mechanics of wound healing and importance of vacuum-assisted closure® in urology", J. Urol., 173:1463-70 (May 2005).

O'Connor, J., et al., "Vacuum-assisted closure for the treatment of complex chest wounds", Ann. Thorac. Surg., 79 (4):1196-200 (Apr. 2005).

Nugent, N., et al., "Vacuum-assisted closure—A management option for the burns patients with exposed bone", Burns, 31(3):390-393 (May 2005) (Epub Jan. 22, 2005).

Lambert, K.V., et al., "Vacuum assisted closure: a review of development and current applications", Eur. J. Vasc. Endovasc. Surg., 29(3):219-226 (Mar. 2005).

Smith, N., "The benefits of VAC Therapy in the management of pressure ulcers", Br. J. Nurs., 13(22):1359-60, 1362, 1364-65 (Dec. 9, 2004-Jan. 12, 2005).

White, R.A., et al., "Vacuum-assisted closure complicated by erosion and hemorrhage of the anterior tibial artery", J. Orthop. Trauma, 19(1):56-59 (Jan. 2005).

De Geus, H.R.H., et al., "Vacuum-assisted closure in the treatment of large skin defects due to necrotizing fasciitis", Intensive Care Med., 31(4): 601 (1 page) (Apr. 2005) (Epub Jan. 22, 2005).

Samson, D., et al., "Wound-healing technologies: low level laser and vacuum-assisted closure", Evid. Rep. Technol. Assess. (Summ.), (111):1-6, (Dec. 2004).

Gibson, K., "Vacuum-assisted closure", Am. J. Nurs., 104(12):16 (1 page) (Dec. 2004).

Bagautdinov, N. A., "Variant of external vacuum aspiration in the treatment of purulent disease of soft tissue," pp. 94-96 and Introduction by V.E. Volkov and an opinion by V. V. Shutova dated Feb. 4, 2009, in Russian with English translation, with alleged card catalogue card with English translation, and certification of translation dated Feb. 19, 2009, Current Problems in Modern Clinical Surgery, (1986).

Kuznetsov, V.A., "Vacuum and vacuum-sorption treatment of open septic wounds," in II All-union conference "Wounds and wound infection" "(Abstracts of presentations)" in Russian with English translation, and card with English translation, Moscow, Oct. 28-29, 1986. (Bagautdinov II).

Robson, M.C., et al., Chapter 10 "Wounds and wound healing," p. 107-114 in Essentials of General Surgery, P.F. Lawrence ed., Williams & Wilkins, (1988).

Robson, M.C., et al., Chapter 11 "Wounds and wound healing," p. 119-126 in Essentials of General Surgery, 2nd edition, P.F. Lawrence ed., Williams & Wilkins, (1992).

Smith, D.J. Jr., et al., Chapter 7 "Wounds and wound healing," p. 113-122 in Essentials of General Surgery, 3d edition, P.F. Lawrence ed., Lippincott Williams & Wilkins, (2000).

Talboy, G.E., et al., "Chapter 8: Wounds and wound healing," p. 147-161 in Essentials of General Surgery, B. Sun ed., Lippincott Williams & Wilkins, (2006).

Garrison, R.N., et al., "Chapter 9: Surgical infections," p. 163-179 in Essentials of General Surgery, B. Sun ed., Lippincott Williams & Wilkins, (2006).

Taber'S Cyclopedic Medical Dictionary, Edition 20, pp. 306-309, 728-729, 765, 1726, and 2006-2009. (2005).

Mills, N., Polymer Foams Handbook: engineering and biomechanics applications and design guide, pp. 2-3, (2007).

Bucknall, T.E., et al.. eds., "Sutures and dressings," p. 88-93 in Wound Healing for Surgeons, (1984).

Parker, S.P., ed., McGraw-Hill Dictionary of Scientific and Technical Terms, 5th ed., pp. 139, 533, 772, and 1672 (1994).

Alger, M.S.M., Polymer Science Dictionary, (4 sheets), Elsevier Science Publishers Ltd. (1989).

Stedman's Medical Dictionary, 25th ed., pp. 554, 667-668, and 1603-1604, Williams & Wilkins, (1990).

Webster's New World Dictionary of the American Language, pp. 1105, Simon & Schuster, Inc., (1984).

Transeal transparent wound dressing, DeRoyal, 4 sheets (2003).

Kuznetsov, V.A., "Vacuum and vacuum-sorption treatment of open septic wounds," in II All-union conference "Wounds and wound infections" "(Presentation abstracts)" in Russian with English translation dated Apr. 2, 2009, with table of contents, Moscow, Oct. 28-29, 1986.

British Pharmacopoeia 19, vol. II, p. 927 and p. 548 of 1986 addendum, (vol. II—1980, addendum—1986).

KCI, "The V.A.C. operations summary," 7 sheets, (1999).

Kanshin, N. N., "Closed treatment of suppurative processes by the method of active lavage drainage," Third Surgical Clinic of the N. V. Sklifosovkiy Moscow Scientific Research Institute of Emergency Care, pp. 18-23, (6 sheets in English, 6 sheets in Russian and English abstract on pp. 22-23), allegedly submitted 1979.

Lokhvitskii, S.V., et al., "External vacuum aspiration in the treatment of purulent disorders of the soft tissues," Inpatient Surgery Clinic of the Therapeutic Department at Karagandy Medical Institute, Municipal Hospital No. 1, Temirtau, pp. 130-134 (5 sheets English, 5 sheets Russian), allegedly submitted Sep. 22, 1982.

Ersh, Z.Ya., "Use of polyurethane foam for treating purulent cavities and wounds," Purulent Septic Unit of Hospital No. 35, (2 sheets English and 2 sheets Russian), allegedly submitted for publication Mar. 21, 1984.

3M™ Tegaderm™ Transparent film dressings—wound, Commonly asked questions, 4 sheets, (Jan. 2007).

Greene, A.K., et al., "Microdeformational wound therapy," Ann. Plast. Surg., 56(4):418-422, (2006).

Bui, T.D., et al., "Negative pressure wound therapy with off-the-shelf components," Am. J. Surg., 192:235-237, (2006).

PCT/US08/79364—Written Opinion and International Search Report (Dec. 16, 2008).

Taber's Cyclopedic Medical Dictionary, 16th edition, pp. 613-614, 643, 679, 1444, and 1686-1688, (1989).
Parker, S.P., ed., McGraw-Hill Dictionary of Scientific and Technical Terms, 4th ed., pp. 1462, (1989).
Gove, P.B., ed., Webster's Third New International Dictionary Unabridged, pp. 869 and 2627 (1986).
Stedman's Medical Dictionary, 25th ed., pp. 1739, Williams & Wilkins, (1990).
Kirk-Othmer, Encyclopedia of Chemical Technology, 2nd completely revised edition, vol. 9, pp. 220-232, John Wiley & Sons, Inc., (1966).
British Pharmacopoeia Selections: (1988) vol. II, p. 1126-1127, A223-A224; Addendum 1992, p. 1494; (1993) vol. II, p. 1266, A218-A219.
PCT/US08/30581—Written Opinion and International Search Report (Feb. 20, 2009).
PCT/US03/16763—Written Opinion, International Preliminary Examination Report, and International Search Report, (Dec. 18, 2003, Apr. 19, 2004, and Sep. 2, 2004).
Dunphy, J.E., ed., et al., "Current Surgical Diagnosis & Treatment" 5th ed., pp. 946-951, with 5 additional sheets, Lange Medical Publications, Los Altos, CA (1981).
Wagner, D.R., et al., "Combined parenteral and enteral nutrition in severe trauma," Nutrition in Clinical Practice, 7:113-116 with additional sheet, (1992).
Krizek, T.J., et al., "The use of prophylactic antibacterials in plastic surgery: A 1980s update," Plast. Reconstr. Surg., 76(6): 953-962, (Dec. 1985).
Thomas, S., "Pain and wound management," Community Outlook, pp. 11-13, 15 and one extra sheet, (Jul. 1989).
Livshits, V.S., "Polymer dressings for wounds and burns (review)," All-Union Scientific-Research Institute for Medical Polymers, Moscow, pp. 515-522, (allegedly published in Pharmaceutical Chemical Journal, 22(7):790-798, translated from Russian (allegedly dated Jul. 1988)), Plenum Publishing Corp., (1989).
Calne, S., ed., Position Document: Pain at wound dressings changes, pp. 1-17 and 3 additional sheets, supported by Molnlycke Health Care, (allegedly dated 2002).
Skover, G., et al., "45: New Technologies: An Overview," Chronic Wound Care, pp. 425-430 (allegedly dated 1990).
2 sheets of documents, the citation is alleged to be: David JA, Wound Management: A Comprehensive Guide to Dressing and Healing, pp. 50-53 (allegedly dated 1986).
Thomas, S., "Selecting dresssings," Community Outlook, vol. 6, 4 sheets, (Jun. 1991).
1 sheet document, the citation is alleged to be: David J., Extract from Practical Nursing Handbook: Wound Management: A Comprehensive Guide to Dressing and Healing, pp. 166-167, (allegedly dated 1986).
Orgill, D.P., et al., "The mechanisms of action of vacuum assisted closure: More to learn," Surgery, 146(1):40-51, (Jul. 2009).
Defranzo, A., et al., "4: Vacuum-assisted closure in extremity trauma," in Soft Tissue Surgery, S.L. Moran et al., p. 49-60 and additional sheet, Lippincott Williams & Wilkins (Pub. Apr. 1, 2008).
Stoeckel, W.T., et al., "30: Vacuum assisted devices for difficult wounds of the face and neck," Essential Tissue Healing of the Face and Neck, p. 399-408, and additional sheet, Hom, et al., (Pub. Jan. 28, 2009).
Marks, M.W., et al., "Principles & Applications of Vacuum Assisted Closure (VAC)" Plastic Surgery Secrets, 2nd ed., Mosby Elsevier, (2010).
Cuppone, M., et al., "The longitudinal Young's Modulus of cortical bone in the midshaft of human femur and its correlation with CT scanning data," Calcif. Tissue Int., 74:302-309, (2004).
Thomas, S., "Atraumatic dressings," World Wide Wounds, sponsored by Molnylcke Health Care, 11 sheets, published Jan. 2003, website printout dated Jun. 29, 2009.
Proto, Massachusetts General Hospital Dispaches from the Frontiers of Medicine, 2 sheets, (Winter 2006).
Kumar, A.R., "Standard wound coverage techniques for extremity war injury," J. Am. Acad. Orthop. Surg., 14:S62-S65, (2006).
Ingari, J.V., et al., "Civilian and detainee orthopaedic surgical care at an air force theater hospital," Tech. Hand Upper Extr. Surg., 11(2):130-134, (2007).
Covey, D.C., "Combat orthopaedics: A view from the trenches," J. Am. Acad. Orthop. Surg., 14:S10-S17, (2006).
Andersen, R.C., et al., "Definitive treatment of combat casulties at military medical centers," J. Am. Acad. Orthop. Surg., 14:S24-S31, (2006).
Helgeson, M.D., et al., "Bioartificial dermal substitute: A preliminary report on its use for the management of complex combat-related soft tissue wounds," J. Orthop. Trauma, 21(6):394-399, (Jul. 2007).
Bagautdinov, N. A., "Variant of external vacuum aspiration in the treatment of purulent diseases of soft tissues," Current Problems in Modern Clinical Surgery, Interdepartmental Collection, Cheboksary, pp. 94-96, and library card, in English and Russian, (KCI_Con00220647-59) (1986).
Kuznetsov, V.A., et al., "Vacuum and vacuum-sorption treatment of open purulent wounds," II All-Union Conference "Wounds and Wound Infections" Moscow, pp. 91-92, with library card and table of contents, in English and Russian, (KCI_Con00220660-89) (1986).
Wagner, D. R., et al., "Bioelectrical impedance as a discriminator of pressure ulcer risk," Adv. Wound Care, 9 (2):30-37, (1996).
Mulder, G.D., et al., "Prospective randomized study of the efficacy of hydrogel, hydrocolloid, and saline solution-moistened dressings on the management of pressure ulcers," Wound Rep. Reg., 1:213-218, (1993).
Tintle, T.E., et al., "Early experience with a calcium alginate dressing," Ostomy/Wound Management, pp. 74-81, (May/Jun. 1990).
Jeter, K.F., et al., "Comprehensive wound management with a starch-based copolymer dressing," J. Enterostom. Ther., 13(6):217-225, (Nov.-Dec. 1986).
Winter, G.D., "Formation of the scab and the rate of epithelization of superficial wounds in the skin of the young domestic pig," Nature, No. 4812, p. 293-294 (Jan. 20, 1962).
Robson, M.C., et al., "Bacterial quantification of open wounds," Military Medicine, pp. 19-24, (Jan. 1969).
Jackson, D.M., "The diagnosis of the depth of burning," Br. J. Surgery, 40(164):588-596 and 7 additional sheets, (May 1953).
Gray, A.J., et al., "Small bowel perforation following vacuum suction drainage," J. R. Coll. Surg. Edinb. 30(5):324-5 and additional sheet, (Oct. 1985).
Williams, R.S., "A simple technique for successful primary closure after excision of pilonidal sinus disease," Ann. R. Coll. Surg. England, 72:313-315, (only 2 sheets provided), (1990).
Morykwas, M.J., "38: Vacuum-assisted closure of wounds" in "Wound Healing," A. Falabella et al., eds., Taylor & Francis, NY, pp. 503-515, (2005).
DeFranzo, A.J., et al., "Vacuum assisted closure for the treatment of abdominal wounds," Clin. Plast. Surg. 33(2): 213-224 (Apr. 2006).
Defranzo, A.J., et al., "Vacuum-assisted closure for defects of the abdominal wall," Plast. Reconstr. Surg., 121 (3):832-839, (Mar. 2008).
Zannis, J., et al., "Comparison of fasciotomy wound closures using traditional dressing changes and the Vacuum-Assisted Closure device," Ann. Plast. Surg., 62(4):407-409, (Apr. 2009).
Morykwas, M.J., et al., "Vacuum-assisted closure: state of basic research and physiologic foundation," Plast. Reconstr. Surg., 117(7) (Suppl): 121S-126S, (Jun. 2006).
McGee, M.P., et al., "Swelling and pressure-volume relationships in the dermis measured by osmotic-stress technique," Am. J. Physiol. Regul. Integr. Comp. Physiol., 296:R1907-R1913, (Mar. 25, 2009).
Morykwas, M., "Vacuum assisted closure," 91 sheets of slides, (presented Jun. 20-22, 2007).
Morykwas, M., et al., "El uso de la plantilla de regeneracion integra en la cirugia reconstructiva," 121 sheets of slides (presented Jun. 20-22, 2007).
Morykwas, M., et al., "Aplicaciones de tratamientos con presion sub-atmosferica en el cuidado de quemaduras," 140 sheets of slides (presented Jun. 20-22, 2007).
Peacock, Jr., E.E., Wound Repair, 3d edition, W.B. Saunders Company pp. 12-14, pp. 38-51, Chapter 6 Repair of skin wounds, (1984).
Spartanburg Regional Medical Center Operative reports, 35 sheets, dated 1989.

Johnson, F.E., "Expanded use of suction drains," pp. 469 and 1 sheet of drawings (allegedly dated 1985).
Brossy, J.-J., "Foam elastomer dressings in surgery," SA Medical Journal, 59:559-560, (Apr. 1981).
Groves, A.R., et al., "Silastic foam dressing: an appraisal," Annals of the Royal College of Surgeons of England, vol. 67, pp. 117-118 and additional page, (1985).
Harding, K.G., et al., "Silastic foam dressing for skin graft donor sites—a preliminary report," Br. J. Plast. Surg., 33:418-421, (1980).
Malone, W.D., "Wound dressing adherence: a clinical comparitive study," Archives of Emergency Medicine, 4:101-105, (1987).
Moblvac II advertising materials, 4 sheets, allegedly dated 1984.
Bucknall, T.E. ed., et al., "Wound healing for surgeons," Introduction, Chapter 1 The healing wound, Chapter 2 Wound strength, Chapter 3 Factors affecting healing, Chapter 4 Sutures and dressings, Chapter 5 Clinical trials, Chapter 6 Skin healing and burns, and Chapter 7 The abdominal wall, (1984).
Brubacher, L.L., "To heal a draining wound," RN, 45(3):30-36 (Mar. 1982).
Dahlin, P.A., et al., "Cerebrospinal fluid leak because of pressure sore fistula in a quadriplegic," Spine, 12(1):72-75, (1987).
Downie, P.A., ed., Cash's textbook of medical conditions for physiotherapists, Chapter 1 Inflammation and healing, Chapter 2 Oedema, Chapter 19 Skin conditions, Chapter 20 Burns, B. Lippincott Co., (1979).
Ersh, Z. Ya., "Use of polyurethane foam for cleaning of purulent cavities and wounds," I.I. Grekov J. of Surg., 133 (9):134-135 and additional sheets (10 sheets in English and 5 sheets in Russian) (1984).
Fasol, R, et al., "The foil vacuum dressing for the treatment of infected skin defects," Acta Chir. Austriaca 116-118, (2 sheets English and 3 sheets German) (1976).
"Heparin use may reduce restenosis risk," AORN J., 46(3):456, (Sep. 1987).
Gruendemann, B.J., et al., Alexander's Care of the patient in surgery, 8th ed., C.V. Mosby Co., pp. 138-139 (1987).
Kirk-Othmer Encyclopedia of chemical technology, 3d ed., vol. 8, pp. 201-203 (1979).
Kostyuchenok, B.M., et al., "Vacuum treatment of purulent wounds," Soviet Medicine, pp. 18-21, (4 sheets English, 4 sheets Russian, with English abstract on last page), (1984).
Kuzin, M.I., et al., "Method of vacuum treatment of wounds," Wounds and Wound Infection, pp. 348-350, (2 sheets) (1981).
Kuzin, M.I., ed., et al., "Vacuum treatment of a purulent wound," Wounds and Wound Infection, Handbook for Physicians, 2nd revised and supplemented ed., pp. 243-246, (3 sheets) (1990).
Tranchell, H.G., et al., Circulatory Ulcers a Physical Approach, John Wright & Sons Ltd., Bristol, Foreword, I. Ulcers: a comparison, II. The ulcer, pp. 44-47, and 54-55, (1960).
Parish, L.C., et al., "The infected decubitus ulcer," Int. J. Dermatol., 28:643-647 (Dec. 1989).
Davydov, Y.A., et al., "Device and method for vacuum therapy of purulent lactation mastites," Khirurgiya, (4):131-132, (Apr. 1988).
Davidov, Y.A., et al., "Justifying the usage of forced early secondary sutures in treatment of purulent wounds by the vacuum therapy," Vestnik Chirugia 126-129, (2 sheets in English and 3 sheets in Russian) (Mar. 1990).
Davydov, Y.A., et al., "Pathogenic mechanisms of the effect of vacuum therapy on the course of the wound process," Khirurgiya, 6:42-47 (7 sheets English and 8 sheets Russian, with English abstract on pp. 46-47) (1990).
Davydov, Y.A., et al., "Bacteriological and cytological evaluation of vacuum therapy of purulent wounds", Vestnik khirurgii, 10:48-52, (5 sheets English, 5 sheets Russian, English abstract on pp. 52) (Received 1987).
Davydov, Y.A., et al., "Vacuum therapy in the treatment of purulent lactation mastitis," pp. 66-70 (5 sheets English, 5 sheets Russian, English abstract on pp. 70) (Received 1986).
Davydov, Y.A., et al., "Vacuum therapy in the treatment of acute purulent diseases of soft tissues and purulent wounds", Vest. Khir. 141(9):43-46 (6 sheets English, 6 sheets Russian, English abstract on pp. 46) (1988).

Demorest, R.L., "New standards in water vapour permeability testing," British Plastics & Rubber, 3 sheets, (handwritten label on first sheet shows "Exhibit TT"), (May 1995).
Thomas, S., "Wound Management and Dressings," The Pharmaceutical Press, London, 223 sheets, (1990).
Wood, R.A.B., et al., "A new method for treatment of open granulating wounds," Surgical Dressings in the Hospital Environment, T.D. Turner, ed., et al., Surgical Dressings Research Unit, Welsh School of Pharmacy, Uwist, Cardiff, 8 sheets, (1975).
Turner, T.D., ed., et al., Advances in Wound Management, including "The role of foam dressings in wound management" by S. Thomas, "Clinical aspects of Synthaderm®" by T. Martin, et al., "Lyofoam®—Used in the treatment of leg ulcers" by J. Creevy, and "Clinical experience of Silastic® foam dressing," by K.G. Harding; John Wiley & Sons, 17 sheets, (Proceedings dated Mar. 20-21, 1985) (1986).
*KCI et al.* v. *Blue Sky Medical Group et al.*, Case No. 2007-1340, -1341, -1342, Federal Circuit Decision dated Feb. 2, 2009.
Kuznetsov, V.A., et al., Report on Practical Application entitled "Method of vacuum-sorption treatment of purulent wounds," Kazan Municipal Hospital No. 8, (1 sheet in English, 1 sheet in Russian and certificate of translation dated Apr. 28, 2009), (allegedly dated May 19, 1986).
*WFU* v. *S&N (UK)* Case No. HC08 C03563, Approved judgment dated Jul. 31, 2009.
British Pharmacopoeia, vol. II, pp. 903-940, London (1980).
British Pharmacopoeia 1980, pp. A81, 542, 546-549, with annotations, London—Addendum (1986).
Banwell, P.E., et al., "Application of topical sub-atmospheric pressure modulates inflammatory cell extravasation in experimental partial thickness burns", Wound Repair and Regen., 7(4):A286-A287 (Jul./Aug. 1999).
Morykwas, M.J., et al., "Use of the V.A.C.™ for treatment of a traumatic left hip disarticulation", Acta Chir. Austriaca, Supplement No. 150, pp. 24-25 and cover sheet (1998).
3M™ Inzisionsfolien—Produktubersicht, by 3M Medica, 6 annotated sheets.
Application for rationalization proposal, proposal entitled "Variant for vacuum treatment of purulent wounds," (4 sheets in English, 4 sheets in Russian, certificate of translation dated May 8, 2009), proposal allegedly executed Dec. 25, 1985 (Bagautdinov III).
Buschbaum, H.J., ed., et al., Strategies in Gynecologic Surgery, pp. 203, Springer-Verlag, NY, (1986).
Flynn, J-B. McC., et al., Technological Foundations in Nursing, pp. 506-507, Appleton & Lange, Norwalk, CT, (1990).
GOMCO Mobile constant and intermittent model 6030 & 6031, Operation, Maintenance and Service Manual, with annotations, 21 sheets, (Jan. 1987).
Kahlson, G., et al., "Wound healing as dependent on rate of histamine formation," The Lancet, pp. 230-234, (Jul. 30, 1960).
Karev, I.D., et al., "Foam drainage system for treating purulent wounds," pp. 87-88, (2 sheets English translation, 2 sheets Russian and certifcation of translation dated Apr. 6, 2009) (allegedly dated 1986).
Kozier, B., et al., Techniques in Clinical Nursing, 3d ed., pp. 559-560, pp. 603-605, Addison-Wesley Publishing Company, Inc., Health Sciences, Redwood City, CA, (1989).
McLean, W. C., "The role of closed wound negative pressure suction in radial surgical procedures of the head and neck," The Laryngoscope, 74(1)70-94, (Jan. 1964).
Norton, B.A., et al., Skills for Professional Nursing Practice: communication, physical appraisal, and clinical techniques, pp. 298-302, pp. 328-329, Appleton-Century-Crofts, Norwalk, CT (1986).
Bagautdinov, N. A., Report on Practical Application entitled "Variant of vacuum treatment of purulent wounds," Kazan Municipal Hospital No. 8, (1 sheet in English, 1 sheet in Russian and certificate of translation dated May 8, 2009), (allegedly dated Dec. 24, 1985). (Practical Report I).
Kuznetsov, V.A. et al., Report on Practical Application entitled "Method of vacuum-sorption treatment of purulent wounds," Kazan Municipal Hospital No. 8, (1 sheet in English, 1 sheet in Russian and certificate of translation dated Apr. 28, 2009) (allegedly dated May 19, 1986). (Practical Report II).

Bagautdinov, N. A., Report on Practical Application entitled "Method of vacuum treatment of open purulent wounds," Medical-Sanitary Ward of the Arzamas Instrument Plant, (1 sheet in English, 1 sheet in Russian and certificate of translation dated Apr. 27, 2009) (allegedly dated 1986).(Practical Report III).

Roth, B., et al., "Ubersichtsarbeit: Indication for suction-rinse drainage and hygienic certainty in drainages," GMS Krankenhaushyg. Interdiszip, 1(1):Doc27 (7 sheets in German with English abstract on first sheet) (2006).

Schneider, F.R., Handbook for the Orthopaedic Assistant, 2nd ed., pp. 185, The C.V. Mosby Company, St. Louis, (1976).

Thomas, S., Wound Management and Dressings, Chapter 4: Semipermeable film dressings (continued onto pp. 26-34), Chapter 5: Foam dressings (continued onto pp. 36-42), and pp. 166, The Pharmaceutical Press, London, (1990).

Witkowski, J.A., et al., "Synthetic dressings: wound healing in the 80's," (5 sheets), Hospital Therapy, (Nov. 1986).

Slides and photographs of patient treatment, 19 sheets, (Exhibit D-152) (allegedly dated 1987).

Slides, drawings, photographs of patient treatment and presentation slides, 20 sheets, (Exhibit D-151) (allegedly dated 1987).

Photographs of wound coverings and patient treatment, 16 sheets, (Exhibit D-240) (allegedly dated 1989).

Document "Ex. 5" from deposition of D. Tumey, (dated Mar. 1990).

Letter from Charles C. Valauskas to Mr. Richard Weston regarding: Argenta "Wound Treatment" Patent Evaluation, 15 pp., (Exhibit D-388) (dated Jan. 25, 2002).

Letter to Mr. Urs Tanner from Michael Baniak regarding: Updated Opinion of Non-infringement and Invalidity of Zamierowski U.S. Patent 4,969,880 and Argenta U.S. Patent 5,636,643, 30 pp., (Exhibit D-140) (dated Aug. 23, 2004).

KCI v. BlueSky, Order denying defendant BlueSky's motion for new trial, dated Apr. 4, 2007.

KCI v. BlueSky, Order denying plaintiff's motion for new trial or judgment as a matter of law, dated Apr. 4, 2007.

KCI v. BlueSky, Order denying defendant Medela's renewed motion for judgment as a matter or law, or, alternatively, a new trial on patent invalidity and defendant BlueSky's motion for new trial, dated Apr. 4, 2007.

KCI v. BlueSky, Order denying defendant Medela's motion for new trial on unenforceability and defendant BlueSky's motion for new trial, dated Apr. 4, 2007.

KCI v. BlueSky, Order denying plaintiff's rule 60(b) motion for new trial, dated Apr. 4, 2007.

KCI v. BlueSky, Final Judgment, dated Apr. 4, 2007.

Mulder, G. D. et al. (eds.), Clinicians' Pocket Guide to Chronic Wound Repair, (Spartanburg, SC: Wound Healing Publications), pp. 54-55 (1992 or earlier).

Olenius, M., et al., "Mitotic activity in expanded human skin", Plast. Reconstr. Surg., 91:213-216 (Feb. 1993).

Park, G.B., et al., "The design and evaluation of a burn wound covering", Engineering in Medicine, 7:11-15 (1978).

Pleupump MK II, printouts from websites, www.xenamedical.se and www.landstinget.sormland.se, (12 pp.) (Aug. 14, 2001).

Ramnarine, I.R., et al., "Vacuum-assisted closure in the paediatric patient with post-cardiotomy mediastinitis", Eur. J. Cardiothorac. Surg., 22:1029-31 (Dec. 2002).

Rollins, H., "Hypergranulation tissue at gastrostomy sites", J. Wound Care, 9(3):127-129 (Mar. 2000).

Schaum, K.D., "Medicare Part B negative pressure wound therapy pump policy. A partner for Medicare Part A PPS," Home Healthc. Nurse, 20(1):57-8 (Jan. 2002).

Shaer, W.D., "Inexpensive vacuum-assisted closure employing a conventional disposable closed-suction drainage system", Plast. Reconstr. Surg., 107(1):292-3 (Jan. 2001).

Saklani, A.P., et al., "Vacuum assisted closure system in the management of enterocutaneous fistula", Postgrad. Med. J., 78(925):699 (Nov. 2002).

Smith, S.R.G., "Surgical drainage", Br. J. Hosp. Med., 33(6):308-315 (Jun. 1985).

Svedman, P., "A dressing allowing continuous treatment of a biosurface," IRCS Medical Science: Biomedical Technology; Clinical Medicine; Surgery and Transplantation, 7:221 (1979), with annotations.

Svedman, P., et al., "Irrigation treatment in split-thickness skin grafting of intractable leg ulcers", Scand. J. Plast. Reconstr. Surg., 19:211-213 (1985).

Taber's Cyclopedic Medical Dictionary, Edition 18, pp. 937, 942 and 1375.

Takei, T., et al., "Molecular basis for tissue expansion: clinical implications for the surgeon", Plast. Reconstr. Surg., 102(1):247-258 (Jul. 1998).

Tang, A.T.M., et al., "Vacuum-assisted closure to treat deep sternal wound infection following cardiac surgery", J. Wound Care, 9(5):229-30 (May 2000).

Nikkhah, C., et al., "Re: use of specialized bone screws for intermaxillary fixation", Ann. Plast. Surg., 47(1): 93, (Jul. 2001).

Viljanto, J., "A new method for treatment of open wounds", Ann. Chir. Gynaecol. Fenn., (English abstract on first page, and 1 sheet printout from PubMed); 60:94-100 (1972).

Voinchet, V., et al., "Vacuum assisted closure. Wound healing by negative pressure", Ann. Chir. Plast. Esthet., (English abstract on first page, and 1 sheet printout from PubMed); 41(5):583-9, (Oct. 1996).

Volkov, L.A., "Use of vacuum-drainage system in surgical practice", Klin. Khir., (with 2 sheets English translation and 1 sheet printout from PubMed); 7:54-5 (Jul. 1973).

Von Gossler, C.M., et al., "Rapid aggressive soft-tissue necrosis after beetle bite can be treated by radical necrectomy and vacuum suction-assisted closure", J. Cutan. Med. Surg., 4(4):219-222 (Oct. 2000).

Webster's New Universal Unabridged Dictionary Deluxe Second Edition, p. 631.

Wilhelmi, B.J., et al., "Creep vs. stretch: a review of the viscoelastic properties of skin", Ann. Plast. Surg., 41 (2):215-219, (Aug. 1998).

Wiseman, J., et al., "Aesthetic aspects of neurofibromatosis reconstruction with the vacuum-assisted closure system", Aesth. Plast. Surg., 25:326-31 (Sep.-Oct. 2001).

Young, T., "Common problems in wound care: overgranulation", Br. J. Nursing, 4(3):169-170, (Feb. 9-22, 1995).

Yusupov, Y.N., et al., "Active drainage of wounds", Vestn. Khir. Im. I.I. Grek., (with English abstract on last page, 5 sheets of English translation, 3 pp. of English translation by BlueSky publishing and 1 sheet printout from PubMed); 138(4):42-46 (Apr. 1987).

Ziegler, U.E., et al., "Skin substitutes in chronic wounds", Zentralbl. Chir., (English abstract on first page; 1 sheet printout from PubMed); 126 Suppl 1:71-4 (2001).

Werner, H.P., "Goals, risks and complications of wound drainage", included in "Wound drainage in elective and emergency surgery: Abdominal surgery—Vascular surgery—Surgery of the extremities", Wolfgang Pabst Verlag, Zumtobel, V., et al., (eds.), (and 15 sheets of English translation); article appears on pp. 9-16 (1991).

Nelson, R.P., et al., "Use of negative pressure suction in urology", Urology, 4(5):574-576, (Nov. 1974).

Stannard, J., "Complex orthopaedic wounds: prevention and treatment with negative pressure wound therapy", Orthop. Nurs., 23 Suppl 1:3-10 (10 sheets) (Mar.-Apr. 2004), presented at the 17th Annual Clinical Symposium on Advances in Skin & Wound Care, Dallas, TX (Sep. 23, 2002).

Patel, C.T.C., et al., "Vacuum-assisted wound closure: changing atmospheric pressure assists wound healing," AJN, 100:45-47 (2000).

Stewart, M.F., et al., "Cleaning v. healing," Community Outlook, pp. 22, 24 & 26 (Aug. 14, 1985).

Masters, J., "Reliable, inexpensive and simple suction dressings", Letters to the Editor, p. 267, labeled 1998.

Zelko, J.R., et al., "Primary closure of the contaminated wound; closed suction wound catheter", Am. J. Surgery, 142:704-706, (Dec. 1981).

Miller, S.J., "Surgical wound drainage system using silicone tubing", J. Am. Podiatry Assn., 71(6): pp. 287-289 submitted, (Jun. 1981).

Geronemus, R.G., et al., "The effect of two new dressings on epidermal wound healing", J. Dermatol. Surg. Oncol., 8(10):850-852 (Oct. 1982).

Miller, S.H., et al., "An inexpensive wound suction device", Surg. Gyencol. Obstet., 141(5):768 (Nov. 1975).

Trammell, T.R., et al., "Closed-wound drainage systems: the Solcotrans Plus versus the Stryker-CBC ConstaVAC", Orthopaedic Review, 20(6):536-542 (Jun. 1991).

Woodley, D.T., et al., "A double-blind comparison of adhesive bandages with the use of uniform suction blister wounds", Arch. Dermatol., 128(10):1354, 1357 (Oct. 1992).

Hazelbag, S., et al., "Cytokine profile of cervical cancer cells", Gynecol. Oncol., 83(2):235-243, (Nov. 2001).

Beitz, J.M., et al., "Abdominal wound with enterocutaneous fistula: a case study", J. Wound Ostomy Continence Nurs., 25(2):102-6, (Mar. 1998).

Baxandall, T., "Healing cavity wounds with negative pressure", Elderly Care, 9(1):20, 22 (Feb.-Mar. 1997)

Mckinney, P.E., "Out-of-hospital and interhospital management of crotaline snakebite", Ann. Emerg. Med., 37 (2):168-174, (Feb. 2001).

Leroy, S.C., et al., "Severe penile erosion after use of a vacuum suction device for management of erectile dysfunction in a spinal cord injured patient. Case report", Paraplegia, 32(2):120-123 (Feb. 1994).

Article in Russian, pp. 84-85.

BlueSky Medical, 2 sheets of advertisement, "Finally a choice: introducing the Chariker-Jeter wound drainage kit" and "Can negative pressure be periodic?: introducing the Kremlin® wound drainage kit".

Spahn, J.G., "Soft tissue challenges in the head and neck region," Clinical Seminar Handout, EHOB, (46 pages).

Goodship, A.E., "Cyclical Micromovement and Fracture Healing", The Journal of Bone and Joint Surgery, vol. 78-B, No. 1, Jan. 1996, pp. 166-167.

McGuinness, J.G., et al., "Vacuum-assisted closure of a complex pilonidal sinus", Dis. Colon Rectum, 46(2):274-6 (Feb. 2003).

Mendez-Eastman, S., "Wound therapy", Nurs., 32(5):59-63 and one sheet of quiz (May 2002).

Microtek Heritage, Inc. P.O. Box 2487, Columbus, MS 39704. "Wound-Evac ET", (4 sheets).

Moist Wound Dressings from Physicians Instruction Book for Moist Wound Healing.

Moloney, G.E., "Apposition and drainage of large skin flaps by suction", Austr. N.Z. J. Surg., 26(3):173-179 (Feb. 1957).

Moran, S.G., et al., "Vacuum-assisted complex wound closure with elastic vessel loop augmentation: a novel technique", J. Wound Care, 12(6):212-3 (Jun. 2003).

Moserova, J., "The healing and treatment of skin defects", pp. 103-151, (1989).

Nemoto, H., et al., "Stories from the bedside: purple urine bag syndrome development in ileal conduit", WCET J., 23 (2):31-34 (2003).

OpSite Wound Dressings, "Do your pressure sore dressings shape up to the OpSite standard?", 2 pp. of advertisements.

Paradise Valley Hospital, The Center for Wound Healing and Hyperbaric Medicine, 3 pp. of brochure.

Part III. Resolving Selected Clinical Dilemmas, pp. 17-20.

Pleur-evac, "Adult-Pediatric, Non-Metered", Code Number: A-4000, Control Number: F7961J, 5 sheets.

Pleurx Pleural Catheter, Denver Biomedical, 4 pp. of brochure.

Rabkin, J.M., et al., "Infection and oxygen", in Problem Wounds: The Role of Oxygen, ed. J.C. Davis and T.K. Hunt, pp. 1-15, (1987).

Reid, D.P., "Information on cupping or using suction cups on wounds and for healing purposes", from Chinese Herbal Medicine (2 pp.).

Saechtling, H., "Plastics Handbook", 24th edition, pp. 439, 477, and 3 sheets English translation (1989).

Schaffer, D.B., "Closed suction", Nursing, 27(11):62-64 (Nov. 1997).

Schipper, J., et al., "The preconditioning and prelamination of pedicled and free microvascular anastomised flaps with the technique of vacuum assisted closure", Laryngorhinootologie, (English abstract on first page, and 2 sheets printout from PubMed); 82(6):421-7, (Jun. 2003).

Shi, B., et al., "Effects of vacuum-assisted closure (VAC) on the expressions of MMP-1, 2, 13 in human granulation wound", Zhonghua Zheng Xing Wai Ke Za Zhi, (English abstract on first page and 1 sheet printout from PubMed); 19 (4):279-81 (Jul. 2003).

Silicone from CUI (Cox-Uphoff International), "Flexability", 1 page advertisement.

Silver, F.H., et al., "Mechanobiology of force transduction in dermal tissue", Skin Res. Technol., 9(1):3-23 (Feb. 2003).

Silver, F.H., et al., "Mechanosensing and mechanochemical transduction: how is mechanical energy sensed and converted into chemical energy in an extracellular matrix?" Crit. Rev. Biomed. Eng., 31(4):255-331 (2003).

Skillman, J., et al., "Vacuum assisted closure (VAC) dressing for skin graft application following exenteration of the orbit", Orbit, 22(1):63-5 (Mar. 2003).

smith&nephew website printout, Wound Management, FAQs.

Song, D.H., et al., "Vacuum assisted closure for the treatment of sternal wounds: the bridge between debridement and definitive closure", Plast. Recontr. Surg., 111(1):92-7 (Jan. 2003).

Sparta Instrument Corp., 26602 Corporate Ave., Hayward, CA 94545, "Power Source Multi-Purpose Surgical Aspirator".

Taylor, V., "Meeting the challenge of fistulas & draining wounds", Nursing, 10(6):45-51 (Jun. 1980).

Techno Takatsuki Co., Ltd., 8-16 Hatchonishimachi, Takatsuki City, Osaka, Japan, "HiBlow Air Pump".

Townsend, P.L.G., "The quest for a cheap and painless donor-site dressing", Burns, 2:82-85 (Jan. 1976).

Usage Manual Pleurasug TDR (2 pp. of diagrams with descriptions).

Versatile 1 Wound Vacuum System™ for the Promotion of Wound Healing, Wound Application instructions, 1 page advertisement.

Wanner, M.B., et al., "Vacuum-assisted wound closure for cheaper and more comfortable healing of pressure sores: a prospective study", Scand. J. Plast. Reconstruct. Surg. Hand Surg., 37(1):28-33 (2003).

Weaver, B. "The nursing needs of a patient with a complicated abdominal wound", Prof. Nurse, 18(5):269-73 (Jan. 2003).

Wells Johnson Company, 2045 N. Forbes Blvd., Suite 106, Tucson, AZ, "Suction Tips", 1 sheet.

Wells Johnson Company, 2045 N. Forbes Blvd., Suite 106, Tucson, AZ. "Point 5 Aspirator", Winter, G.D., "Healing of skin wounds and the influence of dressings on the repair process", pp. 46-60 of "Surgical dressings and wound healing: proceedings of a symposium held on Jul. 7-8, 1970 at the University of Bradford," Crosby Lockwood for Bradford University Press, (1971).

Wongworawat, M.D., et al., "Negative pressure dressings as an alternative technique for the treatment of infected wounds", Clin. Orthop. Relat. Res., (414):45-8 (Sep. 2003).

Wooding-Scott, M., et al., "No wound is too big for resourceful nurses", RN, 51(12):22-25 (Marked as Exhibit D-88) (Dec. 1988).

Wooding-Scott® Wound Drainage Kit Contents, Item #500.8888, 1 page.

"Wound Suction. Better Drainage With Fewer Problems", Nursing, 5(10):52-55 (Oct. 1975).

Baker, E.A., et al., "Growth factor profiles in intraperitoneal drainage fluid following colorectal surgery: relationship to wound healing and surgery", Wound Rep. Reg., 11(4):261-267, (Jul.-Aug. 2003).

Photographs showing patient treatment, "sheet 2", (Jeter deposition Exhibit 741) (allegedly dated 1985).

3M™, Tegaderm Family of Transparent Dressings for Chronic Wounds, pp. 1-8, copyright (2002).

Aeros, "Moblvac," "introducing the 'off the wall' vacuum system," Aeros Instruments, Life Support Nursing, 3(1):34-37, Barlin Publishing Ltd. (Jan.-Feb. 1980).

Alexander, J.W., et al., "Clinical evaluation of epigard, a new synthetic substitute for homograft and heterograft skin," J. of Trauma, 13(4):374-383, (Apr. 1973).

Alper, J.C., et al., "Moist wound healing under a vapor permeable membrane", J. Am. Acad. Dermatol., 8 (3):347-353, (Mar. 1983).

Anon., "Standard Test Methods for Water Vapor Transmission of Materials," ASTM International, Designation: E 96/E 96M-05, 11 sheets, (Exhibit D-184) (Jun. 2005).

Argenta, P.A., et al., "Vacuum-assisted closure in the treatment of complex gynecologic wound failures," Obstet Gynecol., 99(3):497-501, (9 sheets) (Mar. 2002).

Author unknown, p. 42, "The Not-So-Bald-Truth" (Sep. 1992).

Austad, E.D., et al., "Tissue expansion: dividend or loan?" Plast. Reconstr. Surg.,78(1):63-67 (Jul. 1986).

Azad, S., et al., "Topical negative pressure may help chronic wound healing," B.M.J., 324:1100 (1 sheet) (May 4, 2002).
Ballard, K., et al., Developments in wound care for difficult to manage wounds, Br. J. Nurs., 9(7): 5 pages.
Ballard, K, et al., "Vacuum-assisted closure," Nurs. Times, 97(35):51-2 (5 sheets) Aug. 30-Sep. 5, 2001.
Ballard, K., et al., "Use of vacuum-assisted closure therapy following foot amputation," Br. J. Nurs., 10(15 Supplement):S6, 8, 11-12 (Aug. 2001).
Banwell, P.E., "Topical negative pressure therapy in wound care," J. Wound Care, 8(2):79-84 (Feb. 1999).
Bartels, C.G., et al., "The vacuum sealing technique. A new approach to cover soft tissue defects, used after the resection of a leiomyosarcoma", (English abstract on 2nd page and 1 page printout from PubMed); Hautarzt, 52 (7):653-7 (Jul. 2001).
Bauer, P., et al., "Possibilities of preliminary treatment of infected soft tissue defects by vacuum sealing and PVA foam", (English abstract on first page and 1 sheet PubMed abstract), Handchir. Mikrochir. Plast. Chir., 30(1):20-3 (Jan. 1998).
Baynham, S.A., et al., "Treating stage IV pressure ulcers with negative pressure therapy: a case report," Ostomy Wound Manage, 45(45(4):23-30, 32, 34-35 (Apr. 1999).
Bertone, A.L., et al., "Management of Exuberant Granulation Tissue", Veterinary Clinic of North America—Equine Practice, 5(3):551-562 (Dec. 1989).
Birchall, L., et al., "Developing a trust-wide centralised approach to the use of TNP", J. Wound Care, 11(8):311-4 (Sep. 2002).
BlueSky Medical "The Versatile One!™", Wound Drainage and More, 1 page advertisement (labeled Spring 2003).
BlueSky Medical Support, printout of webpage www.woundvacuum.com/Standard%20pp./support.htm, pp. 1-3 (Oct. 11, 2005).
BlueSky Medical, "A Leader in Suction Technology—Wound Drainage Experts", printout of entire website, 55 pp., www.blueskymedical.com (Apr. 8, 2003).
BlueSky Medical, Negative Pressure Wound Therapy, Product Catalog, "Finally a choice . . . " 8 pp. (Fall 2005).
Bonnamy, C., et al., "Use of the vacuum-assisted closure system for the treatment of perineal gangrene involving the abdominal wall", Ann. Chir., (English abstract on first page and 1 sheet PubMed abstract) 125(10):982-4 (Dec. 2000).
Borzov, M.V., et al., "Vacuum therapy of some skin diseases", Vestn. Dermatol. Venerol., (English abstract on last page, 10 pp. of English translation, and one sheet from PubMed) 39(8):50-56 (Aug. 1965).
Brody, G.S., "Biological creep", Plast. Reconstr. Surg., 92(6):1202-1203 (Nov. 1993).
Byers, R.M., "Clinical effects of closed suction drainage on wound healing in patients with head and neck cancer", Arch. Otolaryngol., 108:723-6 (Nov. 1982).
Cambell, Penny; Promotional Slide Presentation 27 pp., (dated Oct. 14, 2005).
Campton-Johnston, S., et al., "Infected wound management: advanced technologies, moisture-retentive dressings, and die-hard methods", Crit. Care Nurs. Q, 24(2):64-77 (Aug. 2001).
Carroll, P., "The principles of vacuum and its use in the hospital environment", 2nd ed., Ohmeda, 31 sheets.
Cesany, P., "Suction in the treatment of torpid ulcerations", Rozhl. Chir., (English abstract on p. 409 (5 sheets) and 1 sheet printout from PubMed) 48(9):406-409 (Sep. 1969).
Chariker, M. E. et al. (eds), "Effective management of incisional and cutaneous fistulae with closed suction wound drainage", Contemporary Surg., 34:59-63 (Jun. 1989).
Chariker-Jeter Status Link from the website www.trademark.com/cbi-bin/tmlist, 1 page (Oct. 14, 2005).
Chariker-Jeter Technique Tutorial by Penny E. Campbell, Wound Care Solutions.
Chen, K.D., et al., "Mechanotransduction in response to shear stress", J. Biol. Chem., 274(26):18393-18400, (Jun. 25, 1999).
Chinn, S.D., "Closed wound suction drainage", J. Foot Surg., 24(1):76-81 (Jan.-Feb. 1985).

Clare, M.P., et al., "Experience with the vacuum assisted closure negative pressure technique in the treatment of non-healing diabetic and dysvascular wounds", Foot Ankle Int., 23(10):896-901 (Oct. 2002).
Claxton, M.J., et al., "Healing the diabetic wound and keeping it healed: modalities for the early 21st century", Curr. Diab. Rep., 2(6):510-8 (Dec. 2002).
Coggrave, M., et al., Topical negative pressure for pressure ulcer management, Br. J. Nurs., 11(6 Suppl):S29-31, S33 (Mar. 2002).
Collier, M., "Know how: Vacuum assisted closure (VAC)", Nurs. Times, 93(5):32-3 (Jan. 29-Feb. 4, 1997).
Cooper, S.M., et al., "Topical negative pressure", Int. J. Dermatol., 39(12):896-8 (Dec. 2000).
Cozart, R.F., et al., "The use of controlled subatmospheric pressure to promote wound healing in preparation for split-thickness skin grafting in a fourth degree burn", Tenn. Med., 92(10):382-4 (Oct. 1999).
Cro, C., et al., "Vacuum assisted closure system in the management of enterocutaneous fistulae," Postgrad. Med. J., 78(925):364-5 (Nov. 2002).
De Filippo, R.E., et al., "Stretch and growth: the molecular and physiologic influences of tissue expansion", Plast Reconstr. Surg., 109(7):2450-2462 (Jun. 2002).
Deva, A.K., et al., "Vacuum-assisted closure of a sacral pressure sore", J. Wound Care, 6(7):311-312, (Jul. 1997).
Dunford, C., "Hypergranulation tissue", J. Wound Care, 8(10):506-507 (Nov. 1999).
Dunford, C.E., "Treatment of a wound infection in a patient with mantle cell lymphoma", Br. J. Nurs., 10(16):1058, 1060, 1062, 1064-5 (Sep. 13-26, 2001).
Email dated Jan. 14, 2002 with attachments, including "Report of Meeting with DG Consulting", 5 sheets, (Exhibit D-157) (dated Jan. 10, 2002).
Espensen, E.H., et al., "Use of subatmospheric (VAC) therapy to improve bioengineered tissue grafting in diabetic foot wounds", J. Am. Podiatr. Med. Assoc., 92(7):395-7 (Jul.-Aug. 2002).
Westaby, S., "Treatment of purulent wounds and fistulae with an adhesive wound irrigation device", Ann. R. Coll. Surg., 63(5):353-6 (Sep. 1981).
Fleck, T.M., et al., "The vacuum-assisted closure system for the treatment of deep sternal wound infections after cardiac surgery", Ann. Thorac. Surg., 74(5):1596-600 (Nov. 2002).
Davies , J.W.L, "Synthetic materials for covering burn wounds: Progress towards perfection. Part I. Short term dressing materials", Burns, Nov. 1983;10(2), 94-103.
Barnett, A., et al., "Comparison of Synthetic Adhesive Moisture Vapor Permeable and Fine Mesh Gauze Dressings for Split-Thickness Skin Graft Donor Sites", The American Journal of Surgery, vol. 145, Mar. 1983, pp. 379-381.
James, J.H., et. al., "The use of Opsite, A Vapour Permeable Dressing, on Skin Donor Sites", British Journal of Plastic Surgery (1975), 28, 107-110.
Nahas, L.F., et al., "Use of Semipermeable Polyurethane Membrane for Skin Graft Dressings", Plastic and Reconstructive Surgery, Jun. 1981, pp. 791-792.
Orr, RK, et al., "Early Discharge After Mastectomy. A Safe Way of Diminishing Hospital Cost", Am Surg. Mar. 1987; 53(3) Abstract.
Otolaryngology, Head and Neck Surgery, The C.V. Mosby Company, © 1986, pp. 1716, 1724 and 2521.
Otolaryngology, vol. III, Head and Neck, W.B. Saunders Company, © 1980, pp. 2963.
Lore, Jr., J.M., "An Atlas of Head and Neck Surgery", Second Edition, vol. II, W.B. Saunders Company, Ó 1973.
Dewan, P.A., et al., "An Alternative Approach to Skin Graft Donor Site Dressing", Aust. N.Z. J. Surg. 1986, 56, 509-510.
Wu, Lisa C., et al., "Vacuum-Assisted Closure for the Treatment of Sternal Wounds: The Bridge Between Debridement and Definitive Closure", printout from www.plasticsurgery.org., 3 pages (printout dated Apr. 20, 2005).
Healing of Full Thickness Defects in Swine.
Webster, J.G., "Prevention of Pressure Sores", © IOP Publishing Ltd 1991, The Adam Hilger Series on Biomedical Engineering, pp. 199-223.

Garcia-Velasco, M., et al., "Compression Treatment of Hypertrophic Scars in Burned Children", The Canadian Journal of Surgery, V.21, No. 5, Sep. 1978, pp. 450-452.

Rose, M.P., et al., "The Clinical Use of a Tubular Compression Bandage, Tubigrip, for Burn-Scar Therapy: A Critical Anaylis", Burns (1985) 12, 58-64.

Spurlock, Gareth, "The Management of Open Joint Injuries", Wound Management, Veterinary Clinics of North American Equina Practice, vol. 5, No. 3, Dec. 1989.

Tittel, K., et al., "VariDyne—new standards in postoperative wound drainge", Jahrgang 14 (1988), Nr. 2, April, vol. 14 (1988), No. 2, April., pp. 104-107.

Queen, D., et al., "The preclinical evaluation of the Water Vapour Transmission Rate Through Burn Wound Dressings", Biomaterials 1987 vol. 8, September, pp. 367-371.

Wood, R.A.B., et al., "Foam Elastomer Dressing in the Management of Open Granulating Wounds: Experience with 250 Patients", Br. J. Surg., vol. 64 (1977) , pp. 554-557.

Waymack, J.P., et al., "An Evaulation of Aquaphor Gauze Dressing in Burned Children", Burns (1986) 12, 443-448.

Winter, George D., "Epidermal Wound Healing Under a New Polyurethane Foam Dressing (Lyofoam)", Plastic & Reconstructive Surgery, Nov. 1975, Vo. 56, No. 5, pp. 531-537.

Thomas, S., et al., "Comparative Review of the Properties of Six Semipermeable Film Dressings", The Pharmaceutical Journal, Jun. 18, 1988, pp. 785-789.

Baker, B., "Abundance of Web Sites on Wound Care Management", Family Practice News, Mar. 1, 2000, pp. 52.

Cosker, T., et al., "Choice of Dressing Has a Major Impact on Blistering and Healing Outcomes in Orthopaedic Patients", Journal of Wound Care, Vo. 14, No. 1, Jan. 2005, pp. 27-29.

Proceedings from the 2003 National V.A.C.® Education Conference, supplement to the Apr. 2004 WOUNDS, 40 pages.

Dieu, T., et al., "Too Much Vacuum-Assisted Closure", ANZ J. Surg. 2003; 73: 1057-1060.

Chester, D., et al., "Adverse Alteration of Wound Flora with Topical Negative-Pressure Therapy: A Case Report", British Journal of Plastic Surgery, 2002, pp. 510-511.

Alvarez, A., et al., "Vacuum-Assisted Closure for Cutaneous Gastrointestinal Fistula Management", Gynecologic Oncology, 80, 413-416 (2001).

Nienhuijs, S.W., et al., "Can Topical Negative Pressure Be Used to Control Complex Enterocutaneous Fistulae?", Journal of Wound Care, V. 12, No. 9, Oct. 2003, pp. 343-345.

Orringer, Jay, et al., "Management of Wounds in Patients with Complex Enterocutaneous Fistulas", Surgery, Gynecology & Obstetrics, Jul. 1987, V. 165, pp. 79-80.

Lohman, R., et al., "Discussion: Vacuum Assisted Closure: Microdeformations of Wounds and Cell Proliferation", Plastic and Reconstructive Surgery, Oct. 2004, pp. 1097-1098.

Scherer, L, et al., "The Vacuum Assisted Closure Device: A Method of Securing Skin Grafts and Improving Graft Surival", Arch. Surg., V. 137, Aug. 2002, pp. 930-934.

Miller, P., et al., "Late Fascial Closure in Lieu of Ventral Hernia: The Next Step in Open Abdomen Management", the Journal of TRAUMA Injury, Infection and Critical Care, Nov. 2002, V. 53, N. 5, pp. 843-849.

Betancourt, S., "A Method of Collecting the Effluent From Complicated Fistula of the Small Intestine", 1986, p. 375.

Dorland's Illustrated Medical Dictionary , Twenty-Fifth Edition, 1974, pp. 1112.

Hopf, H., et al., "Adjuncts to preparing wounds for closure Hyperbaric oxygen, growth factors, skin substitutes, negative pressure wound therapy (vacuum-assisted closure)", Foot Ankle Clin N Am 6, 2001, pp. 661-682.

Montgomery, B., "Easy Dressing of Large, Draining Abdominal Wounds Using Moisture Vapor-Permeable Film", pp. 417-418, Techniques for Surgeons, Wiley Medical Publication, © 1985.

Herrmann, L., et al., "The Pavaex (Passive Vascular Exercise) Treatment of Obliterative Arterial Diseases of the Extremeties", The Journal of Medicine, Dec. 1933, pp. 524-529.

Herrmann, L., et al., "Passive Vascular Exercises: Treatment of Peripheral Obliterative Arterial Diseases by Rhythmic Alternation of Environmental Pressure", Archives of Surgery, v. 29, n. 5, Nov. 1934, pp. 697-704.

Sturr, R., Evaluation of Treatment of Peripheral Vascular Disease by Alternating Positive and Negative Pressure, Philadelphia, Archives of Physical Therapy, Sep. 1938, pp. 539-543.

Balin, A., et al., "Oxygen Modulates Growth of Human Cells at Physiologic Partial Pressures", Laboratory for Investigative Dermatology, J. Exp. Med. ©, the Rockefeller University Press, v. 160, Jul. 1984, pp. 152-166.

Saran Resins and Films, "Fresh Thinking". website printout, 6 pages, Jan. 20, 2004.

Baker, B., "Negative-Pressure Therapy Looks Promising", Skin & Allergy News, Feb. 2000, p. 14.

McCallon, S., et al., "Vacuum-Assisted Closure versus Saline-Moistened Gauze in the Healing of Postoperative Diabetic Foot Wounds", Ostomy Wound Management, Aug. 2000, v.46, Issue 8.pp. 28-29, 31-32, 34.

Swearingen, P.L., "The Addison-Wesley Photo-Atlas of Nursing Procedures", 9 pages, © 1984.

Peacock, E.E., Jr., Wound Repair:, Repair of Skin Wounds, 1984, pp. 172-175.

Kohlman, P., et al., "Pouching Procedure to Collect Drainage From Around a Biliary Drainage Catheter", Ostomy/Wound Management, Nov./Dec. 1991, pp. 47-50, V. 37.

Alper, J., "Recent Advances in Moist Wound Healing", Southern Medical Journal, Nov. 1986, pp. 1398-1404, V. 79, N. 11.

Sheppard, M.D., "Sealed drainage of wounds," The Lancet, Jun. 14, 1952, pp. 1174-1176.

Putney, F., "The Use of Continuous Negative Pressure After Laryngectomy and Radical Neck Dissection", Surgery, Gynecology & Obstetrics, Aug. 1956, pp. 244-246.

Engdahl, O., et al., "Quantification of Aspirated Air Volume Reduces Treatment Time in Pneumothorax", Eur Respir J., 1990, 3, pp. 649-652.

Spengler, M., et al., "Performance of Filtered Sump Wound Drainage Tubes", Surgery, Gynecology & Obstetricsq, Mar. 1982, pp. 333-336, vol. 154.

Hallstrom, B., et al., "Postoperative Course After Total Hip Arthroplasty: Wound Drainage Versus No Drainage", Orthopaedic Review, Jul. 1992, pp. 847-851.

Miles, W., et al., "A Method of Performing Abdominoperineal Excision for Carcinoma of the Rectum and of the Terminal Portion of the Pelvic Colon", The Lancet, Dec. 19, 1908, pp. 1812-1813.

Benjamin, P., "Faeculent Peritonitis: A Complication of Vacuum Drainage", Br. J. Surg., 1980, pp. 453-454, vol. 67.

Sagi, A., et al., "Burn Hazard From Cupping—An Ancient Universal Medication Still in Practice", Bums, 1988, pp. 323-325, vol. 14, No. 4.

Agrama, H., et al., "Functional Longevity of Intraperitoneal Drains", The American Journal of Surgery, Sep. 1976, pp. 418-421, vol. 132.

Magee, C., et al., "Potentiation of Wound Infection by Surgical Drains", The American Journal of Surgery, May 1976, pp. 547-549, vol. 131.

Birdsell, D., et al., "The Theoretically Ideal Donor Site Dressing",Annals of Plastic Surgery, Jun. 1979, pp. 535-537, vol. 2, No. 6.

Cruse, P., et al., "A Five-Year Prospective Study of 23,649 Surgical Wounds", Surgical Wounds/Cruse and Foord, Aug. 1973, pp. 206-210, vol. 107.

Aubrey, D., et al., "Treatment of the Perineal Wound After Proctectomy by Intermittent Irrigation", Arch. Surg., Oct. 1984, pp. 1141-1144, vol. 119.

Mayo, C., "The One-Stage Combined Abdominoperineal Resection for Carcinoma of the Rectum, Rectosigmoid and Sigmoid", Surgical Clinics of North America, Aug. 1939, pp. 1011-1019.

Draper, J., "Make the dressing fit the wound", Nursing Times, Oct. 9, 1985, pp. 32-35.

Schumann, D., et al., "Preoperative Measures to Promote Wound Healing", Nursing Clinics of North America, Dec. 1979, pp. 683-699, vol. 14, No. 4.

Besst, J., et al., "Wound Healing—Intraoperative Factors", Nursing Clinics of North America, Dec. 1979, pp. 701-712, vol. 14, No. 4.
Cooper, D., et al., "Postsurgical Nursing Intervention as an Adjunct to Wound Healing", Nursing Clinics of North America, Dec. 1979, pp. 713-726, Nursing Clinics of North America, vol. 14, No. 4.
O'Byrne, C., "Clinical Detection and Management of Postoperative Wound Sepsis", Nursing Clinics of North America, Dec. 1979, pp. 727-741, vol. 14, No. 4.
Keith, C., "Would Management Following Head and Neck Surgery", Nursing Clinics of North America, Dec. 1979, pp. 761-778, vol. 14, No. 4.
Tenta, L., et al., "Suction Drainage of Wounds of the Head and Neck", Surgery, Gynecology. & Obstetrics, Dec. 1989, p. 558, vol. 169.
Firlit, C., et al., "Surgical Wound Drainage: A Simple Device for Collection", journal of Urology, Aug. 1972, pp. 327, vol. 108.
Worth, M., et al., "The Effectiveness of Bacterial Filtration in Vented Wound Drains", Journal of Surgical Research, 1979, pp. 405-407, 27.
Flynn, M., et al., "Promoting Wound Healing: Wound Healing Mechanisms", American Journal of Nursing, Oct. 1982, pp. 1544-1558.
Miles, W., "Technique of the Radical Operation for Cancer of the Rectum", The British Journal of Surgery, 1914-1915, pp. 292-305.
Hilton, P., "Surgical Wound Drainage: A Survey of Practices Among Gynaecologists in the British Isles", British Journal of Obstetrics and Gynaecology, Oct. 1988, pp. 1063-1069, vol. 95.
Milsom, I., et al., "An Evaluation of a Post-Operative Vacuum Drainage System", Current Medical Research and Opinion, 1979, pp. 160-164, vol. 6, No. 2.
Fox, J., et al., "The Use of Drains in Subcutaneous Surgical Procedures", The American Journal of Surgery, Nov. 1976, pp. 673-674, vol. 132.
Hulten, L., et al., "Primary Closure of Perineal Wound After Protocolectomy or Rectal Excision", Acta Chir Scand 137, 1971, pp. 467-469.
Landes, R., "An Improved Suction Device for Draining Wounds", Arch. Surg., May 1972, pp. 707, vol. 104.
Hugh, T., "Abdominal Wound Drainage", The Medical Journal of Australia, May 4, 1987, pp. 505.
Eaglstein, W., et al., "Wound Dressings: Current and Future", Clinical and Experimental Approaches to Dermal and Epidermal Repair; Normal and Chronic Wounds, Progress in Clinical and Biological Research, vol. 365, © 1991 Wiley-Liss, Inc., pp. 257-265.
Bruno, P., "The Nature of Wound Healing", Nursing Clinics of North America, Dec. 1979, pp. 667-682, vol. 14, No. 4.
Bar-El, Y., et al., "Potentially Dangerous Negative Intrapleural Pressures Generated by Ordinary Pleural Drainage Systems", Chest, Feb. 2001, pp. 511-514, vol. 119, No. 2.
Agarwala, S., et al., "Use of Mini-Vacuum Drains in Small Surgical Wounds", Plastic and Reconstructive Surgery, Apr. 1998, pp. 1421-1422, vol. 101, n. 5.
Nasser, A., "The Use of the Mini-Flap Wound Suction Drain in Maxillofacial Surgery", Annals of the Royal College of Surgeons of England, 1986, pp. 151-153, vol. 68.
Lumley, J., et al., "The Physical and bacteriological Properties of Disposable and Non-Disposable Suction Drainage Units in the Laboratory", Br. J. Surg, 1974, pp. 832-837, vol. 61.
Britton, B., et al., "A Comparison Between Disposable and Non-disposable Suction Drainage Units: A Report of a Controlled Trial", Br. J. Surg., 1979, pp. 279-280, vol. 66.
McFarlane, R., "The use of Continuous Suction Under Skin Flaps", British Journal of Plastic Surgery, pp. 77-86 (1958-1959).
Fay, M., "Drainage Systems: Their Role in Wound Healing", AORN Journal, Sep. 1987, pp. 442-455, vol. 46, No. 3.
Orgill, D., "Curent Concepts and Approaches to Would Healing", Critical Care Medicine, Sep. 1988, pp. 899-908, vol. 16, No. 9.
"Making Sense of Wound Drainage", Nursing Times, Jul. 5, 1989, pp. 40-42, vol. 85, No. 27.
Harkiss, K., "Leg Ulcers Cheaper in the Long Run", Community Outlook, Aug. 1985, pp. 19, 21, 22.
Westaby, S. (Editor), "Wound Care No. 43; Which Dressing and Why", Nursing Times Jul. 21, 1982, pp. 41-44.
Cobb, J., "Why Use Drains", The Journal of Bone and Joint Surgery, Nov. 1990, pp. 993-995, vol. 72-B, No. 6.

Silvis, R., et al., "The Use of Continuous Suction Negative Pressure Instead of Pressure Dressing", Annals of Surgery, Aug. 1955, pp. 252-256, vol. 142, No. 2.
Van Way, C., "Prevention of Suction-Induced Gastric Mucosal Damage in Dogs", Gastric Suction, 1987, pp. 774-777, vol. 15, No. 8.
Curtin, L., "Wound Management: Care and Cost—An Overview", Nursing Management, Feb. 1984, pp. 22-25, vol. 15.
Royle, G., et al., "Disposable Drains", Annals of the Royal College of Surgery of England, 1984, 1 page, vol. 66.
Stansby, G., et al., "Vacuum Drainage of Groin Wounds After Vascular Surgery", Br. J. Surg., Oct. 1990, pp. 1194-1195, vol. 77, No. 10.
Edlich, R., et al., "Evaluation of a New, Improved Surgical Drainage System", The American Journal of Surgery, Feb. 1985, pp. 295-298, vol. 149.
Broader, J., et al., "Management of the Pelvic Space After Proctectomy", Br. J. Surg., 1974, pp. 94-97, vol. 61.
Ayoub, M., et al., "A study of cutaneous and intracompartmental limb pressures associated with the combined use of tourniquets and plaster casts", May 1986, pp. 497, vol. 68-B, No. 3.
Cooper, D., "Optimizing Wound Healing: A Practice Within Nursing's Domain", Nursing Clinics of North America, Mar. 1990, pp. 165-180, vol. 25, No. 1.
Hollis, H., et al., "A Practical Approach to Wound Care in Patients With Complex Enterocutaneous Fistulas", Surgery, Gynecology & Obstetrics, Aug. 1985, pp. 178-180, vol. 161.
Fingerhut, A., "Passive vs. Closed Suction Drainage After Perineal Would Closure Following Abdominoperineal Rectal Excision for Carcinoma", Dis Colon Rectum, Sep. 1995, pp. 926-932, vol. 38, No. 9.
Alper, Joseph C., et al., "The In Vitro Response of Fibroblasts to the Fluid that Accumulates Under a Vapor-Permeable Membrane". Journal of Investigative Dermatology, 84:513-515, 1985.
Alper, Joseph C., et al., "Use of the Vapor Permeable Membrane for Cutaneous Ulcers: Details of application and side effects", Journal of the American Academy of Dermatology, vol. 11, No. 5, Part 1, Nov. 1984, pp. 858-866.
Angermeier, Marla C., et al., "Vapor-Permeable Membrane Therapy for Ulcers of Osteomyelitis", J. Dermatol. Surg. Oncol,, 10:5, May 1984, pp. 384-388.
Bourke, et al., "Comparison Between Suction and Corrugated Drainage After Simple Mastectomy: A Report on Controlled Trial", Br. J. Surg., vol. 63, 1976, pp. 67-69.
ConstaVac™ Closed Wound Drainage System, Stryker instruments, 2 pages.
Eaglstein, William H., "Experiences with Biosynthetic Dressings", Journal of the American Academy of Dermatology, vol. 12, No. 2, Part 2, Feb. 1985, pp. 434-440.
Falanga, Vincent, et al., "A Therapeutic Approach to Venous Ulcers", Journal of the American Academy of Dermatology, vol. 14, No. 5, Part 1, May 1986, pp. 777-784.
Friedman, S., et al., "Treatment of Dermabrasion Wounds with a Hydrocolloid Occlusive Dressing", Arch Dermatol, vol. 121, Dec. 1985, pp. 1486-1487.
Friedman, Stephen J., et al., "Management of Leg Ulcers with Hydrocolloid Occlusive Dressing", Arch. Dermatol., vol. 120, Oct. 1984, pp. 1329-1336.
Holland, K.T., et al., "A Comparison of the In Vivo Antibacterial Effects of OpSite, Tegaderm and Ensure dressings", Journal of Hospital Infection, 1985, 6, pp. 299-303.
Jeter, Katherine F., et al., "Wound Dressings of the Nineties: Indications and Contraindications", Clinics in Podiatric Medicine and Surgery, vol. 8, No. 4, Oct. 1991, pp. 799-816.
Katz, Stuart, et al., "Semipermiable Occlusive Dressings", Arch Dermatol., vol. 122, Jan. 1986, pp. 58-62.
Lewis, R.T., "Knitted Polypropylene (Marlex) Mesh in the Repair of Incisional Hernias", The Canadian Journal of Surgery, vol. 27, No. 2, Mar. 1984, pp. 155-157.
Lower Extremity Ulcers, Chapter 9, pp. 47-57.
Microtek Medica, Inc. "The Microtek Complete Closed Wound Drainage System", 6 pages.

Rovee, David T., et al., "Effect of Local Wound Environment on Epidermal Healing", Dept. of Skin Biology, Johnson & Johnson Research, New Brunswick, NJ, pp. 159-167,172-175 (1972).

Satas, Donatas, "Handbook of Pressure-Sensitive Adhesive Technology", Silicone Release Coatings, Van Nostand Reinhold Company, 1982, pp. 384-403.

Turner, T.D., "A Look at Wound Dressings", Health and Social Service Journal, May 4, 1979, pp. 529-531.

Turner, T.D., "Recent Advances in Wound Management Products", pp. 3-6.

Turner, T.D., "Semipermeable Films as Wound Dressings", Welsh School of Phainiacy, University of Wales, Great Britain (Jul. 31, 1984).

Turner, T.D., "The Development of Wound Management Products", Chronic Wound Care, pp. 31-46.

Turner, T.D., et al., "Wound Management Product Selection", Journal of Sterile Services Management, Apr. 1985, pp. 3-6.

Varghese, Mathew C., et al., "Local Environment of Chronic Wounds Under Synthetic Dressings", Arch. Dermatol, vol. 122, Jan. 1986, pp. 52-57.

Viljanto, J., "Cellstic: A Device for Wound Healing Studies in Man. Description of the Method", Journal of Surgical Research, 20, 1976, pp. 115-119.

Wagner, S.A., et al., "An individualized Plastic Intraoral Device for the Collection of Human Parotid Saliva", International Journal of Clinical Pharmacology, Therapy and Toxilogy, Vo. 22, No. 5, 1984, pp. 236-239.

Wilson, John L., et al., "Loss of Blood Volume in Spinal Surgery with Use of Closed Wound Suction: An Experimental Study", Southern Medical Journal, Jul. 1968, pp. 761-763, read before the Section on Orthopaedic and Traumatic Surgery, Southern Medical Association, 61st Annual Meeting, Miami Beach, FL, (Nov. 13-16, 1967).

Parikh, R.S., et al., "Self-adhesive drape (Opsite) for management of leaking abdominal wounds", Indian J. Gastroenterol., 19(4):178-180 (Oct./Dec. 2000).

Miller, S.J., "Surgical wound drainage system using silicone tubing", J. Am. Podiatry Assn., 71(6): pp. 287-296 (Jun. 1981).

Alexis, A.F., et al., "Reassessment of the suction blister model of wound healing: introduction of a new higher pressure device", Int. J. Dermatol., 38(8):613-617 (Aug. 1999).

Gnanaraj, J., "A simple, sterile, low-cost, closed suction drainage system", Trop. Doct., 27(2):104 (Apr. 1997).

Klemm, KW., "Antibiotic bead chains", Clin. Orthop. Rel. Res., (295):63-76 (Oct. 1993).

Pignatti, M., et al., "Mobile-VAC for the treatment of lower limb ulcers", Plast. Reconstr. Surg., 108(6):1837-1838 (Nov. 2001).

Schaum, K.D., "Payment strategies: a new medicare part B wound care policy", Adv. Skin & Wound Care, 14 (5):238-240 (Sep./Oct. 2001).

Feierabend, T.C., et al., "Injuries causing major loss of scalp", Plast. Reconstr. Surg., [Abstract only—1 pp. printout from PubMed], 76(2):189-194 (Aug. 1985).

Svedman, P., "A dressing allowing continuous treatment of a biosurface", IRCS Medical Science: Biomedical Technology, Clinical Medicine; Surgery and Transplantation, 7:221 (Exhibit D-407) (1979).

Meyer, W., et al., "Bier's Hyperemic Treatment", W.B. Saunders & Co., (Exhibit D-246) (1908).

PCT/US07/84962—Written Opinion and International Search Report dated Apr. 18, 2008.

Davydov, Y.A., et al., "Basis of the use of forced early secondary suture in the treatment of suppurative wounds by the vacuum therapy method", Vestn. Khir. Im. I.I. Grek., (6 sheets of English translation, 3 sheets of Russian text, and 1 sheet printout from PubMed); 144(3):126-8 (Mar. 1990).

Davydov, Y.A., et al., "Bacteriological and cytological evaluation of the vacuum therapy of suppurative wounds", Vestn. Khir. Im. I.I. Grek., (10 sheets of English translation and 5 sheets of Russian text pp. 48-52 and English abstract on p. 52 and 1 sheet printout from PubMed); 141(10):48-52 (Oct. 1988).

Davydov, Y.A., et al., "The bacteriological and cytological assessment of vacuum therapy of purulent wounds", Vestnik Khirurgii imeni I.I. Grekova, (1 sheet of title page and pp. 48-52, 5 sheets of Russian text and English abstract on p. 52); 141(10):48-52, (Oct. 1988).

Davydov, Y.A., et al., "Bacteriological and cytological assessment of vacuum therapy of purulent wounds", (7 sheets of translation, pp. 48-52 of Russian text and English abstract on p. 52); 141 (10):48-52 (Oct. 1988).

Davydov, Y.A., et al., "Concepts of clinical-biological control of the wound process in the treatment of suppurative wounds using vacuum therapy", Vestnik Khirurgii imeni I.I. Grekova, (5 pp. of translation and 5 pp. of Russian text and 1 sheet printout from PubMed); 146(2):132-136, (Feb. 1991).

Davydov, Y.A., et al., "Vacuum therapy in the treatment of purulent lactation mastitis", Vestnik Khirurgii Imeni I.I. Grekova, (1 Sheet of Title page and pp. 66-70, 6 sheets of Russian text and English abstract on p. 70); 137 (11):66-70, (Nov. 1986).

Davydov, Y.A., et al., "Vacuum therapy in the treatment of purulent lactation mastitis", (8 sheets of English translation, pp. 66-70 of Russian text, and English abstract on p. 70); 137 (11):66-70, (Nov. 1986).

Davydov, Y.A., et al., "Vacuum therapy in the treatment of suppurative lactation mastitis," Vestn. Khir., (15 pp. of translated material, 1 sheet of Pubmed abstract, 5 sheets of Russian text and English abstract on p. 70, and 1 sheet printout from PubMed); 137 (11):66-70 (Nov. 1986).

Davydov, Y.A., et al., "Vacuum therapy in the treatment of acute purulent diseases of soft tissues and purulent wounds", (4 sheets of Translation, 4 sheets of Russian text and English abstract on p. 46); 141(9):43-46 (Sep. 1988).

Davydov, Y.A., et al., "Vacuum therapy in the treatment of acute suppurative diseases of soft tissues and suppurative wounds," Vestn. Khir., (9 sheets of translation, 4 sheets of Russian text pp. 43-46 and English abstract on p. 46 and 1 sheet printout from PubMed); 141 (9):43-46 (Sep. 1988).

Davydov, Y.A., et al., "Vacuum therapy in treatment of acute purulent diseases of soft tissues and purulent wounds," Vestnik Khirurgii (Surgeon's Herald), No. 9 Medicine Publishers, (5 sheets of translation), (1986).

Davydov, Y.A., et al., "Vacuum therapy in the prevention of postoperative wound infection," Vest. Khir. Im. I.I. Grek., (5 sheets of translation, pp. 91-95 of Russian text, English abstract on p. 95, and 1 sheet printout from PubMed); 147(7-8): 91-95, (Jul.-Aug. 1991).

Davydov, Y.A., et al., "Pathogenic mechanism of the effect of vacuum therapy on the course of the wound pracess," Khirurgiia (Mosk.), (16 sheets of English translation, pp. 42-47 of Russian text and English abstract on pp. 46-47); No. 6:42-47 (Jun. 1990).

Davydov, Y.A., et al., "Wound healing under the conditions of vacuum draining," Khirurgiia (Mosk.) (8 sheets of English translation, pp. 21-26 of Russian text and English abstract on pp. 25-26, and 1 sheet printout fram PubMed); (7-8):21-26, (Jul.-Aug. 1992).

Argenta, L.C., et al., "Vacuum-assisted closure: a new method for wound control and treatment: clinical experience", Ann. Plast. Surg. 38(6):563-577, (Jun. 1997).

Argenta, L.C., et al., "Vacuum-assisted closure: state of clinic art", Plast Reconstr. Surg., 117 (7 Suppl.): 127S-142S (Jun. 2006).

Chung, C.J., et al., "Case review: management of life-threatening sepsis and wound healing in a Klippel-Trenaunay patient using seriai surgical debridements and vacuum-assisted closure", Eur. J. Plast Surg., 26:214-216 (2003).

Dedmond, B.T., et al., "Subatmospheric pressure dressings in the temporary treatment of soft tissue injuries associated with type III open tibial shaft fractures in children", J. Pediatr. Orthop., 26(6):728-732, (Nov.-Dec. 2006).

Dedmond, B.T., et al., "The use of negative-pressure wound therapy (NPWT) in the temporary treatment of soft tissue injuries associated with high-energy open tibial shaft fractures", J. Orthop. Trauma, 21(1):11-17, (Jan. 2007).

DeFranzo, A.J., et al., "The use of vacuum-assisted closure therapy for the treatment of lower-extremity wounds with exposed bone", Plast Reconstr. Surg., 108(5):1184-91 (Oct. 2001).

Defranzo, A.J., et al., "Vacuum-assisted closure for the treatment of degloving injuries", Plast Reconstr. Surg., 104 (7):2145-8 (Dec. 1999).

Gemeinhardt, K.D., et al., "Vacuum-assisted closure for management of a traumatic neck wound in a horse", Equine Veterinary Education, 17(1):27-33, (2005).

Genecov, D.G., et al., "A controlled subatmospheric pressure dressing increases the rate of skin graft donor site reepithelialization", Ann. Plast. Surg., 40(3):219-25 (Mar. 1998).

Laverty, D., et al., "Negative pressure wound therapy in the management of orthopedic wounds", Ostomy Wound Manage., 50(11A suppl):18S-9S (Nov. 2004).

Molnar, J.A., "Applications of negative pressure wound therapy to thermal injury", Ostomy Wound Manage., 50(4A suppl):17-9 (Apr. 2004).

Molnar, J.A., "The science behind negative pressure wound therapy", Ostomy Wound Manage., 50 (4A suppl):2-5 (Apr. 2004).

Molnar, J.A., et al., "Acceleration of integra incorporation in complex tissue defects with subatmospheric pressure", Plast Reconstr. Surg., 113(5):1339-1346 (Apr. 15, 2004).

Molnar, J.A., et al., "Management of an acute thermal injury with subatmospheric pressure", J. Burns Wounds, 4:83-92, 4:e5 (published online Mar. 24, 2005).

Molnar, J.A., et al., "Single-stage approach to skin grafting the exposed skull", Plast Reconstr. Surg., 105 (1):174-177 (Jan. 2000).

Mooney III, J.F., et al., "Treatment of soft tissue defects in pediatric patients using the V.A.C.™ system", Clin. Orthop. Relat. Res., No. 376, 26-31 (Jul. 2000).

Morykwas, M.J., et al., "Sub-atmospheric pressure wound treatment and cultured keratinocyte allografts", Cultured Human Keratinocytes and Tissue Engineered Skin Substitutes, R.E. Horch (ed., et al.), Georg Thieme Verlag, pp. 343-346 (2001).

Morykwas, M.J., et al., "Effects of varying levels of subatmospheric pressure on the rate of granulation tissue formation in experimental wounds in swine", Ann. Plast. Surg., 47(5):547-551 (Nov. 2001).

Morykwas, M.J., et al., "Nonsurgical modalities to enhance healing and care of soft tissue wounds", J. South. Orthop. Assoc., 6(4):279-288 (Winter 1997).

Morykwas, M.J., et al., "Techniques in Use of VAC.™ Treatment" (in English), Acta Chir. Austriaca Supplement 150: pp. 2-28, article on pp. p. 3-4 (1998).

Morykwas, M.J., et al., "The effect of externally applied subatmospheric pressure on serum myoglobin levels after a prolonged crushlischemia injury", J. Trauma, 53(3):537-540 (Sep. 2002).

Morykwas, M.J., et al., "Use of subatmospheric pressure to prevent doxorubicin extravasation ulcers in a swine model", J. Surg. Oncol., 72:14-7 (1999).

Morykwas, M.J., et al., "Use of subatmospheric pressure to prevent progression of partial-thickness burns in a swine model", J. Burn Care Rehabil., 20:15-21 (Jan./Feb., 1999).

Morykwas, M.J., et al., "Vacuum-assisted closure: a new method for wound control and treatment: animal studies and basic foundation", Ann. Plast Surg., 38(6):553-562 (Jun. 1997).

Plikaitis, C.M., et al., "Subatmospheric pressure wound therapy and the vacuum-assisted closure device: basic science and current clinical successes", Expert Rev. Med. Devices, 3(2):175-184, (Mar. 2006).

Rosser, C.J., et al., "A new technique to manage perineal wounds", Infections in Urology, 13(2):45-47 & 56 (Mar.-Apr. 2000).

Schlatterer, D., et al., "Orthopedic indications for negative pressure wound therapy", Ostomy Wound Manage., 51 (2A suppl):27S-8S (Feb. 2005).

Schneider, A.M., et al., "Re: use of specialized bone screws for intermaxillary fixation: reply", Ann. Plast. Surg., 47 (1): 93, (Jul. 2001).

Schneider, A.M., et al., "A new and reliable method of securing skin grafts to the difficult recipient bed", Plast. Reconstr. Surg., 102(4):1195-1198 (Sep. 1998).

Webb, L.X. "New techniques in wound management: vacuum-assisted wound closure", J. Am. Acad. Orthop. Surg., 10(5):303-311, (Sep.-Oct. 2002).

Webb, L.X., et al., "The contaminated high-energy open-fracture: a protocol to prevent and treat inflammatory mediator storm-induced soft-tissue compartment syndrome (IMSICS)", J. Am. Acad. Orthop. Surg., 14(10):SA82-S86 (Oct. 2006).

Webb, L.X., et al., "Wound management with vacuum therapy", Unfallchirurg, (English abstract on p. 919 and 2 pp. of Pubmed printout); 104(10):918-926 (Oct. 2001).

Yang, C.C., et al., "Vacuum-assisted closure for fasciotomy wounds following compartment syndrome of the leg", J. Surg. Orthop. Adv., 15(1):19-23 (Spring 2006).

Argenta, A., et al., "Deformation of superficial and deep abdominal tissues with application of a controlled vacuum", European Tissue Repair Society, Focus group meeting Topical Negative Pressure (TNP) Therapy, London UK (Dec. 4-6, 2003).

Argenta, L., et al., "Vacuum assisted closure (VAC therapy) for secondary closure of dehisced and infected wounds", Wound Repair and Regeneration, (Jul.-Sep., 1995), pp. 361; 5th Annual Meeting of the European Tissue Repair Society, Padova Italy, (1 page of abstract) (Aug. 30-Sep. 2, 1995).

Argenta, L.C., et al., "Use of V.A.C. for treatment of dehisced sternal incisions", Plastic Surgical Forum, vol. XXIII, 69th Annual Scientific Meeting of the American Society of Plastic Surgeons . . . , Los Angeles, CA, pp. 172-174. (2 sheets of abstract.) (Oct. 14-18, 2000).

Argenta, L.C., et al., "The VAC. as an adjunct for treatment for abdominal wounds", 66th Annual Meeting of the American Society of Plastic and Reconstructive Surgeons, San Francisco, CA, pp. 330-331; 1 sheet of abstract (Sep. 21-24, 1997).

Argenta, L.C., et al., "Vacuum assisted closure of chronic wounds", 65th Annual Scientific Meeting, American Society of Plastic and Reconstructive Surgeons, Dallas, TX, pp. 226-227; 1 sheet of abstract (Nov. 9-13, 1996).

Banwell, P., et al. eds., "Topical Negative Pressure TNP Focus Group Meeting", European Tissue Repair Society, Proceedings, London, UK 232 pp. (2003).

Banwell, P., et al., "Dermal perfusion in experimental partial thickness burns: the effect of topical subatmospheric pressure", Jan./Feb. 2000, Burn Care & Rehabil., part 2, 21(1):S161, Proceedings of the American Burn Association, 32nd Annual Meeting, Las Vegas, Nevada (Mar. 14-17, 2000).

Defranzo, A.J., et al., "109: Use of sub-atmospheric pressure for treatment of gunshot injuries", Plastic Surgical Forum, vol. XXIII, 69th Annual Scientific Meeting of the American Society of Plastic Surgeons . . . , Los Angeles, CA, pp. 180-181 (1 sheet of abstract) (Oct. 14-18, 2000).

Defranzo, A.J., et al., "The use of V.A.C. therapy for treatment of lower extremity wounds with exposed bone", 68th Annual Meeting of the American Society of Plastic and Reconstructive Surgeons, New Orleans, LA, pp. 37-38; 2 sheets of abstract (Oct. 24-27, 1999).

Kortesis, B., et al., "Vacuum-assisted closure for the treatment of open tibia fractures", 72nd Annual Meeting of the American Society of Plastic Surgeons, San Diego, CA, pp. 172-173; 1 sheet of abstract (Oct. 25-29, 2003).

Kremers, L., et al., "Effect of topical sub-atmospheric pressure treatment on angiotensin I and II levels post burn", 35th Annual Meeting, Abstract printed in J. Burn Care Rehabilitation, p. S44, Abstract No. 3 American Burn Association, Miami, Florida (Apr. 1-4, 2003).

Kremers, L., et al., "Serum interleukin levels post burn with and without application of sub-atmospheric pressure", 35th Annual Meeting, Abstract printed in Burn Care Rehabilitation, p. S43, Abstract No. 2, American Burn Association, Miami, Florida, (Apr. 1-4, 2003).

Marks, M.W., et al., "Management of complex soft tissue defects in pediatric patients using the V.A.C. wound closure", Plastic Surgical Forum, vol. XXI, 67th Annual Meeting of the American Society of Plastic and Reconstructive Surgeons . . . , Boston, MA, pp. 215-216 (Oct. 3-7, 1998).

Molnar, J.A., et al., "Improved skin graft adherence and vascularization of integra(R) using subatmospheric pressure—a laboratory study", Abstract printed in Burn Care & Rehabilitation, p. S111, Abstract No. 141; American Burn Meeting, 34th Annual Meeting, Chicago, IL, (Apr. 24-27, 2002).

Morykwas, M., et al., "Treatment of burned extremities using vacuum therapy (The V.A.C.)", Wound Repair and Regeneration, 3(3):367, (Jul.-Sep. 1995), 5th Annual Meeting of the European Tissue Society, Padova, Italy, (Aug. 30-Sep. 2, 1995).

Morykwas, M.J., "The use of the V.A.C. wound treatment system for acute and subacute wounds", Plaies & Cicatrices, Would Closure Healing, European Master Class in Wound Closure and Healing, Montpellier, France, (3pp.) (Apr. 21, 22 and 23, 1999).

Morykwas, M.J., et al., "Isolated muscle flap survival with complete venous occlusion: varying delay in external application of sub-atmospheric pressure", Plastic Surgical Forum, vol. XXI, 67th Annual Meeting of the American Society of Plastic and Reconstructive Surgeons . . . , Boston, MA, pp. 237 (Oct. 3-7, 1998).

Morykwas, M.J., et al., "Sub-atmospheric pressure for the treatment of lower extremity wounds", The Third Riva Congress, Current Perspectives in Fracture Management and Orthopaedic Reconstruction, Riva del Garda, Italy, pp. 135-136, (May 10-14, 2000).

Morykwas, M.J., et al., "Use of negative pressure to increase the rate of granulation tissue formation in chronic open wounds", FASEB J. part I, Abstracts 1-3006, (Extracellular Matrix and Healing, 799-800) (Feb. 19, 1993), Experimental Biology '93, abstract No. 800, New Orleans, Louisiana, (Mar. 28-Apr. 1, 1993).

Morykwas, M.J., et al., "Use of negative pressure to prevent progression of partial thickness burns", American Burn Association, vol. 26, 26th Annual Meeting, Orlando, Florida, pp. 157 (Apr. 20-23, 1994).

Morykwas, M.J., et al., "V.A.C. experience and difficult wounds," des Journees Regionales des Plaies et Cicatrisations, 2:76-90 (Sep. 22-23, 1997).

Morykwas, M.J., et al., "Negative pressure treatment of burned extremities", 65th Annual Scientific Meeting, American Society of Plastic and Reconstructive Surgeons, Dallas, TX, pp. 86-87; 1 sheet of abstract (Nov. 9-13, 1996).

Morykwas, M.J., et al., "The effect of V.A.C.(TM) therapy on the length of stay, total charges and average daily charge for patients assigned to DRG 263: analysis of 13 consecutive quarters", presented in part of the 28th Annual Conference of the Wound, Ostomy and Continence Nurses Society, Seattle, WA, (15 Sheets) (Jun. 15-19, 1996).

Park, C.A., et al., "Outpatient use of Integra® and subatmospheric pressure in the management of wound and burn reconstruction", J. Burn Care Rehabil., 26(2 suppl.):S113, Chicago, IL, (May 10-13, 2005).

Schneider, A.M., et al., "Muscle flap survival after complete venous occlusion by application of a negative pressure device", 66th Annual Meeting of the American Society of Plastic and Reconstructive Surgeons, San Francisco, CA pp. 300-302; 2 sheets of abstract (Sep. 21-24, 1997).

Schneider, A.M., et al., "Treatment of brown recluse spider bite wounds by external application of sub-atmospheric pressure", 68th Annual Meeting of the American Society of Plastic and Reconstructive Surgeons, New Orleans, LA, p. 35; 1 sheet of abstract (Oct. 24-27, 1999).

Webb, L.X., "Use of negative pressure devices in highly contaminated, high energy wounds", Extremity War Injuries: State of the Art and Future Directions, AAOS/OTA Extremity War Injures Symposium, Jan. 24-27, 2006, [Abstract].

Webb, L.X., et al., "Negative pressure wound therapy in the management of orthopedic wounds", Ostomy Wound Management, 50(4A Suppl.):26-27, Supplement—Proceedings from the 2003 National VAC.™ Education Conference (Apr. 2004).

Webb, L.X., et al., "The use of vacuum-assisted closure in composite wound management", The Third Riva Congress, Current Perspectives in Fracture Management and Orthopaedic Reconstruction, Riva del Garda, Italy, pp. 137 (May 10-14, 2000).

Morykwas, M.J., "Basic Research and Animal Studies," Presentation at the European Topical Negative Pressure Meeting in Salsbury, England, (Jun. 2005).

Defranzo, A.J., et al., "Vacuum assisted closure of the abdominal wall", 73rd Annual Meeting, American Association of Plastic Surgeons, Philadelphia, PA (2004), 1 sheet of abstract.

Fleischmann, W., et al., "Thoracic spinal, column, risks, and complications of therapy", OP-Journal, (7 sheets, 11 sheets of translation and 8 sheets of another Translation); 6(3): 31-35 (Dec. 1990).

Fleischmann, W., et al., "Vacuum sealing as treatment of soft tissue injury in open fractures", Unfallchirurg Springer-Verlag, (English abstract on first page, and 8 pages of English translation); 96:488-92, (1993).

Fleischmann, W., "Vacuum sealing for treatment of problematical wounds", Wund Forum Spezia—IHW, (4 sheets English translation); pp. 54-55 (1994).

Fleischmann, W., et al., "Vacuum assisted closure of wounds following dermatofasciotomy of the leg", Unfallchirurg., (English abstract on p. 284, and 1 sheet printout from PubMed); 99(4):283-7, (Apr. 1996).

Ford, C.N., et al., "Interim analysis of a prospective, randomized trial of vacuum-assisted closure versus the healthpoint system in the management of pressure ulcers", Ann. Piast. Surg., (11 sheets); 49(1):55-61 (Jul. 2002).

Fox, R., "A rapid screen for drug abuse", Pharmaceutical J., p. 789, (Jun. 18, 1988).

Gouttefangeas, C., et al., "Functional T lymphocytes infiltrate implanted polyvinyl alcohol foams during surgical wound closure therapy," Clin. Exp. Immunol., 124(3):398-405 (Jun. 2001).

Grabowski, S., "Treatment of the wounds in hypotension", Pol. Tyg. Lek., (English abstract on p. 21 and 1 sheet printout from PubMed); 19:19-21, (Jan. 1, 1964).

Greer, S.E., et al., "Subatmospheric pressure dressing for saphenous vein donor-site complications," Ann. Thorac. Surg., (6 sheets); 71(3):1038-40 (Mar. 2001).

Excerpts "Dead Space", "Wound Closure", "Drainage", "Dressing" and "Epilogue" in "Fundamentals of Wound Management," T.K. Hunt and J.E. Dunphy, eds., Appleton-Century Crofts NY pp. 416-447, (1979).

Hawkins-Bradley, B., et al., "Treatment of a nonhealing wound with hypergranulation tissue and rolled edges", J. Wound Ostomy Continence Nurs., 29(6):320-324 (Nov. 2002).

Harlan, J.W., "Treatment of open sternal wounds with the vacuum-assisted closure system: a safe, reliable method", Plast. Reconstruct. Surg., 109(2):710-12 (Feb. 2002).

Harris, A., et al., "Hypergranulation tissue: a nontraumatic method of management", Ostomy Wound Manage., 40 (5):20-22, 24, 26-30 (Jun. 1994).

Hartnett, S., "Heparin-induced thrombocytopenia as the cause of gluteus muscle necrosis: a case study describing the benefits of multidisiplinary physical and psychosocial interventions", Ostomy Wound Manage., 47(5):18-26 (May 2001).

Hartz, R.R., et al., "Healing of the perineal wound", Arch. Surg., 115:471-474, (Exhibit D-395) (Apr. 1980).

Hersh, R.E., et al., "A technique for the treatment of sternal infections using the vacuum assisted closure™ device", Heart Surg. Forum, 4(3):211-15 (2001).

Bier, A., "Hyperemia by Suction Apparatus" Chapter VIII, pp. 74-85 in "Hyperemia as a therapeutic agent", Chicago, III.: Roberts Publishing, (1905).

Iankov, N.I., "Stimulation of consolidation of mandibular fractures by means of vacuum therapy", Stomatologiia (Mosk.), (1 sheet Russian with English abstract, 1 sheet English translation and 1 sheet printout from PubMed); 50 (5):86 (Sep.-Oct. 1971).

Ingber, D.E., "Mechanical signaling and the cellular response to extracellular matrix in angiogenesis and cardiovascular physiology", Circ. Res., 91:877-887 (Nov. 15, 2002).

Inoiatov, I.M., et al., "Vacuum aspiration in the treatment of the perineal wound following extirpation of the rectum", Khirurgiia (Mosk.), (English abstract on last page, 7 sheets of English translation, 1 sheet prinout from PubMed); 47 (1):74-8 (Jan. 1971).

Kalailieff, D., "Vacuum-assisted closure: wound care technology for the new millennium", Perspectives, 22(3):28-9 (Fall 1998).

Kercher, K.W., et al., "Successful salvage of infected PTFE mesh alter ventral hernia repair", Ostomy Wound Manage., 48(10):40-5 (Oct. 2002).

Kiernan, M., "The process of granulation and its role in wound healing", Community Nurse, 5(5):47-48 (Jun. 1999).

Kloth, L.C., "5 questions—and answers—about negative pressure wound therapy", Adv. Skin Wound Care, 15(5):226, 228-9 (Sep.-Oct. 2002).

Kochnev, VA, "The use of a vacuum drainage system in the prevention of postoperative wound complications in tumor patients", Vopr. Onkol., (English abstract on last page, 4 sheets of English translation, and 1 sheet printout from PubMed); 13(5)102-5 (1967).

Kostiuchenok, B.M., et al., "Vacuum treatment in the surgical management of suppurative wounds", Vestn. Khir. Im. 1.1. Grek., (English abstract on p. 21, 4 sheets English translation, and 1 sheet printout from PubMed); 137(9): 18-21 (Sep. 1986).

The Kremlin Papers: perspectives in wound care, "A collection of published studies complementing the research and innovation of wound care", 5 articles from the Russian Medical Journal "Vestnik Khirurgii", as translated by BlueSky Publishing, a division of the BlueSky Medical Group Inc. (16 sheets) (2004) (translations of Russian articles dated 1986-1991).

Kusel, C., "Use of V.A.C. (vacuum-assisted closure) therapy in general surgery: problem wounds deprived of air", Pftege Z., (and 1 sheet printout from PubMed); 55(6):408-412 (Jun. 2002).

Labler, L., et al., "Vacuum sealing of problem wounds", Swiss Surg., (English abstract on first page, 1 sheet printout from PubMed); 8(6):266-7 (2002).

Leaper, D.J., "The wound healing process", Advances in Wound Management, T.D. Turner, et al., eds., pp. 7-16, New York: John Wiley and Sons, (1986).

Letsou, G.V., et al. "Stimulation of adenylate cyclase activity in cultured endothelial cells subjected to cyclic stretch", J. Cardiovasc. Surg., (Sep.-Oct. 1990) 31(5):634-639; presented at XIX World Congress of International Society for Cardiovascular Surgery (Toronto, Canada, Sep. 5-9, 1989).

Marston, W.A., et al., "The efficacy and safety of Dermagraft in improving the healing of chronic diabetic foot ulcers: results of a prospective randomized trial", Diabetes Care, 26(6) 10 pp., (Exhibit 271) (Jun. 1, 2003).

Medela Dominant promotional literature (2 pp.) (labeled circa 1984-1985).

Medical Technology & Innovation, "Medical technology is extending life, reducing costs", 1(46), (4 sheets) (Dec. 4, 2000).

Meehan, P.A., "Open abdominal wounds: a creative approach to a challenging problem", Progressions, 4(2):3-8, 11 (1992).

Mendez-Eastman, S., "Negative pressure wound therapy", Plast. Surg. Nurs., 18(1):27-29, 33-37 (Spring 1998).

Mendez-Eastman, S., "Guidelines for using negative pressure wound therapy", Adv. Skin Wound Care, 14 (6):314-323 and 324-325. (16 pp.) (Nov.-Dec. 2001).

Mendez-Eastman, S., "New treatment for an old problem: negative-pressure wound therapy", Nurs., 32(5):58-64. (12 sheets) (May 2002).

Mirazimov, B.M., et al., "Microftora of prolonged non-healing wounds and the effectiveness of the vacuum evaporative method", Khirurgiia (Mosk.), (English abstract on pp. 42-43, 6 sheets English translation, and 1 sheet printout from PubMed); 43(4):40-3 (Apr. 1967).

Mirazimov, B.M., "Free skin graft of the foot with vacuum preparation of the wound surface", Orthop. Travmatol. Protez., (5 sheets English translation and 1 sheet printout from PubMed); 27(10):19-22 (Oct. 1966).

Mirazimov, B.M., "Preparation of wounds and ulcers for skin grafting by vacuum treatment", Beitr. Orthop., (and 9 sheets English translation); 14(4):224-30 (1967).

Mirazimov, B.M., "Free skin grafting of wounds and ulcers using the 'vacuum treatment' method", Orthop. Travmatol. Protez., (7 sheets English translation, and 1 sheet printout from PubMed); 28(1):54-58, (Jan. 1967).

Mizuno, K., "Suctioning sponge", Arch. Opthalmol., 101(2):294 (Feb. 1983).

Mulder, G. D. et al. (eds.), Clinicians' Pocket Guide to Chronic Wound Repair, 106 pp., second edition (1992).

Muller, G., "Vacuum dressing in septic wound treatment", Langenbecks Arch. Chir. Suppl. Kongressbd., (English abstract on p. 537, and 1 sheet printout from PubMed); 114:537-41 (1997).

Murray, J., et al., "On the local and general influence on the body of increased and diminished atmospheric pressure", Lancet, 1:909-917 (1834-1835).

Murray, Y., "Tradition rather than cure?", Wound Care, Nurs. Times, 84(38):75, 79 and 80 (Sep. 21-27, 1988).

Mutschler, W. et al., "Temporary skin replacement. An important component in the treatment of skin defects of various etiologies", ZFA, (and 12 sheets of English translation); S. 714-720, pp. 3-15, (1989).

Netudykhatka, O.I., "Effect of low vacuum on the course of the reparative process in bone tissue", Vopr. Kurortol. Fizioter. Lech. Fiz. Kult., (5 sheets English translation, and 1 sheet printout from PubMed); 37(5):411-5 (Sep.-Oct. 1972).

Nikolov, A., "Vacuum treatment method in postphlebitic and varicose trophic ulcers of the lower extremities", Khirurgiia (Saiia), (English abstract on p. 371 and 1 sheet printout from PubMed); 34(4):368-371 (1981).

3M Ioban 2, Breathability, Conformability and Strength, Breathability—Moisture Vapor Transmission Rate and Conformability and Strength—Tensile Strength, Elongation and Fn Modulus Test (1 sheet).

ACU-derm® Transparent Moisture Vapor Permeable Polyurethane Dressing, (14 sheets).

Aeros, "Moblvac II", (1 sheet).

Banwell, P.E., et al., "Topical negative pressure (TNP): the evolution of a novel wound therapy," J. Wound Care, 12 (1):22-8 (Jan. 2003).

Barillo, D., et al., "Management of burns to the hand", Wounds 2003, 15(1):4-9, Health Management Publications, Inc., (11 sheets) (Posted Feb. 12, 2003).

Cardozo, M., "A case study of holistic wound management in intensive care", Br. J. Nurs., 12(11 Suppl):S35-37, S40-42 (Jun. 2003).

Chariker-Jeter® Wound Drainage Kit Instructions, Item #500.7777, BlueSky Medical, 2 pp.

Chariker-Jeter® Wound Drainage Kit, BlueSky Medical, and Wooding-Scott® Drainage/Irrigation Kit, 2 page advertisement with business card from Quality Medical Supply.

Chariker-Jeter® Wound Sealing Kit, Wound Application Instructions, 1 page advertisement.

Collier, M., "Topical negative pressure therapy", Nurs. Times, 99(5):54-5 (Feb. 4-10, 2003).

Cook Pneumothorax Catheter Set, Wayne Pneumothorax Catheter Set, Emergency Medicine, Videotape advertisement. (3 pp.).

Cooper, D., "Wound Healing", Nurs. Clin. N. Am., 25(1):163-164 (Mar. 1990).

Coyle, M.B., et al., "A case study: positive outcomes to negative pressure wound therapy—a collaborative assessment", Hospital of Saint Raphael, 1 page chart.

Deknatel, Div. of Howmedica, Inc. Queens Village, NY 11429. "Pleur-evac."

Domkowski, P.W., et al., "Evaluation of vacuum-assisted closure in the treatment of poststerotomy mediastinitis," J. Thorac. Cardiovasc. Surg., 126(2):386-90 (Aug. 2003).

Dow Corning Silastic® Foam Dressing: A New Concept in the Management of Open Granulating Wounds, 2 pp. of advertisements.

DuoDERM™ Hydroactive™ Dressing, "In wound management—Now, a proven environment for fast healing", 1 page advertisement.

Edlich, R.F., et al., "Surgical devices in wound healing management", Wound Healing: Biochemical and Clinical Aspects, pp. 581-599 (1992).

Eginton, M.T., et al., "A prospective randomized evaluation of negative-pressure wound dressings for diabetic foot wounds", Ann. Vasc. Surg., 17(6):645-9 (2003).

Eisenbud, D.E., "Dressings" in Modern wound management, Anadem Publishing, pp. 109-116 (Jan. 1999).

Emerson, J. H. Emerson Co., "Emerson Transport Suction Unit", 1 sheet of advertisement.

Emerson, Series 55, "Emerson post-operative suction pumps", 1 sheet of advertisement.

Erdmann, D., et al., "Abdominal wall defect and enterocutaneous fistula treatment with the vacuum-assisted closure (VAC) system", Plast. Reconstruct. Surg., 108(7):2066-8 (Dec. 2001).

Ferreira, M.C., et al., "The vacuum assisted closure of complex wounds: report of three cases", Rev. Hosp. Clin. Fac. Med. S. Paulo, 58(4):227-30 (2003).

Fisher, A., et al., "Vacuum assisted wound closure therapy", Issues Emerg. Health Technol., Issue 44,6 pp. (Mar. 2003).

Grams Aspirator, et al., Grams Medical, catalog pp. (3 pp.) (prices as of Aug. 1991 and Sep. 1992).

Greer, S.E., "Whither subatmospheric pressure dressing?" Ann. Plast. Surg., 45(3):332-336 (Apr. 2000).

Hallberg, H., et al., "Vaginal construction with skin gralts and vacuum-assisted closure", Scand. J. Plast. Reconstr. Surg. Hand Surg., 37(2):97-101 (2003).

Hargens, A.R., et al., "Control of circulatory function in altered gravitational fields", Physiologist, 35(1 Suppl.):S80-3 (4 sheets) (Feb. 1992).

Herrmann, L.G., et al., "The conservative treatment of arteriosclerotic peripheral vascular diseases: passive vascular exercises (pavaex therapy)", Ann. Surg., 100(4): 750-760 (Oct. 1934).

Hess, C.L., et al., "A review of mechanical adjuncts in wound healing: hydrotherapy, ultrasound, negative pressure therapy, hyperbaric oxygen, and electrostimulation", Ann. Plast. Surg., 51(2):210-8 (Aug. 2003).

Hilsabeck, Jr., "The presacral space as a collector of fluid accumulations following rectal anastomosis: tolerance of rectal anastomosis to closed suction pelvic drainage", Dis. Colon Rectum, 25(7):680-684 (Oct. 1982).

Hodzic, J., et al., "Vacuum sealing of extensive wound healing disorders alter kidney transplantation," Urologe A., (6 sheets in German, English abstract on p. 2 and 1 sheet printout from PubMed); 42(8):1097-100 (Aug. 2003) (Epub Apr. 3, 2003).

Howmedica porto-vac®, "Gentle, Steady Wound Drainage", 1 page advertisement.

Industrial Equipment News, P.O. Box 1158, Skokie, IL 60076-9786, (1 sheet).

Instruction Manual, Creative Medical Laboratories, Inc. P.O. Box 6347, Rochester, Minn. 55903. "TUGS" (Transportable Universal Gradient Suction) (7 sheets).

Kaufman, M.W., et al., "Vacuum-assisted closure therapy: wound care and nursing implications", Dermatol. Nurs.,15 (4): 317-20, 323-236 (Aug. 2003).

Krasner, D.L., "Managing wound pain in patients with vacuum-assisted closure devices", Ostomy Wound Manage., 48(5):38-43 (May 2002).

Lamke, L.O., et al., "The evaporative water loss from burns and the water-vapour permeability of grafts and artificial membranes used in the treatment of burns", Burns, 3(3):159-165 (Mar. 1977).

Landis, E.M., et al., "The effects of alternate suction and pressure on blood flow to the lower extremities", J. Clin. Invest., 12(5):925-561 (Sep. 1933).

Langworthy, M., et al., "Treatment of the mangled lower extremity alter a terrorist blast injury", Clin. Orthop. Relat. Res., (422):88-96 (May 2004).

Luckraz, H., et al., "Vacuum-assisted closure as a treatment modality for infections alter cardiac surgery", J. Thorac. Cardiovasc. Surg., 125(2):301-5 (Feb. 2003).

Maddin, W.S., et al., "The biological eflects of a pulsed electrostatic field with specifie reference to hair: electrotrichogenesis", Int. J. Dermatol., 29(6):446-450 (Jul.-Aug. 1990).

Manualectric Breastpump, Catalog pp. (4 pp.).

McCulloch, J.M., et al., "Vacuum-compression therapy for the treatment of an ischemic ulcer", Phys. Ther., 73 (3):165-9 (Mar. 1993).

Morykwas, M.J., "Use of sub-atmospheric pressure to prevent adriamycin extravasation ulcers in a pig model", first presented at The 44th Annual Meeting of Plastic Surgery Research Council, Pittsburg, PA, (May 22-26, 1999).

Molnar, J.A., "V.A.C. and burn care", presentation slides.

Slides regarding use of V.A.C.

"The Remington Post: Business and clinical strategies for home care executives", containing articles by J.A. Molnar, D.G. Armstrong, et al., and S. Mendez-Eastman; (Nov./Dec. 2004).

Polly Jr., D.W., et al., "Advanced medical care for soldiers injured in Iraq and Afghanistan", Minn. Med., 87(11):42-4 (Nov. 2004).

Stone, P.A., et al., "Vacuum-assisted fascial closure for patients with abdominal trauma", J. Trauma, 57:1082-6 (Nov. 2004).

Connolly, T.P., "Necrotizing surgical site infection after tension-free vaginal tape", Obstet. Gynecol., 104(6):1275-6 (4 pages) (Dec. 2004).

Wackenfors, A., et al., "Effects of vacuum-assisted closure therapy on inguinal wound edge microvascular blood flow", Wound Rep. Regen., 12(6):600-6 (Nov.-Dec. 2004).

Schaffzin, D.M., et al., "Vacuum-assisted closure of complex perineal wounds", Dis. Colon Rectum, 47:1745-8 (Oct. 2004) (Published online Aug. 24, 2004).

Yousaf, M., et al., "Use of vacuum-assisted closure for healing of a persistent perineal sinus following panproctocolectomy: report of a case", Dis. Colon Rectum, 47(8):1403-8 (Aug. 2004) (Published online Aug. 12, 2004).

Fox, A., et al., "An unusual complication of vacuum assisted closure in the treatment of a pressure ulcer", J. Wound Care, 13(8):344-5 (Sep. 2004).

Saxena, V., et al., "Vacuum-assisted closure: microdeformations of wounds and cell proliferation", Plast. Reconstruct. Surg., 114(5):1086-96 (Oct. 2004).

Scholl, L., et al., "Sternal osteomyelitis: use of vacuum-assisted closure device as an adjunct to definitive closure with sternectomy and muscle flap reconstruction", J. Card. Surg., 19(5):453-61 (Sep.-Oct. 2004).

Ohye, R.G., et al. "Primary closure for postoperative mediastinitis in children", J. Thorac. Cardiovasc. Surg., 128 (3):480-6 (Sep. 2004).

Tang, S.Y., et al., "Influence of vacuum-assisted closure technique on expression of Bcl-2 and NGF/NGFmRNA during wound healing", Zhonghua Zheng Xing Wai Ke Za Zhi, (English abstract on first page 1 sheet printout from PubMed); 20(2):139-42 (Mar. 2004).

Armstrong, D.G., et al., "Guidelines regarding negative wound therapy (NPWT) in the diabetic foot", Ostomy Wound Manage., 50(4B Suppl.):3S-27S (Apr. 2004).

Shilt, J.S., et al., "Role of vacuum-assisted closure in the treatment of pediatric lawnmower injuries", J. Pediatr. Orthop., 24(5):482-7 (Sep.-Oct. 2004).

Antony, S., et al., "A retrospective study: clinical experience using vacuum-assisted closure in the treatment of wounds", J. Natl. Med. Assoc., 96(8):1073-7 (Aug. 2004).

Steenvoorde, P., et al., "Vacuum-assisted closure therapy and oral anticoagulation therapy", Plast. Reconstruct. Surg., 113(7):2220-1 (Jun. 2004).

Oczenski, W., et al., "Vacuum-assisted closure for the treatment of cervical and mediastinal necrotizing fasciitis", J. Cardiothorac. Vasc. Anesth., 18(3):336-8 (Jun. 2004).

Carson, S.N., et al., "Vacuum-assisted closure used for healing chronic wounds and skin grafts in the lower extremities", Ostomy Wound Manage., 50(3):52-8 (9 sheets) (Mar. 2004).

Marathe, U.S., et al., "Use of the vacuum-assisted closure device in enhancing closure of a massive skull defect", Laryngoscope, 114(6):961-4 (8 sheets) (Jun. 2004).

Schintler, M.V., et al., "The impact of the VAC-treatment for locally advanced malignancy of the scalp", Zentralbl. Chir., (English abstract on first page, 1 sheet printout from PubMed); 129 Suppl: 1:S141-S146 (May 2004).

Querings, K., et al., "Revitalization of a gluteal abscesses with V.A.C. therapy (vacuum assisted closure)", Zentralbl. Chir, (English abstract on first page, 1 sheet printout from PubMed); 129 Suppl 1:S138-S140 (May 2004).

Kall, S., et al., "Influence of foam—and tubing material of the vacuum assisted closure device (V.A.C.) on the concentration of transforming growth factor beta 1 in wound fluid", Zentralbl. Chir., (English abstract on first page, 2 sheets printout from PubMed); 129 Suppl 1: S113-S115 (May 2004).

Mang, R., et al., "Vacuum therapy in a pre- and postsurgical ulcera crurum", Zentralbl. Chir., (English abstract on first page, 1 sheet printout from PubMed); 129 Suppl 1:S101-S103 (May 2004).

Steiert, A.E., et al., "The V.A.C. system (vacuum assisted closure) as bridging between primary osteosynthesis in conjunction with functional reconstructed of soft tissue—open fractures type 2 and type 3", Zentralbl. Chir., (English abstract on first page, 2 sheets printout from PubMed); 129 Suppl 1:S98-100 (May 2004).

Karl, T., et al., "Indications and results of V.A.C. therapy treatments in vascular surgery—state of the art in the treatment of chronic wounds", Zentralbl. Chir., (English abstract on first page, 1 sheet printout from PubMed); 129 Suppl 1:S74-S79 (May 2004).

Ferbert, T., et al., "Treatment of soft tissue defects on hand and forearm with vacuum assisted closure", Zentralbl. Chir., (English abstract on first page, 1 sheet printout from PubMed); 129 Suppl 1:S57-S58 (May 2004).

Halama, D., et al., "Intraoral application of vacuum-assisted closure in the treatment of an extended mandibular keratocyst", Zentralbl. Chir., (English abstract on first page, 1 sheet printout from PubMed); 129 Suppl 1:S53-S56 (May 2004).

Fleck, T., et al., "Early treatment of sternal wound infections with vacuum assisted closure therapy reduces involvement of the mediastinum and further diminishes the need of plastic reconstructive surgery", Zentralbl. Chir., (1 sheet printout from PubMed); 129 Suppl 1:S35-S37 (May 2004).

Kutschka, I., et al., "Vacuum assisted closure therapy improves early postoperative lung function in patients with large sternal wounds", Zentralbl. Chir., (English abstract on first page, 1 sheet printout from PubMed); 129 Suppl 1:S33-S34 (May 2004).

Labler, L., et al., "New application of V.A.C. (vacuum assisted closure) in the abdominal cavity in case of open abdomen therapy", Zentralbl. Chir., (English abstract on first page, 2 sheets printout from PubMed); 129 Suppl 1:S14-S19 (May 2004).

Wild, T., et al., "Consensus of the German and Austrian Societies for Wound Healing and Wound Management on vacuum closure and the V.A.C. treatment unit", Zentralbl. Chir., (English abstract on first page, 2 sheet printout from PubMed and 1 sheet of erratum); 129 Suppl 1:S7-S11 (May 2004).

Weed, T., et al., "Quantifying bacterial bioburden during negative pressure wound therapy. Does the wound VAC enhance bacterial clearance?"Ann. Plast. Surg., 52(3):276-80 (Mar. 2004).

Mustoe, T., "Understanding chronic wounds: a unifying hypothesis on their pathogenesis and implications for therapy", Am. J. Surg., 187(5A):65S-70S (May 2004).

Tzeng, Y.J., et al., "Using vacuum-assisted closure (VAC) in wound management", Hu Li Za Zhi, (English abstract on last page, 1 sheet printout from PubMed); 51(2):79-83 (April 2004).

Quah, H.M., et al., "Vacuum-assisted closure in the management of the open abdomen: a report of a case and initial experiences", J. Tissue Viability, 14(2):59-62 (Apr. 2004).

Emohare, O., et al., "Vacuum-assisted closure use in calciphylaxis", J. Burn Care Rehabil., 25(2):161-4 (Mar.-Apr. 2004).

Wackenfors, A., et al., "The effect of vacuum-assisted closure therapy on the pig femoral artery vasomotor responses", Wound Repair Regen., 12(2):244-51 (Mar.-Apr. 2004).

Sjogren, J., et al., "Vacuum-assisted closure therapy in mediastinitis after heart transplantation", J. Heart Lung Transplant., 23(4):506-7 (Apr. 2004).

Miller, Q., et al., "Effect of subatmospheric pressure on the acute healing wound", Curr. Surg., 61(2):205-8 (Mar.-Apr. 2004).

Penn, E., et al., "Management of a dehisced abdominal wound with VAC therapy", Br. J. Nurs., 13(4):194, 196, 198-201 (Feb. 26-Mar. 10, 2004).

Moues, C.M., et al., "Bacterial load in relation to vacuum-assisted closure wound therapy: a prospective randomized trial", Wound Repair Regen., 12(1):11-7 (Jan.-Feb. 2004).

Schimp, V.L., et al., "Vacuum-assisted closure in the treatment of gynecologic oncology wound failures", Gynecol. Oncol., 92(2):586-91 (Feb. 2004).

Aru, G.M., et al., "Limitations on the role of vacuum-assisted closure in cardiac surgery", J. Thorac. Cardiovasc. Surg., 127(2):604-5 (Feb. 2004).

Bihariesingh, V.J., et al., "Plastic solutions for orthopaedic problems", Arch. Orthop. Trauma. Surg., 124(2):73-6 (Mar. 2004) (Epub Jan. 17, 2004).

Kaplan, M., "Managing the open abdomen", Ostomy Wound Manage., 50(1A suppl):C2, 1-8, and 1 sheet of quiz (Jan. 2004).

Colwell, A.S., et al., "Management of early groin vascular bypass graft infections with sartorius and rectus femoris flaps", Ann. Plast. Surg., 52(1):49-53 (Jan. 2004).

Evidence Report/Technology Assessment, No. 111, "Wound healing technologies: low-level laser and vacuum-assisted closure", prepared for Agency for Healthcare Research and Quality by the Blue Cross and Blue Shield Association Technology Evaluation Center Evidence-based Practice Center, under Contract No. 290-02-0026, AHRQ Publications Clearinghouse, Available Dec. 2004.

Wolvos, T., "Wound instillation—the next step in negative pressure wound therapy. Lessons learned from initial experiences", Ostomy Wound Manage., 50(11):56-58, 60-66 (Nov. 2004).

Bluman, E.M., et al., "Subatmospheric pressure-induced compartment syndrome of the entire upper extremity. A case report", J. Bone Joint Surg. (Am.), 86-A(9):2041-4 (Sep. 2004).

Kamolz, L.P., et al., "Use of subatmospheric pressure therapy to prevent burn wound progression in human: first experiences", Burns, 30(3):253-8 (May 2004) (Available online Mar. 16, 2004).

Jones, S.M., et al., "Advances in wound healing: topical negative pressure therapy", Postgrad. Med. J., 81 (956):353-7 (Jun. 2005).

M. Gosta Arturson, The Pathophysiology of Severe Thermal Injury, *JBCR*, 6(2):129-146 (Mar.-Apr.) 1985.

R. A.F. Clark et al., The Molecular and Cellular Biology of Wound Repair, Chapter 1 (1988).

Jeter, K.F. et al. (eds.), "Managing Draining Wounds and Fistulae: New and Established Methods," Chronic Wound Care: Health Management Publications, 1990, pp. 240-246.

Aeros, Aeros Instruments, Inc. 1111 Lakeside Drive, Gurnee, IL 60031. Aug. 1993. "Care-E-Vac."

Aeros, Aeros Instruments, Inc. 3411 Commercial Ave., Northbrook, IL 60062. Oct. 1988. Part No. 1504-02 7M. "Instavac Aspirator."

Fleischmann, W. *Acta Orthopaedica Belgica*. vol. 58, Suppl. I-1992 "Treatment of Bone and Soft Tissue Defects in Infected Nonunion."

Valenta, A.L. *American Journal of Nursing*. Apr. 1994. "Using the Vacuum Dressing Alternative for Difficult Wounds." 94:44-5.

Saunders, J.W., The Lancet, pp. 1286-1287, Jun. 28, 1952, "Negative-Pressure Device for Controlled Hypotension during Surgical Operations".

Wolthuis et al, Physiological Reviews, 54: 566-595, Jul. 1974, "Physiological Effects of Locally Applied Reduced Pressure in Man".

Viljanto et al., Br. J. Surg., 63: 427-430, 1976, "Local Hyperalimentation of Open Wounds".

Dillon, R. Angiology—The Journal of Vascular Diseases, pp. 47-56, Jan. 1986, "Treatment of Resistant Venous Stasis Ulcers and Dermatitis with the End-Diastolic Pneumatic Compression Boot".

Lundvall et al., Acta Physiol Scand, 136: 403-409, accepted Jan. 28, 1989, "Transmission of externally applied negative pressure to the underlying tissue. A study on the upper arm of man".

Klemp et al., The Journal of Investigative Dermatology, pp. 725-726 (1989), "Subcutaneous Blood Flow in Early Male Pattern Baldness".

A. Harle, Z. Orthop., 127: 513-517 (1989), "Schwachstellen herkommlicher Drainagen" with English Translation.

Dunlop et al., Br. J. Surg., 77: 562-563 (1990), "Vacuum drainage of groin wounds after vascular surgery: a controlled trail".

Nakayama et al., Ann. Plast. Surg., 26:499-502 (1991), "A New Dressing Method for Free Skin Grafting in Hands".

Hargens et al., Aviation, Space and Environmental Medicine, pp. 934-937, Oct. 1991, "Lower Body Negative Pressure to Provide Load Bearing in Space".

Bucalo et al. "Inhibition of Cell Proliferation by Chronic wound Fluid." Wound Repair and Regeneration. 181-186 Jul. 1993.

Falanga, Vincent. "Growth Factors and Chronic Wounds: The need to Understand the Microenvironment." Journal of Dermatology, Bol. 19: 667-672. 1992.

Urschel et al. "The Effect of Mechanical Stress on Soft and Hard Tissue Repair; a Review." British Journal of Plastic Surgery. 41, 182-186. 1988.

Gogia, Prem P. "The Biology of Wound Healing." Ostomy/Wound Management. Nov.-Dec. 1992. pp. 12, 14-16, 18-20, 22.

Wysocki et al. "Wound Fluid from Chronic Leg Ulcers Contains Elevated Levels of Metalloproteinases MMP-2 and MMP-9." The Society for Investigative Dermatology, Inc. Jul. 1993. 64-68.

Rastgeldi, S.: I. Pressure Treatment of Peripheral Vascular Diseases. II. Intermittent Pressure Treatment of Peripheral Vascular Diseases. Opuscula Medica, Suppl. XXVII, 1972.

W. Fleischmann, U. Becker, M. Bischoff, H. Hoekstra, "Vacuum sealing: indication, technique, and results", Eur. J. Orthop & Traumato (1995) 5:37-40.

Teder H, Sanden G, Svedman P. Continuous Wound Irrigation in the Pig. J Invest Surg 1990;3:399-407.

Nakayama Y, Tomotari I, Soeda S. A New Method for the Dressing of Free Skin Grafts. Plast Reconstr Surg 1990;86:1216-1219.

Brock WB, Barker DE, Burns RP. Temporary Closure of open abdominal wounds: the vacuum pack. Amer Surg 1995;61:30-5.

Shein M, Saadia R, Jameson JR, Decker GAG. The "sandwich technique" in the Management of the Open Abdomen. Br J Surg 1986;73:369-70.

Broome A. Hansson L, Lundgren F, Smedberg S. Open Treatment of Abdominal Septic Catastrophies. World J. Surg 1983;7:792-6.

Vatanasapt V, Areemit S, Jeeravipoolvarn P, et al. Red rubber bulb, cheap and effective vacuum drainage. Journal of the Medical Association of Thailand 1989;72:193-7.

Brummelkamp WH, Taat CW, Slors JF. High-vacuum drainage and primary perineal wound closure in abdominoperineal excision of the rectum. Netherlands Journal of Surgery 1991;43:236-9.

Sames CP. Sealing of wounds with vacuum drainage [letter] Br Med J 1977;2:1123.

Greer SE, Longaker MT, Margiotta M. Preliminary Results from a Multicenter, Randomized, Controlled, Study of the Use of Subatmospheric Pressure Dressing for Pressure Ulcer Healing. Wound Repair and Regeneration 1999;7:255.

Greer SE, Longaker MT, Margiotta M, Matthews AJ, Kasabian A. The Use of Subatmospheric Pressure Dressing for the Coverage of Radial Forearm Free Flap Donor-Site Exposed Tendon Complications. Ann Plast Surg 1999;43:551-554.

Greer SE, Duthie E, Cartolano B, Koehler KM, Maydick-Youngberg D, Longaker MT. Techniques for Applying Subatmospheric Pressure Dressing to Wounds in Difficult Regions of Anatomy. JWOCN 1999;26:250-3.

Greer SE, Kasabian A, Thorne C, Borud L, Sims CD, Hsu M. The Use of Subatmospheric Pressure Dressing to Salvage a Gustilo Grade IIIB Open Tibia Fracture with Concomitant Osteomyelitis and Avert a Free Flap. Ann Plast Surg 1998;41:687.

Banwell P. Withey S, Holten I. The use of negative pressure to promote healing [letter; comment]. Brit J Plast Surg 1998;51:79.

Blackburn J H Boemi L, Hall WW. et al. Negative-pressure dressings as a bolster for skin grafts. Ann Plast Surg 1998;40:453-7.

Smith LA, Barker DE, Chase CW, et al. Vacuum Pack Technique of Temporary Abdominal Closure: A Four-Year Experience. Amer Surg 1997;63:1102-8.

Mullner T, Mrkonjic L, Kwasny O, Vecsei V. The use of negative pressure to promote the healing of tissue defects: a clinical trial using the vacuum sealing technique [see comments]. Brit J Plast Surg 1997;50:194-9.

Registration No. 1982349. Owner, KCI Inc., 3440 E. Houston Street San Antonio Texas 78219. Source: United States Patent and Trademark Office official website. Filing date May 1, 1995 Registration Date Jun. 25, 1996.

Hidden Interest—A Special Report.; When Physicians Double as Entrepreneurs. The New York Times. 11pp. Nov. 30, 1999.

Philbeck, Thomas E., et al., "The Clinical and Cost Effectiveness of Externally Applied Negative Pressure Wound Therapy in the Treatment of Wounds in Home Healthcare Medicare Patients". Ostomy/Wound Management 45(11) 41-44, 46-50 (1999).

Meara, John G., et al., "Vacuum-Assisted Closure in the Treatment of Degloving Injuries". Annals of Plastic Surgery 42(6) 589-594 (1999).

Obdeijn, Miryam C., et al., "Vacuum-Assisted Closure in the Treatment of Poststernotomy Mediastinitis". Ann Thorac Surgery 68 2358-60 (1999).

Mendez-Eastman, Susan., "When wounds won't heal". RN 20-24 (1998).

Hartnett, Jacqueline M., "Use of Vacuum-Assisted Wound Closure in Three Chronic Wounds". JWOCN 25 (6) 281-290 (1998).

Mendez-Eastman, Susan., "Use of Hyperbaric Oxygen and Negative Pressure Therapy in the Multidisciplinary Care of a Patient with Nonhealing Wounds". JWOCN 26(2) 67-76 (1999).

Garcia-Rinaldi, et al., "Improving the Efficiency of Wound Drainage Catheters", J. Surg., 1975, pp. 372-373.

Raffl, et al. "The Five Year Survival Rate for Gastric Cancer: Statistical Study from Syracuse Medical Center", Cancer, 6:756-759, Jul. 1953.

Raffl, et al., The Use of Negative Pressure Under Skin Flaps After Radical Mastectomy, Ann. Surg. 136: 1048, Dec. 1952.

Marie Knight, "A Second Skin for Patients with Large Drainage Wounds," Nursing 6(1) p. 37, 1976.

Oscar Ramirez, "Optimal Wound Healing under Op-Site Dressing" Plas. & Recon. Surg., 73(3): 474-475; 1984.

Helen Bibleheiner, "Dealing with a Wound that Drains 1.5 Liters per Day," RN Aug. 1986.

Peter Schwab, "Primary Closure of the Perineal Wound After Proctectomy" Mayo Clin. Proc., Mar. 1974, vol. 49.

Chen, L., et al., "An experimental study on the implantation of a biomaterial with electro-activity for replacement of hard tissue in bone", Hua Xi Yi Ke Da Xue Xue Bao, (2 pp. printout from PubMed); 32(4):526-8, 554, (Dec. 2001).

Aronson, J., et al., "Mechanical forces as predictors of healing during tibial lengthening by distraction osteogenesis", Clin. Orthop. Rel. Res., (301): 73-79, (Apr. 1994).

Kassis, B., et al., "Callus response to micromovement after elongation in the rabbit", J. Pediatr. Orthop., 16 (4):480-483, (Aug. 1996).

Duda, G.N., et al., "Interfragmentary motion in tibial osteotomies stabilized with ring fixators", Clin. Orthop., (396):163-172, (Mar. 2002).

Farrar, M., et al., "The Sheffield hybrid fixator—a clinical and biomechanical review", Injury, Int. J. Care Injured, 32: S-D-8-S-D-13 (2001).

Goodship, A.E., et al., "Functional adaptation of bone to increased stress", J. Bone Joint Surg., 61-A(4):539-546 (Jun. 1979).

Goodship, A.E, et al., "The influence of induced microenvironment upon the healing of experimental tibial fractures", J. Bone Joint Surg., 67-B(4):650-655 (Aug. 1985).

Goodship, A.E., et al., "Strain rate and timing of stimulation in mechanical modulation of fracture healing", Clin. Orthop. Rel. Res., (and 1 sheet printout from PubMed); (355S):S105-S115, (Oct. 1998).

Gordon, J.E., et al., "Treatment of rigid hypertrophia posttraumatic pseudarthorsis of the tibia n children using distraction osteogenesis", J. Pediatr. Orthop., 22(4): 419-423 (2002).

Kenwright, J., et al., "Controlled mechanical stimulation in the treatment of tibial fractures", Clin. Orthop. Rel. Res., (241):36-47 (Apr. 1989).

Kocaoglu, M., et al., "Treatment of humeral shaft non-unions by the Ilizarov method", Int. Orthop. (SICOT), 25:396-400 (2001).

Lanyon, L.E., et al., "Bone deformation recorded in vivo from strain gauges attached to the human tibial shaft", Acta Orthop. Scand., 46:256-268 (1975).

Mofio, M.M., et al., "Callus stimulation in distraction osteogenesis", Plast. Reconstr. Surg., 109:1621-1629 (Apr. 15, 2002).

Maffulli, N., et al., "Bone mineralization at the callotasis site after completion of lengthening", Bone, 25(3):333-338 (Sep. 1999).

Paley, O., "Current techniques of limb lengthening", J. Pediatr. Orthop., 8(1):73-92 (1988).

Pavolini, B., et al., "The Ilizarov fixator in trauma: a 10-year experience", J. Orthop. Sci., 5:108-113, (2000).

Rozbruch, S.R., et al., "Distraction of hypertrophic nonunion of tibia with deformity using Ilizarov/Taylor Spatial Frame", Arch. Orthop. Trauma Surg., 122:295-298 (2002).

Rozbruch, S.R., et al., "Distraction osteogenesis for nonunion after high tibial osteotomy", Clin. Orthop. Rel. Res., (394):227-235 (Jan. 2002).

Sakurakichi, K., et al., "Ankle arthrodesis combined with tibial lengthening using the Ilizarov apparatus", J. Orthop. Sei., 8:20-25 (2003).

Tsuchiya, H., et al., "Distraction osteogenesis for treatment of bone loss in the lower extremity", J. Orthop. Sci., 8:116-124 (2003).

Waanders, N.A., et al., "Evaluation of the mechanical environment during distraction osteogenesis", Clin. Orthop. Rel. Res., 1(349):225-234 (Apr. 1998).

Fischgrund, J., et al., "Variables affecting time to bone healing during limb lengthening", Clin. Orthop. Rel. Res., (301):31-37 (Apr. 1994).

Stokes, I.A., et al., J. Bone Joint Surg., 84(10):1842, Figure 02, (1 sheet showing "Fig. 2-A: Diagrammatic representation of the measurement of the height of the hypertrophic zone and the heights of chondroeytes"); printout dated Apr. 16, 2004.

Stokes, I.A., et al., "Enlargement of growth plate chondrocytes modulated by sustained mechanical loading", J. Bone Joint Surg. (Am.), (and 2 pp. printout from PubMed); 84-A(10):1842-1848 (Oct. 2002).

Tanaka, S.M., "A new mechanical stimulator for cultured bone cells using piezoelectric actuator", J. Biomeeh., (and 1 sheet printout from PubMed); 32(4):427-430 (Apr. 1999).

Alberty, A., et al., "Effects of distraction and compression on proliferation of growth plate chondrocytes. A study in rabbits.", Acta Orthop. Scand., (1 sheet printout from PubMed); 64(4):449-455 (Aug. 1993).

Campbell, P., "Arthrodesis of the ankle with modified distraction-compression and bone-grafting", J. Bone Joint Surg. Am., (1 sheet printout from PubMed): 72(4): 552-556 (Apr. 1990).

Monticelli, G., et al., "Leg lengthening by closed metaphyseal corticotomy", Ital. J. Orthop. Traumatol., (1 sheet printoutfram PubMed); 9(2):139-150 (Jun. 1983).

Shevtsov, V., et al., "Reduction of the period of treatment for leg lengthening. Technique and advantages", Rev. Chir. Orthop. Reparatrice Appar. Mot., (1 pp. printout from PubMed); 87(3):248-256 (May 2001).

Paley, D., "Correction of limb deformities in the 21st century", J. Pediatr. Orthop., 20(3):279-281 (May/Jun. 2000).

De Bastiani, G., et al., "Limb lengthening by callus distraction (callotasis)", J. Pediatr. Orthop., (1 sheet printout from PubMed); 7(2):129-134 (Mar./Apr. 1987).

De Bastiani, G., et al., "Dynamic axial fixation. A rational alternative for the external fixation of fractures", Int. Orthop., (1 sheet printout from PubMed); 10(2):95-99 (1986).

Patel, V.R., et al., "Nonunion of the humerus after failure of surgical treatment. Management using the Ilizarov circular fixator", J. Bone Joint Surg. Br., (1 sheet printout from PubMed); 82(7):977-83 (Sep. 2000).

Cattaneo, R., et al., "Treatment of septic or non-septic diaphyseal pseudoarthroses by Ilizarov's monofocal compression method", Rev. Chir. Orthop. Reparatrice Appar. Mot., (1 sheet printout from PubMed); 71(4):223-229 (1985).

Bronson, D.G., et al., "Stabilization of a short juxta-articular bone segment with a circular external fixator", J. Pediatr. Orthop. Part B (1 sheet printout); 11:143-149 (Apr. 2002).

Duda, G.N., et al., "Interfragmentary movements in the early phase of healing in distraction and correction osteotomies stabilized with ring fixators", Langenbecks Arch. Surg., (1 sheet printout from PubMed); 387 (11-12):433-440 (Feb. 2003).

Lascombes, P., et al., "Ilizarov's method. Histological and radiological aspects", J. Radiol., (1 sheet printout from PubMed): 72(1):11-16 (Jan. 1991).

Raschke, M., et al., "Nonunion of the humerus following intramedullary nailing treated by Ilizarov hybrid fixation", J. Orthop. Trauma, (1 sheet printout from PubMed); 12(2):138-141 (Feb. 1998).

EP 07854683—Extended European Search Report P04232EP00__ EESR (report dated Sep. 18, 2012 with Communication dated Sep. 26, 2012).

* cited by examiner

EXTERNAL FIXATION ASSEMBLY AND METHOD OF USE

RELATED APPLICATIONS

This application is a Divisional Application of U.S. patent application Ser. No. 11/694,395, filed Mar. 30, 2007 now U.S. Pat. No. 7,931,651, which claims the benefit of priority of U.S. Provisional Application No. 60/866,327, filed on Nov. 17, 2006, the entire contents of which are incorporated herein by reference.

FIELD OF THE INVENTION

The present invention relates to external fixation, and particularly to fixator pins and devices used in treating bone fractures and deformities with the use of sub-atmospheric pressure.

BACKGROUND

External fixation is a common technique used to treat a variety of conditions, including bone fractures, dislocations, and deformities. Although different techniques are used, external fixation generally involves the use of threaded fixator pins that are screwed into bone. For bone fractures, two or more fixator pins are inserted into the bone on each side of the fracture. Compression and distraction forces are applied to the fixator pins to correctly position and align the bone. External fixation may be applied over several months for complicated fractures, during which time the pin remains in the bone. Long term use of external fixator pins involves risks and complications that can delay the patient's recovery and further aggravate the patient's condition. In some patients, the pin may result in infection within the pin tract in the bone. In addition, the skin around the pin/skin interface can become irritated or infected. The pin may also become unstable and loosened in the bone. Therefore, there is a need for improved implements and devices that reduce the risks and complications associated with external fixation.

SUMMARY OF THE INVENTION

Based on the foregoing, an external fixation assembly includes a plurality of hollow fixator pins for insertion into a patient's bone. Each pin has a hollow shaft with an insertion end that may be advanced through a tissue opening and into the patient's bone. The shaft has an interior passageway or conduit such as a bore that extends generally along the longitudinal axis of the shaft. At least one vent aperture, and optionally a plurality of vent apertures, extend through the shaft in fluid communication with the bore. The pin may be removably connected to a source of vacuum pressure operable to draw fluid or gas through the aperture of the pin and apply reduced pressure in the tissue surrounding the pin. The reduced pressure may be used to stimulate blood circulation around the tissue opening, reduce the potential for inflammation and infection, and stabilize the fixator pin in the bone.

The shaft may include a first inner section or insertion end, such as a threaded section, for securing the fixator pin in the bone. In addition, the shaft may include a second outer section, such as a non-threaded section. A connection port is provided on the shaft, for example, along or at an end of the outer section to fluidly connect to or communicate with the bore inside the pin. The port may be connected to the source of vacuum pressure by a suitable connection such as a flexible tube. A cover is removably disposed around the pin and surrounds the tissue opening to form a generally fluid-tight enclosure that is sufficient to enable sub-atmospheric pressure, i.e., negative pressure, to be maintained beneath the cover. A pressure distribution element, such as a porous screen, may additionally be placed at or around the pin and between the tissue opening and the cover to prevent subatmospheric pressure to be distributed beneath the cover and at the tissue opening and, optionally, to substantially prevent direct contact between the tissue opening and the cover.

If a plurality of vent apertures are utilized, the apertures may be located on one or more sections of the shaft to apply reduced pressure to different selected locations along the shaft and optionally to different tissue areas. For example, the apertures may be formed in the outer or non-threaded section of the shaft and adapted to apply reduced pressure at the epidermis or external to the epidermis. In addition, the apertures may be formed in the inner or threaded section and adapted to apply a reduced pressure in the pin tract in the bone. Alternatively, the apertures may be formed in two separate areas on the non-threaded section of the shaft to apply reduced pressure for example, to one or more of a sub-cutaneous layer or organ, the epidermis and/or a tissue layer in the dermis. As yet a further alternative, apertures may be provided in the inner or threaded section as well as the outer or non-threaded section, as well as along different areas of the outer section, to supply reduced pressure at any one or all of the bone, sub-cutaneous tissue or organs, the dermis, the epidermis, and to areas beneath the cover and outside of the epidermis, or any other selected tissues or organs enclosed and sealed within the cover.

A method for applying external fixation using the hollow fixator pins described above includes the step of inserting each pin through a skin opening and into bone. The pin is positioned so that the apertures are in substantial alignment with selected tissue. For example, the apertures could be aligned with the epidermis, or positioned inside the pin tract in the bone or at other desired locations. Once the pins are placed, the skin opening around each pin is covered with a sealed enclosure. The hollow pins are connected to a source of vacuum pressure. The source of vacuum pressure functions to create reduced pressure that is supplied from the pin apertures in the patient's bone tissue or any soft tissues outside of the bone as desired.

DESCRIPTION OF THE DRAWINGS

The foregoing summary as well as the following description will be better understood when read in conjunction with the Figures in which.

DETAILED DESCRIPTION OF THE PREFERRED EMBODIMENT

Figure 1:
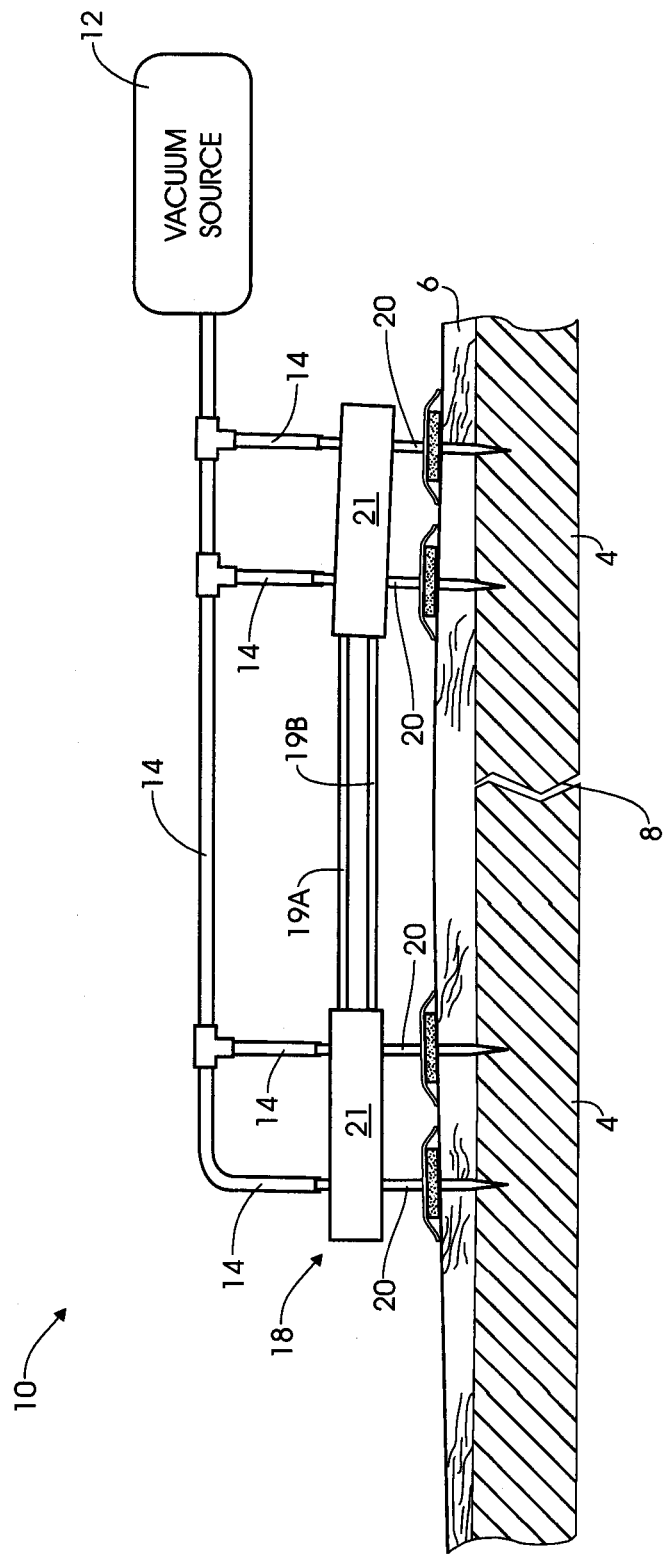
FIG. 1 is a schematic view of an external fixation assembly in accordance with the present invention.

Referring now to the drawing figures in general, and to FIG. 1 specifically, an external fixator assembly 10 is shown in accordance with the invention. In general, the fixator assembly may include four hollow fixator pins 20 inserted into bone tissue 4 in the patient on opposite sides of a fracture or other deformity 8 so that suitable compression or distraction forces can be applied. Each fixator pin 20 is positioned at a pin site and connected to a source of vacuum pressure 12. Negative or reduced pressure, e.g., sub-atmospheric pressure, is applied at each pin site to stimulate blood circulation to the pin site, to reduce the potential for inflammation and infection, and to stabilize the fixator pin. While each of the fixator pins 20 shown in FIG. 1 is a cannulated pin for supplying reduced pressure, other fixator arrangements could be utilized in which one or more fixation pins are cannulated while one or more other pins are not cannulated. The non-cannulated pins may be used at pin sites where the application of reduced pressure is contra-indicated or is not desired or needed.

Each cannulated fixator pin 20 has a hollow shaft and sidewall 23 that forms an internal bore 25. The fixator pin 20 may be cannulated from an outer end 24 to provide an access port 28 at the outer port end that leads to the internal bore that extends from the outer end 24 to the inner or tip end 27 of the pin. To preserve the integrity of the tip, the bore 25 may terminate before extending through the tip end. The fixator pin 20 is removably connected to the source of vacuum pressure 12 by suitable connectors or tubing 14, such as flexible tubes, removably coupled to the port end 24 of the pin 20. One or more vent apertures 34 extend through the sidewall 23 of the fixator pin 20 and communicate with the bore in the shaft. The source of vacuum pressure 12 is operable to draw fluid or gas through the apertures 34 and bore 25 to create negative pressure at the interface between the pin and tissue around the pin.

Referring now to FIGS. 1-2, the external fixator assembly 10 will be described in more detail. For purposes of clarity, the fixator assembly 10 is shown in simplified form with a fixator device 18 having two fixator pins 20 on each side of a bone fracture or other deformity 8. It will be appreciated that more than two fixator pins 20 may be inserted on each side of the bone fracture 8, depending on the location and nature of the fracture. In addition, it will be appreciated that the fixator assembly 10 is not strictly intended for bone fractures, and may be applied to other conditions, including for example, dislocations and deformities. The assembly 10 may incorporate a variety of fixator devices, and the specific type of fixator is not critical. For example, the fixator assembly 10 may be used with flexible or rigid fixators. In addition, the fixator assembly 10 may be applied to different fracture types and fracture locations, including for example, femoral fractures and tibial fractures.

The fixator 18 includes a pair of retainers 21, with each retainer positioned on one side of the bone fracture 8. One or more bars connect between the retainers 21 and are operable to apply compression and distraction forces on the fixator pins. In FIG. 1, the retainers 21 are connected, for example, by a compression bar 19A and a distraction bar 19B.

Figure 2A:
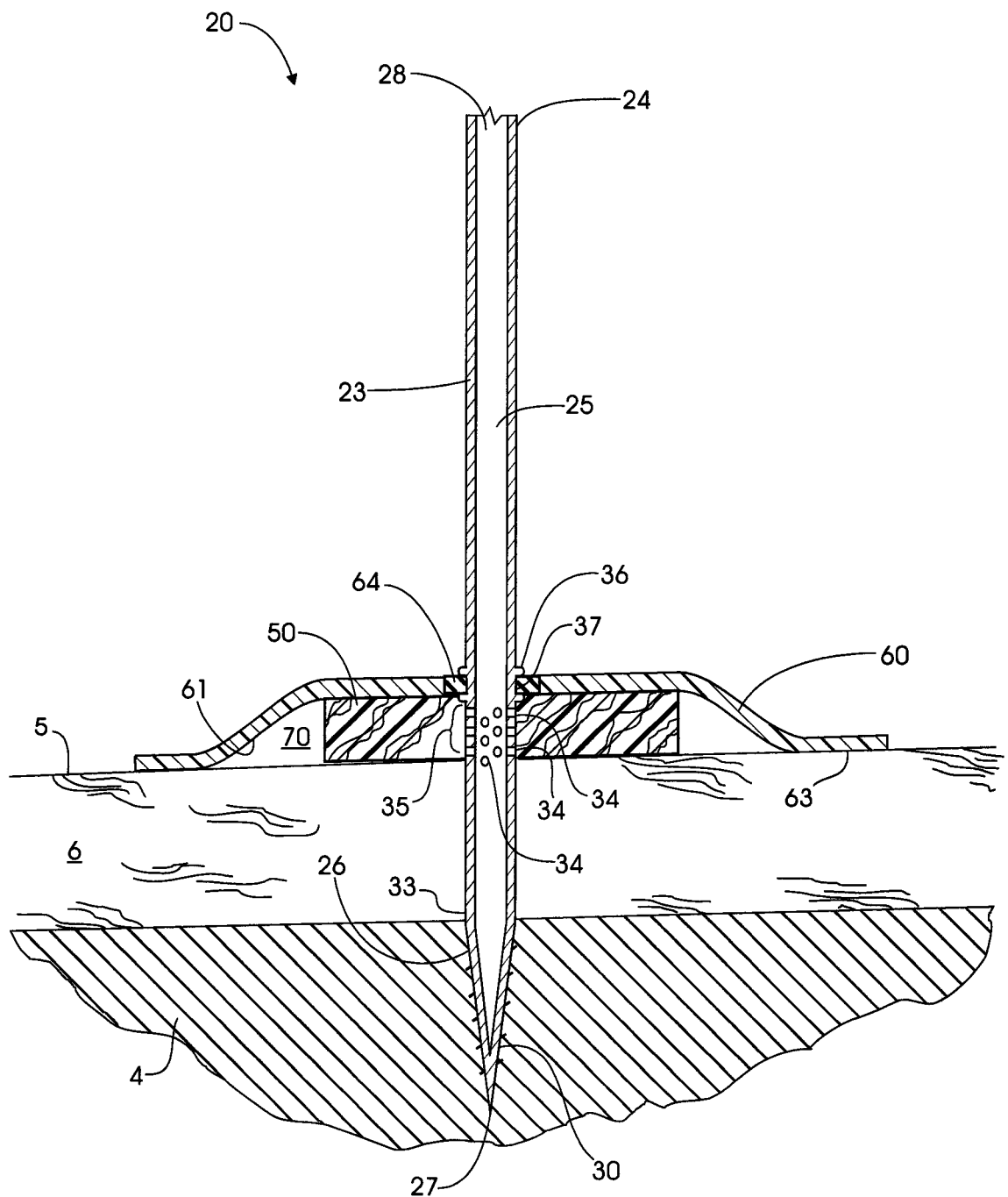
FIG. 2A is a cross-sectional view of components used in accordance with the present invention, featuring a first embodiment of a fixator pin.

Referring now to FIG. 2A, a fixator pin 20 is shown having a hollow or cannulated shaft 23 with an attachment end 24 (the port end) and an insertion end 26 (the tip end). The bore 25 extends through the hollow shaft 23 of the cannulated fixator pin 20 and provides fluid communication from the attachment end 24 to the insertion end 26. A vacuum port 28 is formed at or through the attachment end 24 of the shaft 23 and is in fluid communication with the bore 25. The attachment end 24 is adapted to receive an end of flexible tubing 14 in a sealed, snug fit as the tube slides over the attachment end 24 to provide a fluid flow path to the vacuum port 28, as shown in FIG. 1. The flexible tubing 14 has an interior lumen with a diameter substantially equal to the outer diameter of the fixator pin 20. As such, the flexible tubing 14 is configured to slide over the attachment end 24 of the fixator pin 20 and form a substantially fluid-tight seal. The flexible tube 14 connects the fixator pin 20 with a source of vacuum pressure 12. A variety of vacuum pressure sources may be used with the fixator assembly 10, including, for example a Gast Vacuum pump (Fischer Scientific).

Figure 7A:
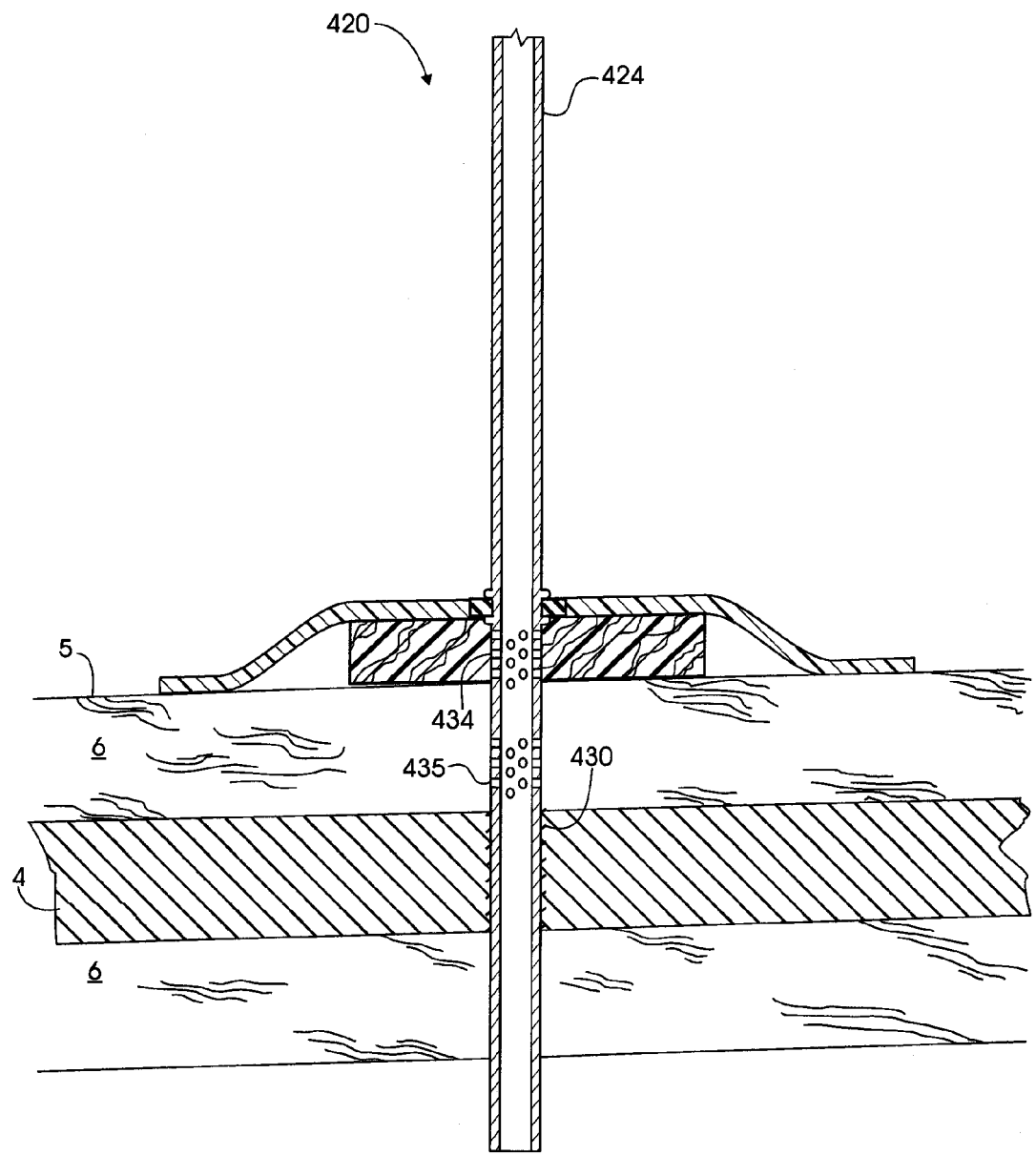
FIGS. 7A and 7B are cross-sectional view of components used in accordance with the present invention, featuring a fourth embodiment of a fixator pin.
Figure 7B:
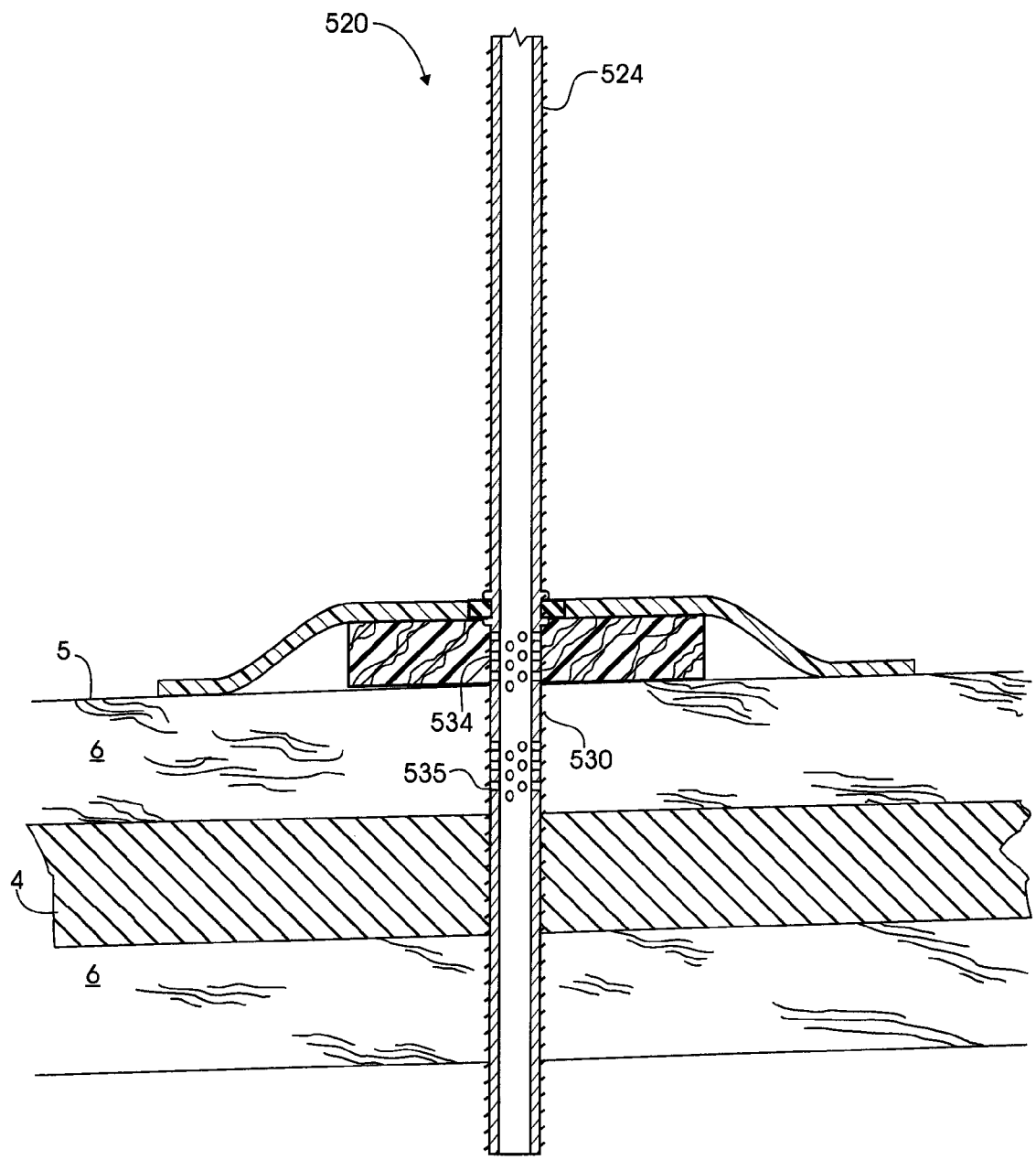

The pin 20 has a first threaded section 30 that may taper to form a sharp point or tip 27, and a second non-threaded section 33. The pin 20 may have other configurations wherein the tip end does not taper to a point or does not taper at all. The threaded section 30 is configured to penetrate into the bone 4 to securely anchor the fixator pin 20 into the pin tract in the bone 4. For this purpose, the pin may include a self-tapping threaded tip 27 for tapping into bone 4. Alternatively, the fixator pin may be provided in the from of a transfixing pin 420, 520 for positioning through a limb, FIGS. 7A and 7B. In such a use, the pin 420 may have a threaded middle portion 430 with smooth end portions or the entire pin 520 may be threaded 530, and the pin 420, 520 may be provided with a Trocar tip. Vent apertures 435, 535 may be provided in the middle portion of the pin 420, 520 or may be provided peripherally, e.g., vent apertures 434, 534.

Figure 2B:
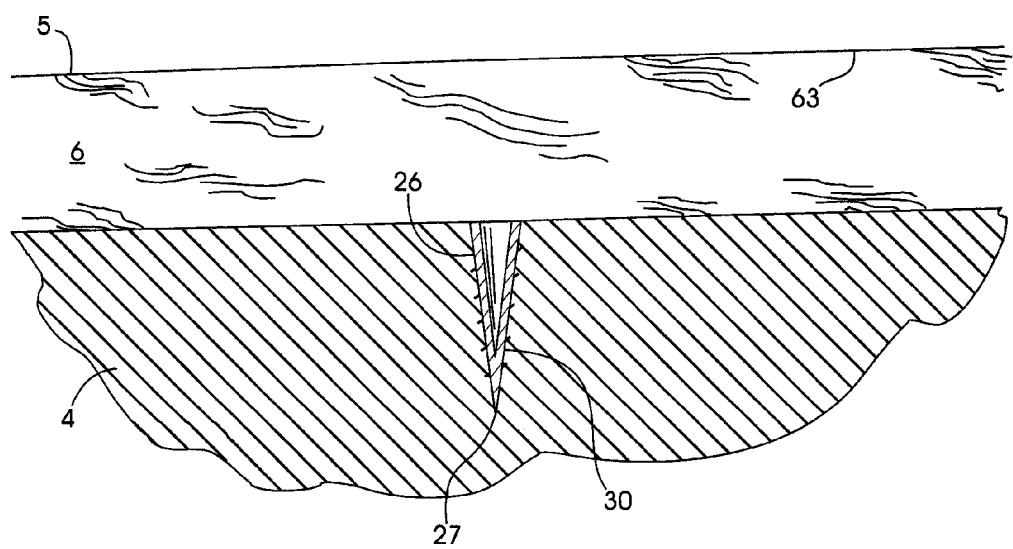
FIG. 2B is a cross-sectional view of components used in accordance with the present invention, featuring an implantable pin portion.

As shown schematically in FIG. 2A, the pin 20 screws into the bone 4 to hold the pin firmly in place. For this purpose, the pin 20 may be screwed into the bone a desired depth greater than that specifically depicted in FIG. 2A so that the non-tapered portion 33 extends into the bone to anchor the pin in place. Optionally, a portion of the pin 20, such as tip 27, may be detachable to provide an implant that may be left in the patient, as shown in FIG. 2B. In such a configuration the pin 20, or the implant portion, e.g. tip 27, may comprise a bone substitute material. For example, the pin 20 or tip 27 may comprise a natural, synthetic, or natural-synthetic hybrid porous material, and may comprise a material to support or direct osteoconduction or a material to induce differentiation of stem cells to osteogenic cells, i.e. osteoinductive agents, or materials which provide stem cells, e.g. bone marrow aspirate.

For example, the pin 20 or tip 27 may be a bioglass, ceramic material, or other natural or synthetic porous material, such as calcium sulphate or calcium phosphate. One suitable calcium sulphate bone substitute is OSTEOSET® Bone Graft Substitute, a product of Wright Medical Technology, Inc. of Arlington Tenn. Another class of suitable materials is one comprising various derivates of calcium phosphate, which can be used to provide a structural matrix for osteoconduction, such as hydroxyapatite (coral based or chemically derived synthetic ceramic), fluorapatite, tri-calcium phosphate, bioglass ceramics and combinations thereof. One suitable calcium phosphate bone substitute is OsteoGraft™ Bone Graft Substitute, a product of Millenium Biologix of Kingston, Ontario, Canada. In addition, the pin 20 or tip 27 need not comprise a bone substitute material and may comprise a metal or other suitable materials.

Figure 8:
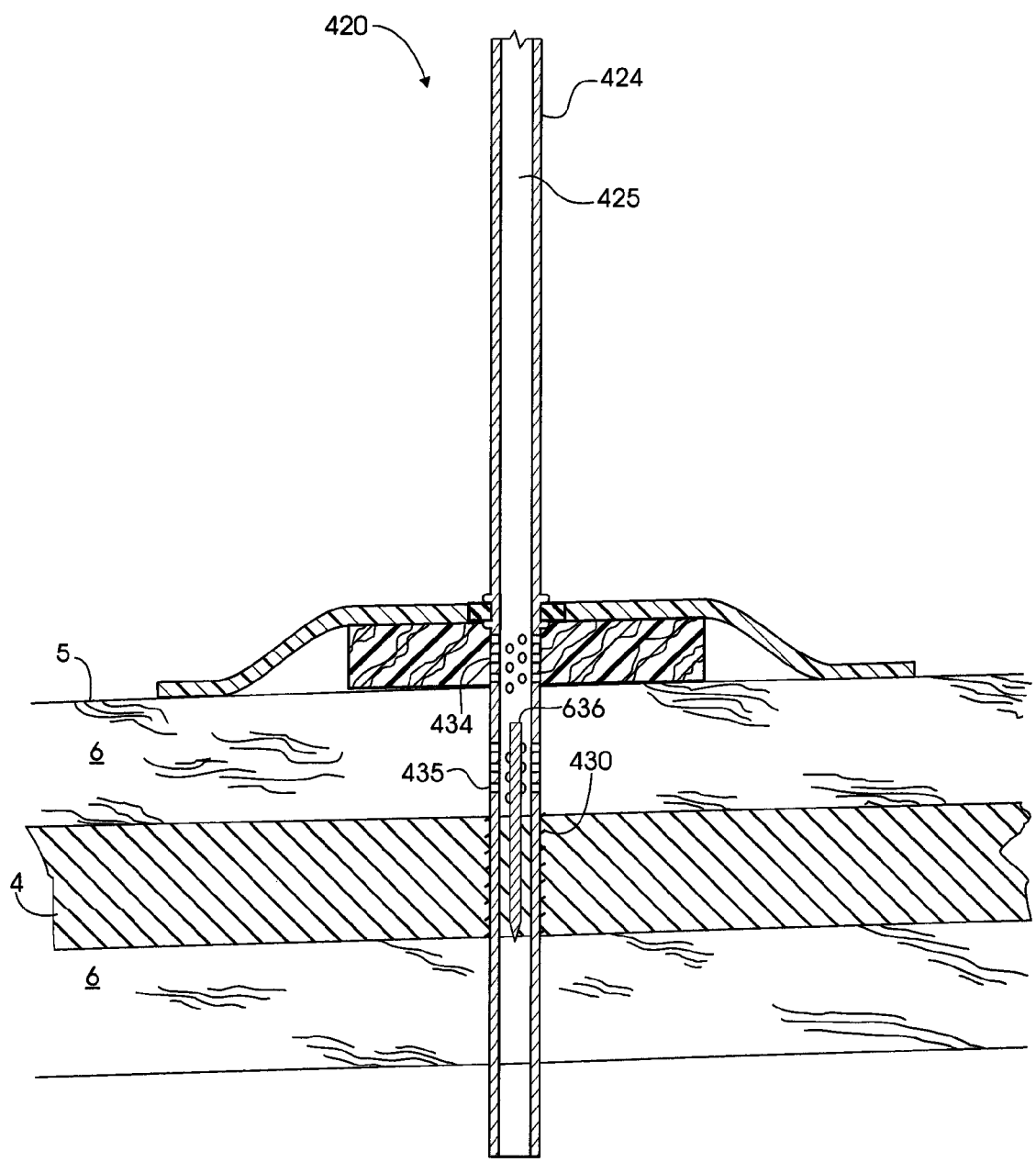
FIG. 8 is a cross-sectional view of components used in accordance with the present invention, featuring a guide pin used in conjunction with a fixator pin.

In addition, a guide pin 636 may be used in conjunction with the open-ended fixator pin 424 to aid in guiding placement of the fixator pin 424, FIG. 8. For instance, a narrow guide pin 636 having a cross-sectional dimension less than that of the bore 425 may be placed in the bone 4 prior to placement of the fixator pin 424, allowing the physician to first verify that the guide pin 636 has been placed in the correct location. The location of the guide pin 636 may be determined by an x-ray or other suitable imaging modality. After the guide pin location has been verified, the fixator pin 424 may be inserted in the bone 4 by placing the fixator pin 424 over the guide pin 636 so that the guide pin 636 is located within the bore 425 of the fixator pin.

Figure 3:
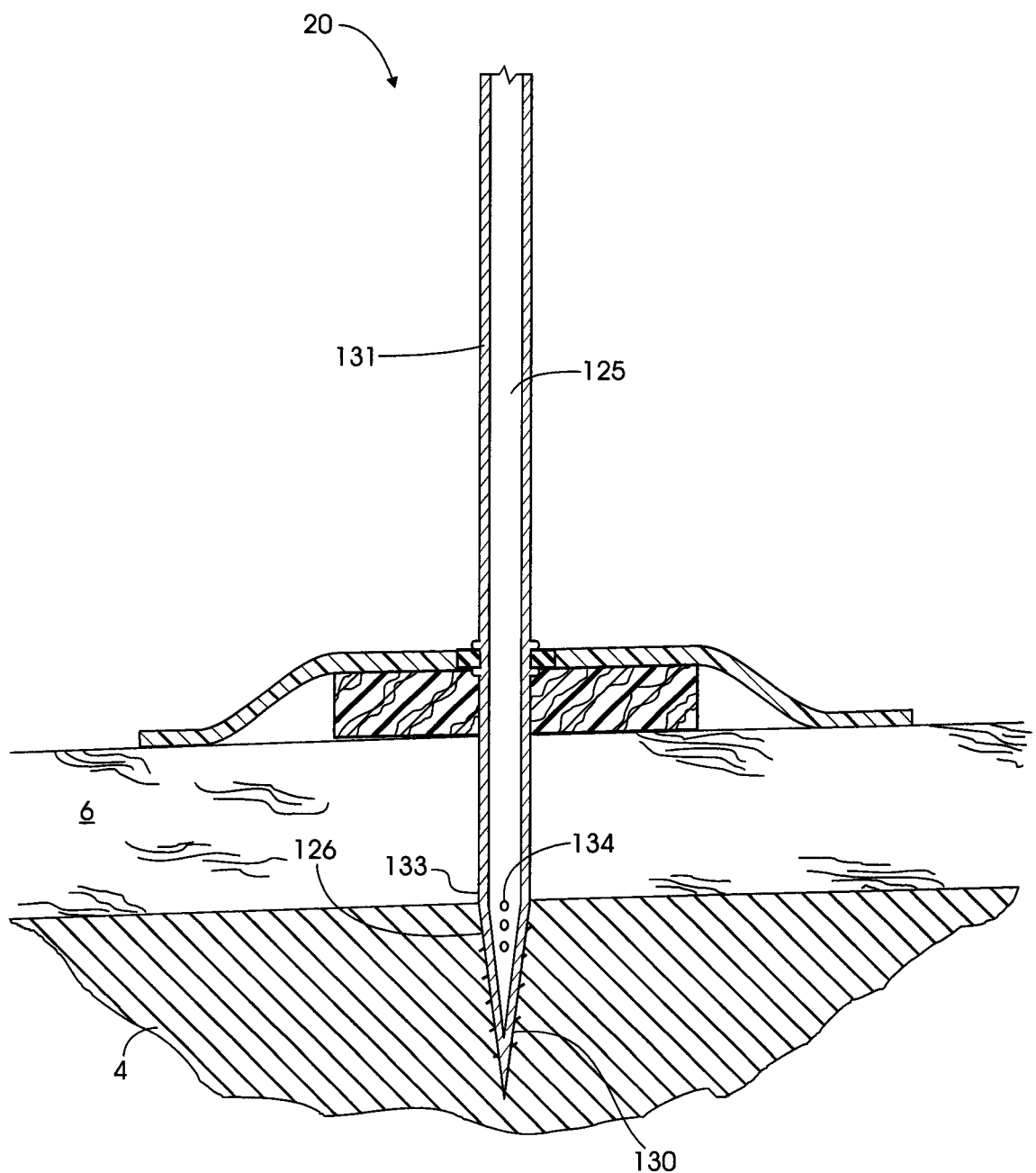
FIG. 3 is a cross-sectional view of components used in accordance with the present invention, featuring a second embodiment of a fixator pin.
Figure 6:
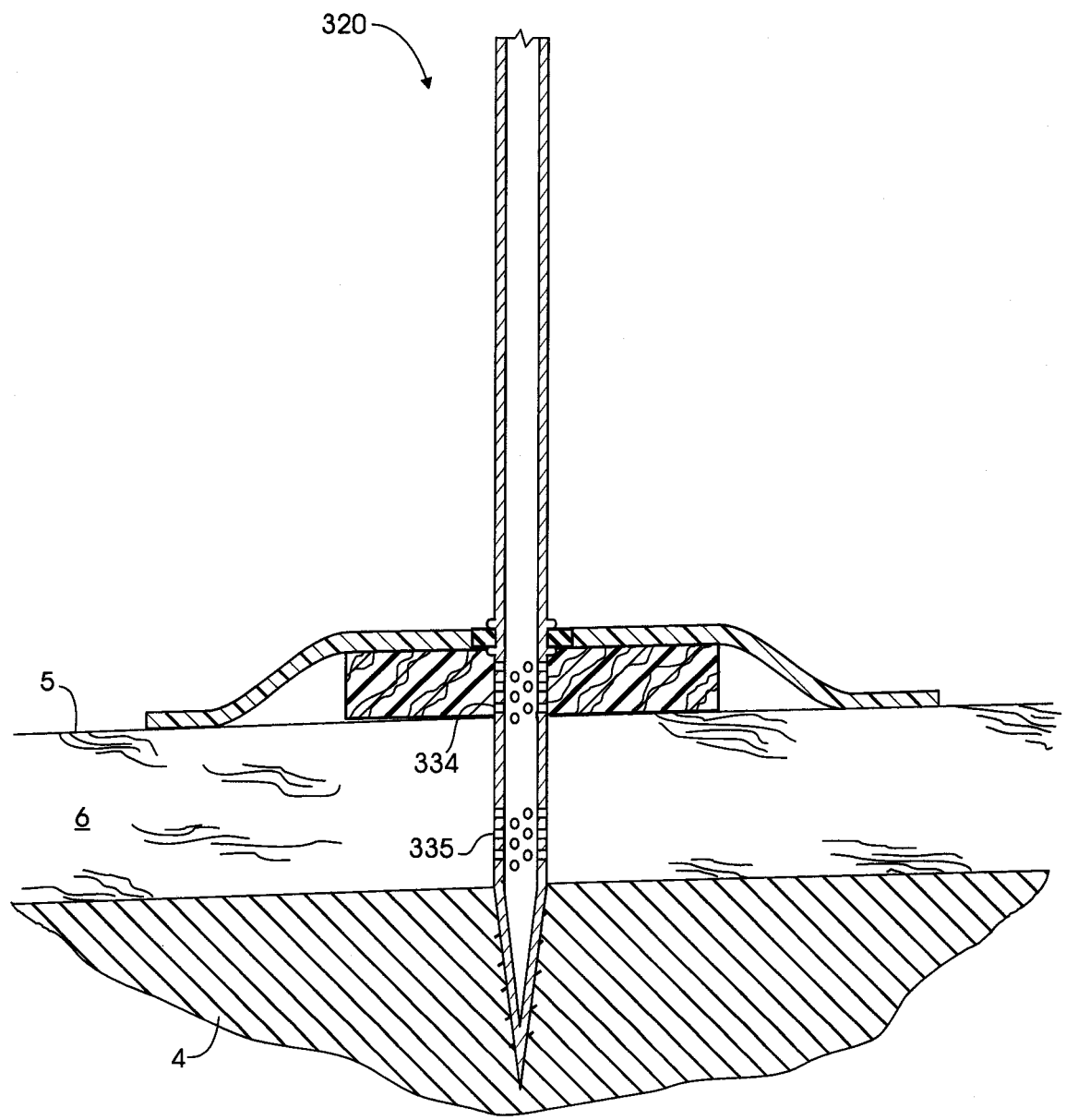
FIG. 6 is a cross-sectional view of components used in accordance with the present invention, featuring a fourth embodiment of a fixator pin.

Returning now to FIG. 2A, a plurality of apertures 34 may formed through the non-threaded section 33 of the shaft 23 to form a vent section 35 along the length of the shaft. The apertures 34 extend through the wall of the shaft 23. When the vacuum pump 12 is activated, the vacuum pump draws air or gas through the apertures 34 to create negative pressure through and along the apertures. The apertures 34 may be positioned at various locations relative to the tip 27 to apply reduced pressure at specific areas within the pin tract. For example, the apertures 34 may be positioned where the pin intersects with the epidermis 5 ("skin/pin interface"), as shown in FIG. 2. In this arrangement, the apertures may form a vent section 35 at a location at and above the epidermis to supply negative pressure through a reduced-pressure distribution element or screen 50. Alternatively, the apertures 34 may be positioned where the pin intersects deeper tissue layers in the dermis 6. Apertures may be concentrated at one section of the shaft 23 to treat a specific tissue layer, or may be formed at multiple sections of the shaft to supply reduced pressure to multiple layers or tissues. In FIG. 6, a second embodiment of a fixator pin 320 is shown with apertures 334 positioned at one section of the shaft to supply reduced pressure at the skin/pin interface and apertures 335 positioned at another section of the shaft to supply reduced pressure at deeper tissue layers in the dermis 6. As shown in FIG. 3, the tip end of the fixator pin 120 may also include apertures 134 to supply reduced pressure to bone 4 at the pin/bone interface. The pins 20, 120, 220, 320, 420, 520 may also be used intermittently or continuously to effect delivery of medication, such as antibiotics, local anesthetic, and biopharmaceuticals, to the various tissue/pin interfaces by introducing medication into the bore for delivery through the vent apertures.

A fluid-tight enclosure or cover 60, such as OpSite or TEGADERM, is positioned over the pin 20 to cover the pin site. The cover 60 is configured to form a fluid-tight seal around the pin site to maintain the reduced pressure that is applied at the tissue/pin interface. The cover 60 includes an inner face that faces into the pin site, and an outer face that faces outwardly and away from the pin site when the cover is placed over the pin 20. The inner face may include an adhesive backing 61 that adheres to the patient's skin around the periphery 63 of the pin site. Alternatively, or in addition, other adhesives or sealers may be applied. The adhesive backing has sufficient adhesive properties to form a fluid-tight enclosure around the periphery of the pin site and to hold the cover 60 in sealed contact with the patient's skin when reduced pressure is applied beneath the cover. The cover may be impermeable or semipermeable depending on the level of permeability needed or desired for a particular application as long as the desired level of reduced pressure is maintained beneath the cover for a desired amount of time to effect the desired treatment.

A hole or opening 37 is formed through a central or interior portion of the cover 60 and is adapted to fit over the attachment end 24 of the fixator pin 20 as the attachment end 24 of the pin is inserted through the hole 37. The cover 60 engages the outer circumference of the pin in a fluid tight seal to substantially prevent leakage of pressure through the hole around the pin. Optionally, the cover 60 may incorporate an O-ring seal 64 at the hole 37 in the cover that is adapted to squeeze around and seal onto the outer periphery of the pin. The O-ring 64 engages the exterior of the fixator pin 20 when the cover is placed over the pin. The O-ring 64 has an inner diameter substantially equal to the outer diameter of the fixator pin 20 and is configured to frictionally engage the outer surface of the pin. The O-ring 64 may be affixed to the cover 60 around the hole 37 by an adhesive or other bonding. Alternatively, the O-ring may be embedded within the cover or heat sealed into the cover. For example, the cover 60 may include two plies that form a pocket in which the O-ring 64 is embedded. The frictional engagement between the O-ring 64 and pin 20 forms a fluid-tight seal between the exterior of the pin and the cover.

It may be desirable to stabilize the O-ring axially on the pin 20. Referring to FIG. 2A, the pin 20 includes a pair of circumferential ridges 36 on the outer section of the pin that form a seat for the O-ring 64. The ridges 36 form a narrow groove having a thickness and diameter suitable to seat the O-ring 64. The groove is adapted to receive the O-ring when the cover is placed over the pin 20. As a result, the seat formed by the ridges 36 limits the axial displacement of the O-ring 64 and cover 60 along the length of the pin 20. The O-ring may be formed of any flexible elastomeric material that permits the O-ring to be stretched. In this way, the O-ring 64 can be stretched to temporarily expand the inside diameter of the O-ring to allow it to be slipped over the top ridge and into the seat allowing the O-ring to slide into and become properly seated within the seat groove.

A reduced-pressure distribution element such as a porous screen 50 may surround the apertures 34 on the fixator pin 20 as shown in FIG. 2A. The screen 50 is positioned beneath the cover 60 and over the pin site to help distribute reduced pressure across its surface area and to optionally help keep the cover out of direct contact with the skin around the pin 20. The screen 50 has sufficient porosity to permit the flow of gases into the apertures of the pin when reduced pressure is applied by the vacuum pump. The screen 50 may also absorb exudate and other liquids that may aspirate from the tissue around the pin site. Preferably, the screen 50 is formed out of an open cell polymer foam, such as polyurethane foam. Other porous or perforated materials may also be used. Foams may be used with a wide range of pore sizes and densities. Since the fixator assembly 10 usually rests on top of the patient's extremity, it may be desirable to select a light-weight low density foam or sponge that is less noticeable to the patient. It may optionally be desirable to form large perforations or other flow paths in the screen 50 to reduce the weight of the screen or to increase the flow of gas drawn by the vacuum pump. In FIG. 2A, the screen 50 and cover 60 are cut to fit over a single pin site. Other screen and cover configurations may be used, however, and the configurations illustrated in the drawing figures are not intended to be the only workable configurations. For example, it may be desirable to use a single screen 50 and cover 60 over multiple pin sites. This may be desirable where pins are spaced close together in a relatively small area.

The fixator assembly 10 may be used in the following manner. After the pin locations are selected, small incisions are made through the skin at the pin locations, and the fixator pins 20 are placed into the patient's bone. The desired pin location may include a fracture or a joint to be immobilized. In such a case where the pin 20 is inserted in the fracture or joint, the pin 20 may desirably include an implantable portion which may optionally comprises a bone substitute material. The pins 20 are advanced into the bone until the pin apertures are positioned at a desired axial locations relative to the tissue/pin interface. For example, as shown in FIG. 2A, the apertures 34 may be positioned at the skin/pin interface in substantial alignment at, with or above the epidermis 5 or in communication with the screen 50. Alternatively, as shown in FIG. 6, the apertures 335 may also be positioned adjacent to tissue in the dermis 6 either exclusively or in conjunction with apertures at another location such apertures 334 at or above the epidermis 5. Apertures may be provided at other locations as well. Screens 50 are secured over the pins around the apertures and over the incisions. Covers 60 are then placed over the pins 20, and the adhesive surfaces on the inner faces of the covers are pressed firmly against the patient's skin to form a fluid tight enclosure around the pin sites. Many types of suitable covers may be used. The fixator 18 is then assembled and connected with the fixator pins. Once the fixator 18 is assembled, flexible tubes 14 are connected to the attachment ends of the fixator pins 20 and to the suction port of the vacuum pump 12.

The vacuum pump 12 is connected to a power source and switched on to apply reduced pressure within the space 70 beneath the cover 60 as shown in FIG. 2A. The amount of pressure reduction applied at the pin sites is dependent on the desired course of treatment, the location of the pins, the density of the screen material, and other variables. For example, the reduced pressure may be between 10 mm Hg below atmospheric pressure and 300 mm Hg below atmospheric pressure. In the embodiment shown in FIG. 3, reduced pressure is supplied to the pin/bone interface at apertures 134 while the cover and optional screen help to maintain the negative pressure at that site.

Thus far, the fixator pins have been described primarily with apertures that are positioned to apply reduced pressure at the epidermis and/or dermis. It will be appreciated that reduced pressure may be applied at deeper levels in the pin incision and need not be limited to the dermis or epidermis. For example, reduced pressure may be applied, as shown in FIG. 3, at the interface between the fixator pin and bone ("bone/pin interface") by apertures 134 positioned at the bone 4 of FIG. 3. Application of reduced pressure in bone tissue is intended to reduce the occurrence of pin tract infection and inflammation in the bone. In addition, the application of reduced pressure in bone tissue is intended to increase bone growth and bone ingrowth in the pin tract, which increases stability of the pin.

Figure 4:
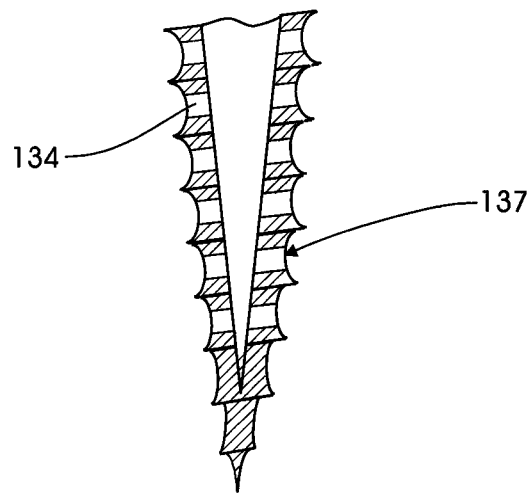
FIG. 4 is an enlarged cross-sectional view of a threaded section of the fixator pin of FIG. 3, broken away at one end for clarity.

Referring now more specifically to FIG. 3, a third embodiment of a fixator pin 120 is shown. The fixator pin 120 is configured to apply reduced pressure at the bone/pin interface in a pin tract. The fixator pin 120 is substantially similar to the pins described above, having a hollow shaft 131 with a central bore 125, an insertion end 126, a threaded section 130 on the insertion end, a non-threaded section 133, and a plurality of apertures 134. The apertures 134 are formed in the threaded section 130 of the insertion end 126 as opposed to the non-threaded section 133 of the shaft. In this way, the reduced pressure is applied through bore 125 to the pin tract inside the bone 4. Referring to FIG. 4, the apertures 134 are preferably recessed in the groove formed by the thread on the threaded section at the tip 137. The groove provides additional void space around the apertures to reduce the potential for clogging caused by bone fragments that may become lodged in the apertures.

Figure 5:
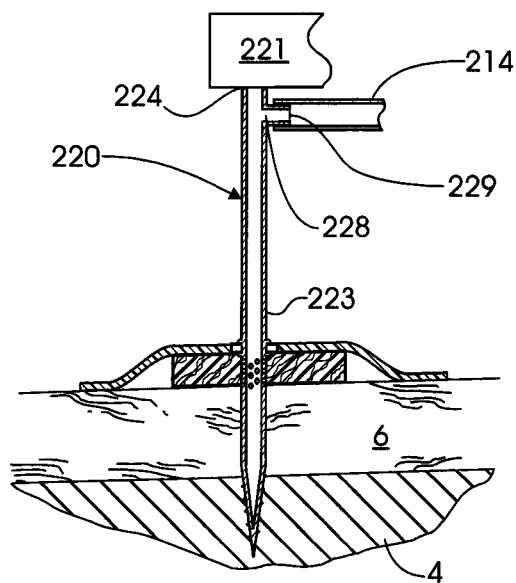
FIG. 5 is a cross-sectional view of components used in accordance with the present invention, featuring a third embodiment of a fixator pin.

In some cases, it may be desirable to locate the vacuum port as a side port on the side of the pin, rather than at the attachment end. For example, the fixator appliance may have retainers that connect over the top of the fixator pins, covering the attachment ends of the pins and preventing connection of flexible tubing to the attachment ends. Therefore, locating the vacuum port on the side of the pin can avoid problems that occur when the attachment end is obstructed or inaccessible. In FIG. 5, a fourth embodiment of a fixator pin 220 is shown in accordance with the invention. The fixator pin 220 is connected to a retainer 221 that covers the end of the fixator pin. A vacuum port 228 is formed through the side wall of the pin 220 and connects with a flexible tube 214. A cylindrical hub 229 surrounds the vacuum port 228 and projects radially outwardly from the side wall of the pin 220. The flexible tube 214 is adapted to slide over the hub 229 to connect the port 228 to a vacuum pump or other source of reduced pressure. The hub 229 has an outer diameter that is substantially equal to the inner diameter of the flexible tube 214. In this way, the flexible tube slides over the hub in frictional engagement to form a fluid-tight seal around the port 228.

The terms and expressions which have been employed are used as terms of description and not of limitation. There is no intention in the use of such terms and expressions of excluding any equivalents of the features shown and described or portions thereof. It is recognized, therefore, that various modifications are possible within the scope and spirit of the invention. Accordingly, the invention incorporates variations that fall within the scope of the following claims.

What is claimed is:

1. A fixation device comprising:
   a. a fixator pin having a hollow shaft that extends along a longitudinal axis of the fixator pin, the fixator pin comprising a threaded section and a non-threaded section, the threaded section configured to be screwed into bone;
   b. a cover disposed about the fixator pin and sealed to the fixator pin to provide an enclosure configured to maintain negative pressure beneath the cover;
   c. at least one aperture in the fixator pin that extends through a side wall of the pin in fluid communication with the hollow shaft, the at least one aperture disposed beneath the cover in fluid communication with the enclosure; and
   d. a vacuum source in fluid communication with the hollow shaft, the vacuum source adapted to provide and maintain negative pressure through the at least one aperture to the enclosure beneath the cover.

2. The fixation device of claim 1, wherein the at least one aperture is provided in the non-threaded section of the fixator pin.

3. The fixation device of claim 1, wherein the at least one aperture is a plurality of apertures.

4. The fixation device of claim 1, wherein the fixator pin comprises a proximal end, connected to the vacuum source, and a distal end comprising the threaded section.

5. The fixation device of claim 1, comprising a detachable shaft section to provide an implant that may be left in a bone.

6. The fixation device of claim 5, wherein the detachable shaft section comprises a bone substitute material.

7. The fixation device of claim 6, wherein the bone substitute material comprises an osteoconductive material, osteoinductive material, or combinations thereof.

8. The fixation device of claim 6, wherein the bone substitute material comprises a bioglass, a ceramic material, calcium sulfate, calcium phosphate, hydroxyapatite, fluoroapatite, tri-calcium phosphate, bioglass ceramics, or combinations thereof.

9. The fixation device of claim 1, wherein the fixator pin comprises a bone substitute material.

10. The fixation device of claim 9, wherein the bone substitute comprises an osteoconductive material, an osteoinductive material, or combinations thereof.

11. The fixation device of claim 9, wherein the bone substitute comprises a bioglass, a ceramic material, calcium sulfate, calcium phosphate, hydroxyapatite, fluoroapatite, tri-calcium phosphate, bioglass ceramics, or combinations thereof.

12. The fixation device of claim 1, comprising a guide pin for introduction into a bone, and wherein the hollow shaft of the fixator pin is dimensioned to permit the guide pin to be inserted into the hollow shaft.

13. The fixation device of claim 1, comprising:
   a. a reduced pressure distribution element disposed around the fixator pin and beneath the cover; and
   b. a flexible tube in fluid communication with the hollow shaft and adapted to provide negative pressure from the vacuum source to the hollow shaft.

14. The fixation device of claim 13, wherein the at least one aperture is provided in the non-threaded section of the fixator pin.

15. The fixation device of claim 13, wherein the at least one aperture is a plurality of apertures.

16. The fixation device of claim 13, wherein the fixator pin comprises a proximal end, connected to the vacuum source and a distal end comprising the threaded section.

17. The fixation device of claim 13, wherein the reduced pressure distribution element comprises an open-cell foam.

18. The fixation device of claim 13, comprising a detachable shaft section to provide an implant that may be left in a bone.

19. The fixation device of claim 18, wherein the detachable shaft section comprises a bone substitute material.

20. The fixation device of claim 19, wherein the bone substitute material comprises an osteoconductive material, osteoinductive material, or combinations thereof.

21. The fixation device of claim 19, wherein the bone substitute material comprises a bioglass, a ceramic material, calcium sulfate, calcium phosphate, hydroxyapatite, fluoroapatite, tri-calcium phosphate, bioglass ceramics, or combinations thereof.

22. The fixation device of claim 13, wherein the fixator pin comprises a bone substitute material.

23. The fixation device of claim 22, wherein the bone substitute material comprises an osteoconductive material, osteoinductive material, or combinations thereof.

24. The fixation device of claim 22, wherein the bone substitute material comprises a bioglass, a ceramic material, calcium sulfate, calcium phosphate, hydroxyapatite, fluoroapatite, tri-calcium phosphate, bioglass ceramics, or combinations thereof.

25. The fixation device of claim 13, comprising a guide pin for introduction into a bone, and wherein the hollow shaft of the fixator pin is dimensioned to permit the guide pin to be inserted into the hollow shaft.

* * * * *